United States Patent
Giardello et al.

(10) Patent No.: US 10,501,488 B2
(45) Date of Patent: Dec. 10, 2019

(54) METAL CARBENE OLEFIN METATHESIS CATALYSTS

(71) Applicant: Umicore AG & Co. KG, Hanau-Wolfgang (DE)

(72) Inventors: Michael A. Giardello, Pasadena, CA (US); Mark S. Trimmer, Monrovia, CA (US); Li-Sheng Wang, Azusa, CA (US); Noah H. Duffy, Pasadena, CA (US); Adam M. Johns, Claremont, CA (US); Nicholas J. Rodak, South Pasadena, CA (US); Bryan A. Fiamengo, Anaheim, CA (US); John H. Phillips, Pasadena, CA (US)

(73) Assignee: Umicore AG & Co. KG (DE)

( * ) Notice: Subject to any disclaimer, the term of this patent is extended or adjusted under 35 U.S.C. 154(b) by 0 days.

(21) Appl. No.: 15/762,918

(22) PCT Filed: Sep. 23, 2016

(86) PCT No.: PCT/US2016/053288
§ 371 (c)(1),
(2) Date: Mar. 23, 2018

(87) PCT Pub. No.: WO2017/053690
PCT Pub. Date: Mar. 30, 2017

(65) Prior Publication Data
US 2018/0265532 A1    Sep. 20, 2018

Related U.S. Application Data

(60) Provisional application No. 62/222,989, filed on Sep. 24, 2015.

(51) Int. Cl.
| | | |
|---|---|---|
| *C07F 15/00* | (2006.01) | |
| *C08G 61/08* | (2006.01) | |
| *C08L 65/00* | (2006.01) | |

(52) U.S. Cl.
CPC .......... *C07F 15/0046* (2013.01); *C08G 61/08* (2013.01); *C08L 65/00* (2013.01);
(Continued)

(58) Field of Classification Search
CPC ....... C07F 15/0046; C08L 65/00; C08G 61/08
See application file for complete search history.

(56) References Cited

U.S. PATENT DOCUMENTS

| | | |
|---|---|---|
| 4,899,005 A | 2/1990 | Lane et al. |
| 5,204,427 A | 4/1993 | Torii et al. |

(Continued)

FOREIGN PATENT DOCUMENTS

| | | |
|---|---|---|
| WO | WO-2000046257 A1 | 8/2000 |
| WO | WO-2002076613 A1 | 10/2002 |

(Continued)

OTHER PUBLICATIONS

Bantreil et al., "Mixed N-Heterocyclic Carbene/Phosphite Ruthenium Complexes: Towards a New Generation of Olefin Metathesis Catalysts", *Chem. Commun.*, vol. 46, pp. 7115-7117 (2010).

(Continued)

*Primary Examiner* — Catherine S Branch
(74) *Attorney, Agent, or Firm* — Drinker Biddle & Reath LLP

(57) ABSTRACT

This invention relates generally to metal carbene olefin metathesis catalyst compounds, to the preparation of such compounds, compositions comprising such compounds, methods of using such compounds, articles of manufacture comprising such compounds, and the use of such compounds in the metathesis of olefins and olefin compounds. The invention has utility in the fields of catalysts, organic synthesis, polymer chemistry, and industrial and fine chemicals industry.

17 Claims, 2 Drawing Sheets

(52) U.S. Cl.
CPC ............... *C08G 2261/3324* (2013.01); *C08G 2261/3325* (2013.01); *C08G 2261/418* (2013.01)

(56) References Cited

U.S. PATENT DOCUMENTS

| | | | |
|---|---|---|---|
| 5,728,785 | A | 3/1998 | Grubbs et al. |
| 5,939,504 | A | 8/1999 | Woodson, Jr. et al. |
| 6,281,307 | B1 | 8/2001 | Mühlebach et al. |
| 6,436,476 | B1 | 8/2002 | Sage, Jr. |
| 6,552,139 | B1 | 4/2003 | Herrmann et al. |
| 6,635,768 | B1 | 10/2003 | Herrmann et al. |
| 6,787,620 | B2 | 9/2004 | Herrmann et al. |
| 6,838,489 | B2 | 1/2005 | Bell et al. |
| 6,890,650 | B2 | 5/2005 | Hedden |
| 7,294,717 | B2 | 11/2007 | Herrmann et al. |
| 7,329,758 | B1 | 2/2008 | Grubbs et al. |
| 7,378,528 | B2 | 5/2008 | Herrmann et al. |
| 7,622,590 | B1 | 11/2009 | Nolan et al. |
| 7,652,145 | B2 | 1/2010 | Herrmann et al. |
| 9,233,994 | B2 | 1/2016 | Cazin |
| 9,815,765 | B2 | 11/2017 | Cazin |
| 2005/0261451 | A1 | 11/2005 | Ling et al. |
| 2010/0087600 | A1 | 4/2010 | Müller et al. |
| 2011/0160472 | A1 | 6/2011 | Lemke et al. |
| 2013/0165649 | A1 | 6/2013 | Cazin |
| 2014/0228563 | A1 | 8/2014 | Cazin |
| 2014/0357820 | A1 | 12/2014 | Stephen et al. |
| 2018/0065914 | A1 | 3/2018 | Cazin |

FOREIGN PATENT DOCUMENTS

| | | | | |
|---|---|---|---|---|
| WO | WO-2011117571 | A1 | 9/2011 | |
| WO | WO-2012174502 | A2 | 12/2012 | |
| WO | WO-2013045876 | A1 | 4/2013 | |
| WO | WO-2015106210 | A1 * | 7/2015 | ............. C03C 25/30 |

OTHER PUBLICATIONS

Barbasiewicz et al., "Probing of the LIgand Anatomy: Effects of the Chelating Alkoxy Ligand Modifications on the Structure and Catalytic Activity of Ruthenium Carbene Complexes", *Adv. Synth. Catal.*, vol. 349, pp. 193-203 (2007).

Barbasiewicz et al., "Structure and Activity Peculiarities of Ruthenium Quinoline and Quinoxaline Complexes: Novel Metathesis Catalysts", Organometallics, vol. 25, pp. 35-99-3604 (2006).

Ben-Asuly et al., "A Thermally Switchable Latent Ruthenium Olefin Metathesis Catalyst", Organometallics, vol. 27, pp. 811-813 (2008).

Ben-Asuly et al., "Photoactivation of Ruthenium Olefin Metathesis Initiators", Organometallics, vol. 28, pp. 4652-4655 (2009).

Benitez et al., "Conformational Analysis of Olefin#Carbene Ruthenium Metathesis Catalysts", Organometallics, vol. 28, pp. 2643-2645 (2009).

Benitez et al., "The Isomerization Equilibrium Between Cis and Trans Chloride Ruthenium Olefin Metathesis Cataltysts from Quantum Mechanics Calculations", J. Am. Chem. Soc., vol. 127, pp. 12218-12219 (2005).

Diesendruck et al., "Predicing the Cis-Trans Dichloro Configuration of Group 15-16 Chelated Ruthenium Olefin Metathesis Complexes: A DFT and Experimental Study", *Inorg. Chem.*, vol. 48, pp. 10819-10825 (2009).

Isik et al., "Tunable Ferrocenyl-Phosphinite Ligands for the Ruthenium(II)-Catalyzed Asymmetric Transfer Hydrogenation of Ketones", Journal of Molecular Catalysis A: Chemical, vol. 379, pp. 225-233 (2013).

Love et al., "Synthesis, Structure, and Activity of Enghanced Initiators for Olefin Metathesis", Arnold and Nabel Beckman Laboratories for Chemical Synthesis, Division of Chemistry and Chemical Engineering, California Institute of Technology, Pasadena, CA, 67 pages.

Love et al., "Synthesis, Structure, and Activity of Enhanced Intiators for Olefin Metathesis", J. Am. Chem. Soc., vol. 125, pp. 10103-10109 (2003).

Nguyen et al., "Syntheses and Activities of New Single-Component, Rutheium-Based Olefin Metathesis Catalysts", *J. Am. Chem. Soc*, vol. 115, pp. 9858-9859 (1993).

Prühs et al., "Preparation, Reactivity, and Structural Peculiarities of Hydroxyalkyl-Functionalized "Second-Generation" Ruthenium Carbene Complexes", Organometallics, vol. 23, pp. 280-287 (2004).

Sanford, "Synthetic and Mechanistic Investigations of Ruthenium Olefin Metathesis Catalysts", Thesis—California Institute of Technology, Pasadena, CA, 211 pages (2001).

Slugovc et al., ""Second Generation" Ruthenium Carbene Complexes with a cis-Dichloro Arrangement", Organometallics, vol. 23, pp. 3622-3626 (2004).

Ung et al., "Latent Ruthenium Olefin Metathesis Catalysts That Contain an N-Heterocyclic Carbene Ligand", Organometallics, vol. 23, pp. 5399-5401 (2004).

Zirngast et al., "Pyridine as Trigger for Chloride Isomerisation in Chelated Rutheinum Benzylidene complexes: Implications for Olefin Metathesis", *Chem. Commun.*, vol. 47, pp. 2261-2263 (2011).

International Search Report for PCT/US2016/053288 dated Feb. 16, 2017.

Written Opinion of the International Searching Authority for PCT/US2016/053288 dated Feb. 16, 2017.

* cited by examiner

METAL CARBENE OLEFIN METATHESIS CATALYSTS

RELATED APPLICATIONS

This application is a national stage application (under 35 U.S.C. § 371) of PCT/US2016/053288, filed Sep. 23, 2016, which claims the benefit of U.S. Provisional Patent Application No. 62/222,989, filed Sep. 24, 2015, the contents of which are incorporated herein by reference.

TECHNICAL FIELD

This invention relates generally to metal carbene olefin metathesis catalyst compounds, to the preparation of such compounds, compositions comprising such compounds, methods of using such compounds, articles of manufacture comprising such compounds, and the use of such compounds in the metathesis of olefins and olefin compounds. The invention has utility in the fields of catalysts, organic synthesis, polymer chemistry, and industrial and fine chemicals industry.

BACKGROUND

In recent years, olefin metathesis reactions utilizing metathesis catalysts have become one of the most useful tools in organic chemistry. A wide variety of ruthenium metathesis catalysts possessing monodentate mixed ligand systems such as mixed N-heterocyclic carbene (NHC)/phosphine ligand systems are known and have been studied, a few examples of which are shown in Scheme 1. The benefits of ruthenium-metathesis catalysts possessing monodentate mixed NHC/phosphine ligand systems is well known in the art.

Scheme 1

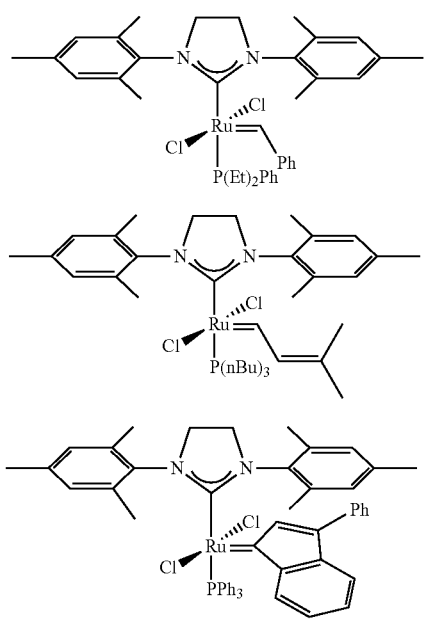

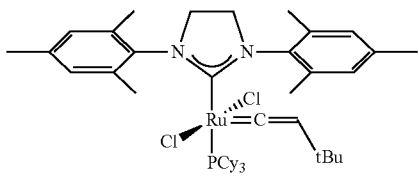

One particularly important olefin metathesis reaction is ring opening metathesis polymerization (ROMP). The molding of thermoset polymers by ROMP is a technologically and commercially important processing technique. In this technique, a liquid monomer (e.g., at least one cyclic olefin) and a polymerization catalyst (e.g., at least one metal carbene olefin metathesis catalyst) are mixed to form a ROMP composition, and the ROMP composition is poured, cast or injected into a mold. The polymerization proceeds and upon completion the molded part is removed from the mold for any optional post cure processing that is required. The ROMP composition may optionally contain added modifiers, fillers, additives, reinforcements, pigments, etc.

Unfortunately little work involving ruthenium metathesis catalysts possessing monodentate mixed ligand systems other than mixed NHC/phosphine ligand systems has been disclosed. Furthermore, many of the previously known ruthenium metathesis catalysts possessing mixed NHC/phosphine ligand systems possess characteristics which in some instances limit their use in certain applications and olefin metathesis reactions. Therefore, there is an ongoing need for metal carbene olefin metathesis catalysts, particularly ruthenium metathesis catalysts containing monodentate mixed ligand systems with improved characteristics which will further enable their use in a wider array of applications and olefin metathesis reactions.

SUMMARY OF THE INVENTION

To meet this need the inventors have discovered various metal carbene olefin metathesis catalysts of the invention as described herein.

In one embodiment, the invention provides a metal carbene olefin metathesis catalysts of the invention comprising a Group 8 transition metal complex having the structure of Formula (I):

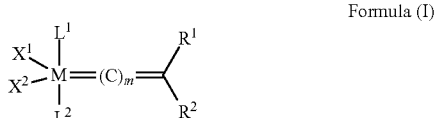

wherein:

$L^1$ is a carbene ligand having the structure of Formula (II):

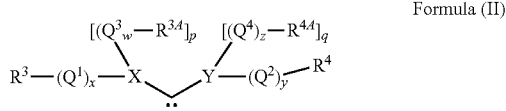

M is a Group 8 transition metal, particularly Ruthenium or Osmium; more particularly Ruthenium;

X and Y are independently CH, C, N, O, S or P, preferably X and Y are both N;

$Q^1$, $Q^2$, $Q^3$, and $Q^4$ are independently linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, or, two or more substituents on adjacent atoms within $Q^1$, $Q^2$, $Q^3$, and $Q^4$ may be linked to form an additional cyclic group;

p and q are independently 0 or 1 or 2;

w, x, y, and z are independently 0 or 1, preferably w, x, y, and z are 0;

$R^3$, $R^{3.4}$, $R^4$, and $R^{4.4}$ are independently hydrogen, hydrocarbyl, substituted hydrocarbyl, heteroatom-containing hydrocarbyl, and substituted heteroatom-containing hydrocarbyl;

$L^2$ is a phosphinite or a phosphonite ligand;

$X^1$ and $X^2$ are independently anionic ligands and are bonded to M in a trans orientation or in a cis orientation;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring);

and with the provisos:

p is 0 when X is O or S;
p is 1 when X is N, CH or P;
p is 2 when X is C;
q is 0 when Y is O or S;
q is 1 when Y is N, CH or P;
q is 2 when Y is C;
no more than one of X or Y is C or CH; and
the catalyst of Formula (I) is not of structures:

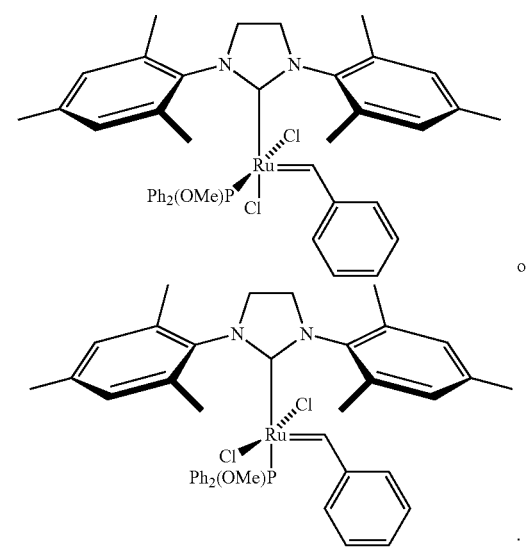

or

In one embodiment, the invention provides a ROMP composition comprising at least one resin composition and at least one metal carbene olefin metathesis catalyst, wherein the resin composition comprises at least one cyclic olefin.

In one embodiment, the invention provides a ROMP composition comprising at least one resin composition and at least one metal carbene olefin metathesis catalyst, wherein the resin composition comprises at least one cyclic olefin, with the proviso that the at least one metal carbene olefin metathesis catalyst is not

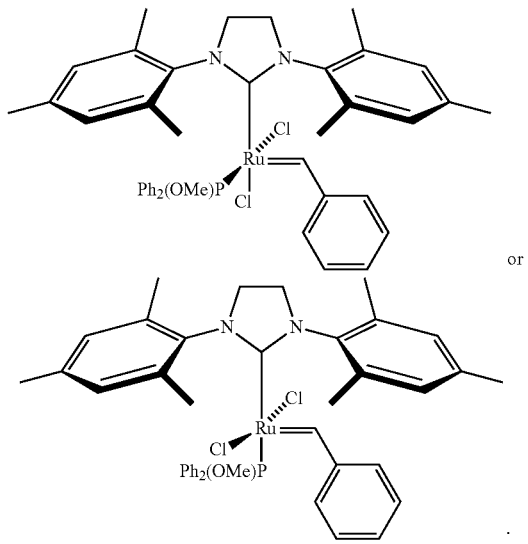

or

In one embodiment, the invention provides an article of manufacture, comprising at least one resin composition and at least one metal carbene olefin metathesis catalyst, wherein the resin composition comprises at least one cyclic olefin.

In one embodiment, the invention provides an article of manufacture, comprising at least one resin composition and at least one metal carbene olefin metathesis catalyst, wherein the resin composition comprises at least one cyclic olefin, with the proviso that the at least one metal carbene olefin metathesis catalyst is not

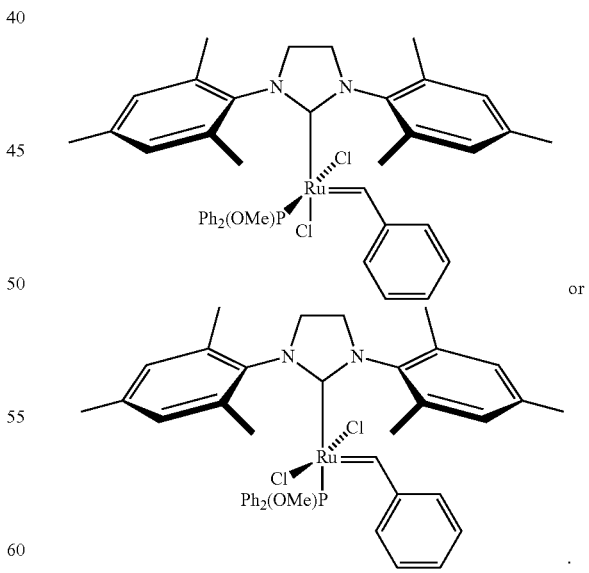

or

In one embodiment, the invention provides for use of at least one metal carbene olefin metathesis catalyst in a ROMP reaction.

In one embodiment, the invention provides for use of at least one metal carbene olefin metathesis catalyst in a ROMP reaction, with the proviso that the at least one metal carbene olefin metathesis catalyst is not

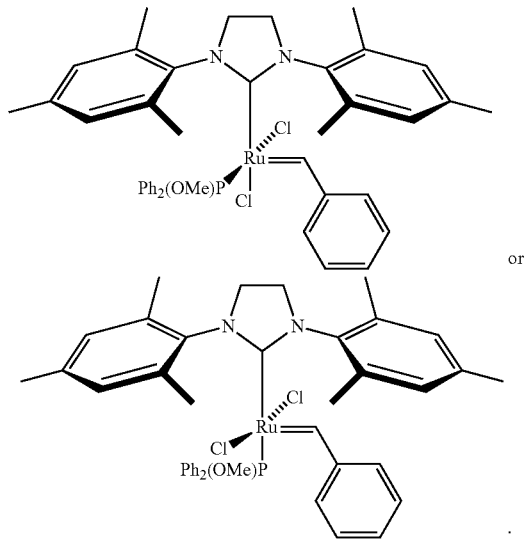

or

Other embodiments of the invention are described herein.

While the metal carbene olefin metathesis catalysts of the invention are of particular benefit for ring opening metathesis polymerization reactions, it may also find use with other metathesis reactions, such as a ring-opening cross metathesis reaction, a cross metathesis reaction, a ring-closing metathesis reaction, a self-metathesis reaction, an ethenolysis reaction, an alkenolysis reaction, or an acyclic diene metathesis polymerization reaction, as well as combinations of such metathesis reactions.

These and other aspects of the present invention will be apparent to the skilled artisan in light of the following detailed description and examples. Furthermore, it is to be understood that none of the embodiments or examples of the invention described herein are to be interpreted as being limiting.

DETAILED DESCRIPTION

Figure 1:
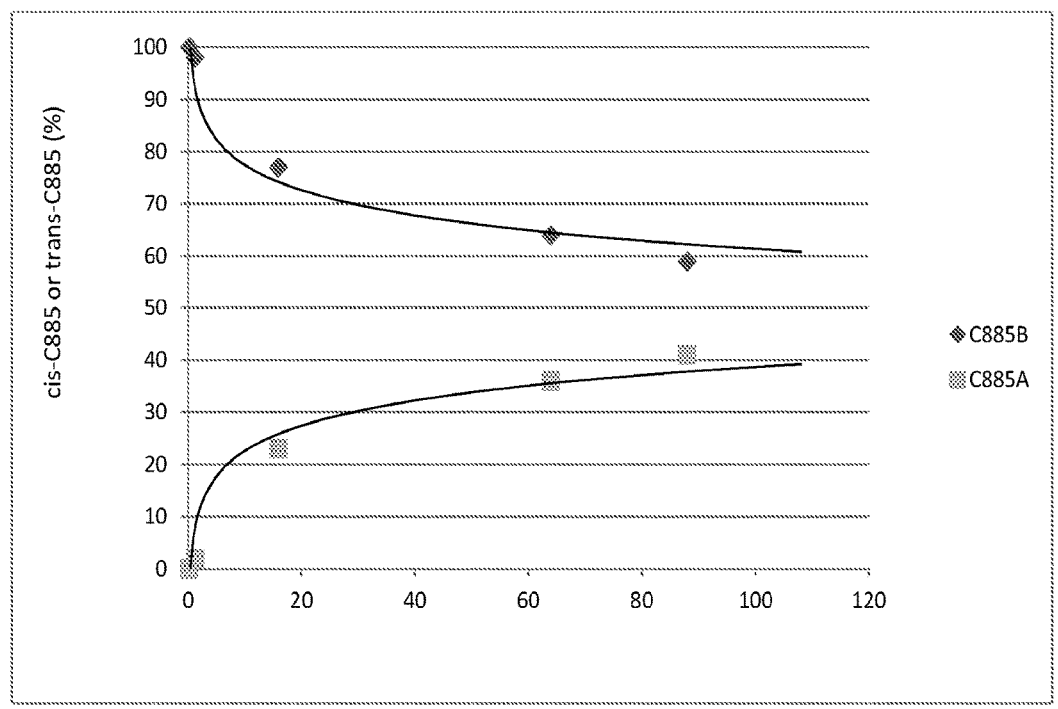
FIG. 1. Percentage of cis-C885 in solution of $CD_2Cl_2$ as compared to trans-C885.

Unless otherwise indicated, the invention is not limited to specific reactants, substituents, catalysts, reaction conditions, or the like, as such may vary. It is also to be understood that the terminology used herein is for the purpose of describing particular embodiments only and is not to be interpreted as being limited.

As used in the specification and the appended claims, the singular forms "a", "an," and "the" include plural referents unless the context clearly dictates otherwise. Thus, for example, reference to "an α-olefin" includes a single α-olefin as well as a combination or mixture of two or more α-olefins, reference to "a substituent" encompasses a single substituent as well as two or more substituents, and the like.

As used in the specification and the appended claims, the terms "for example," "for instance," "such as," or "includ-ing" are meant to introduce examples that further clarify more general subject matter. Unless otherwise specified, these examples are provided only as an aid for understanding the invention, and are not meant to be limiting in any fashion.

In this specification and in the claims that follow, reference will be made to a number of terms, which shall be defined to have the following meanings.

The term "alkyl" as used herein refers to a linear, branched, or cyclic saturated hydrocarbon group typically although not necessarily containing 1 to about 24 carbon atoms, preferably 1 to about 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 12 carbon atoms. The term "lower alkyl" refers to an alkyl group of 1 to 6 carbon atoms, and the specific term "cycloalkyl" refers to a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a divalent linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" refers to an alkenyl group of 2 to 6 carbon atoms, and the specific term "cycloalkenyl" refers to a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a divalent linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a divalent alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl (Ph), naphthyl, biphenyl, diphenylether, diphenylamine, benzophenone, and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or —(CO)-alkynyl wherein "alkyl," "aryl", "aralkyl", "alkaryl", "alkenyl", and "alkynyl" are as defined above. The acetoxy group (—O(CO)CH$_3$); often abbreviated as OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" and "halide" are used in the conventional sense to refer to a fluoro, chloro, bromo, or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

The term "heterocyclic carbene" refers to a neutral electron donor ligand comprising a carbene molecule, where the carbenic carbon atom is contained within a cyclic structure and where the cyclic structure also contains at least one heteroatom. Examples of heterocyclic carbenes include "N-heterocyclic carbenes" wherein the heteroatom is nitrogen and "P-heterocyclic carbenes" wherein the heteroatom is phosphorus.

By "substituted" as in "substituted hydrocarbyl," "substituted alkyl," "substituted aryl," and the like, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl)($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_1$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano (—C≡N), cyanato (—O—C≡N), thiocyanato (—S—C≡N), isocyanate (—N=C=O), thioisocyanate (—N=C=S), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino (—N($C_1$-$C_{24}$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CR=NH where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R includes without limitation hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R includes without limitation hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R includes without limitation alkyl or other hydrocarbyl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl," "functionalized alkyl," "functionalized olefin," "functionalized cyclic olefin," and the like, is meant that in the hydrocarbyl, alkyl, olefin, cyclic olefin, or other moiety, at least one hydrogen atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

The term "ROMP" refers to ring opening metathesis polymerization.

The term "substrate material" as used herein, is intended to generally mean any material that the resin compositions of the invention may be contacted with, applied to, or have the substrate material incorporated in to the resin. Without limitation, such materials include reinforcing materials, such as filaments, fibers, rovings, mats, weaves, fabrics, knitted material, cloth or other known structures, glass fibers and fabrics, carbon fibers and fabrics, aramid fibers and fabrics, and polyolefin or other polymer fibers or fabrics. Other suitable substrate materials include metallic density modulators, microparticulate density modulators, such as microspheres, glass microspheres, ceramic microspheres, microballons, cenospheres, and macroparticulate density modulators, such as glass or ceramic beads. A resin composition may comprise one substrate material or a mixture of different substrate materials.

Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "exotherm time" is defined herein as the amount of time that passes (i.e., the time difference) between the time point that a cyclic olefin is first contacted with a catalyst to form a ROMP composition and the time point that the temperature of the ROMP composition first increases by more than 1° C./second. The term "time to exotherm" and "exotherm time" have the same meaning and are used interchangeably herein. The peak exotherm temperature is the maximum temperature the ROMP composition reaches during the polymerization cycle. The exotherm peak time is defined as the amount of time that passes (i.e., the time difference) between the time point that a cyclic olefin is first contacted with a catalyst to form a ROMP composition and the time point that the ROMP composition reaches the peak exotherm temperature. As an alternative the exotherm time may also be defined as the amount of time that passes (i.e., the time difference) between the time point that a cyclic olefin is first contacted with a catalyst to form a ROMP composition and the time point that a propagating interface of the ROMP composition is first visually observed as the ROMP composition transitions from a liquid state (e.g., monomer state) or a gel state to a cured polymer state. The observation of the propagating interface is typically accompanied by an increase in temperature, often a large increase in temperature, of the ROMP composition. This increase in temperature may be measured by a thermocouple or similar temperature measuring and/or recording device.

Metal Carbene Olefin Metathesis Catalysts

In one embodiment, metal carbene olefin metathesis catalysts of the invention comprise a Group 8 transition metal complex having the structure of Formula (I):

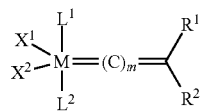

Formula (I)

wherein:
$L^1$ is a carbene ligand having the structure of Formula (II):

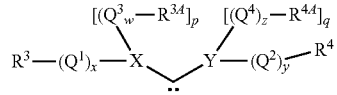

Formula (II)

M is a Group 8 transition metal, particularly Ruthenium or Osmium; more particularly Ruthenium;
X and Y are independently CH, C, N, O, S or P, preferably X and Y are both N;
$Q^1$, $Q^2$, $Q^3$, and $Q^4$ are independently linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, or, two or more substituents on adjacent atoms within $Q^1$, $Q^2$, $Q^3$, and $Q^4$ may be linked to form an additional cyclic group;
p and q are independently 0 or 1 or 2;
w, x, y, and z are independently 0 or 1, preferably w, x, y, and z are 0;
$R^3$, $R^{3A}$, $R^4$, and $R^{4A}$ are independently hydrogen, hydrocarbyl, substituted hydrocarbyl, heteroatom-containing hydrocarbyl, and substituted heteroatom-containing hydrocarbyl;
$L^2$ is a phosphinite or a phosphonite ligand;
$X^1$ and $X^2$ are independently anionic ligands and are bonded to M in a trans orientation or in a cis orientation;
m is 0, 1, or 2;
$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring);
and with the provisos:
p is 0 when X is O or S;
p is 1 when X is N, CH or P;
p is 2 when X is C;
q is 0 when Y is O or S;
q is 1 when Y is N, CH or P;
q is 2 when Y is C;
no more than one of X or Y is C or CH; and
the catalyst of Formula (I) is not of structures:

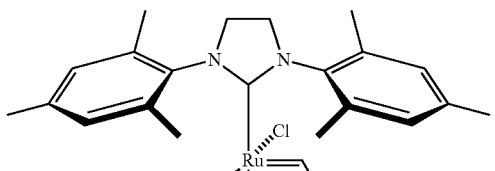

or

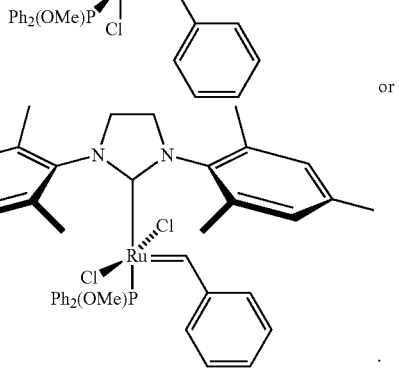

In one embodiment, $L^2$ is a phosphinite ligand represented by Formula (1):

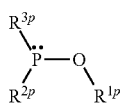

Formula (1)

$(R^{3p})(R^{2p})POR^{1p}$ wherein $R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl.

In another embodiment, $L^2$ is a phosphonite ligand represented by Formula (2):

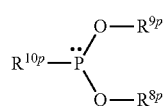

Formula (2)

$R^{10p}P(OR^{9p})(OR^{8p})$, wherein $R^{8p}$, $R^{9p}$, $R^{10p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl.

In a further embodiment, metal carbene olefin metathesis catalysts of the invention comprise a Group 8 transition metal complex having the structure of Formula (III):

Formula (III)

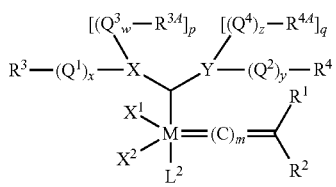

wherein:

M is a Group 8 transition metal, particularly Ruthenium or Osmium; more particularly Ruthenium;

X and Y are independently C, CH, N, O, S or P, preferably X and Y are both N;

$Q^1$, $Q^2$, $Q^3$, and $Q^4$ are independently linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, or, two or more substituents on adjacent atoms within $Q^1$, $Q^2$, $Q^3$, and $Q^4$ may be linked to form an additional cyclic group;

p and q are independently 0 or 1 or 2;

w, x, y, and z are independently 0 or 1, preferably w, x, y, and z are 0;

$R^3$, $R^{3A}$, $R^4$, and $R^{4A}$ are independently hydrogen, hydrocarbyl, substituted hydrocarbyl, heteroatom-containing hydrocarbyl, and substituted heteroatom-containing hydrocarbyl;

$L^2$ is a phosphinite or a phosphonite ligand;

$X^1$ and $X^2$ are independently anionic ligands and are bonded to M in a trans orientation or in a cis orientation;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and with the provisos:

p is 0 when X is O or S;

p is 1 when X is N or P;

p is 2 when X is C;

q is 0 when Y is O or S;

q is 1 when Y is N, CH or P;

q is 2 when Y is C:

no more than one of X or Y is C or CH; and the catalyst of Formula (III) is not of structures:

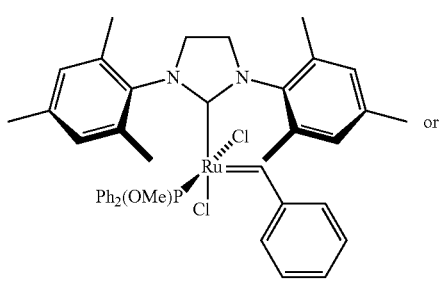

or

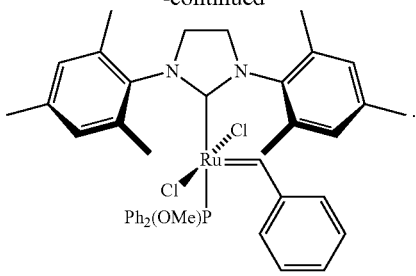

In one embodiment metal carbene olefin metathesis catalysts of the invention are represented by the structure of Formula (IIIa):

Formula (IIIa)

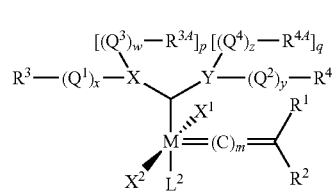

where M, $L^2$, p, q, m, w, x, y, z, $R^1$, $R^2$, $R^3$, $R^4$, X, Y, $R^{3A}$, $R^{4A}$, $X^1$, $X^2$, $Q^1$, $Q^2$, $Q^3$, $Q^4$ are as defined above for a complex having the structure of Formula (III); and wherein the complex is a positional isomer, wherein $X^1$ and $X^2$ are bonded to M in a trans orientation; and with the proviso that the catalyst of Formula (IIIa) is not of structure:

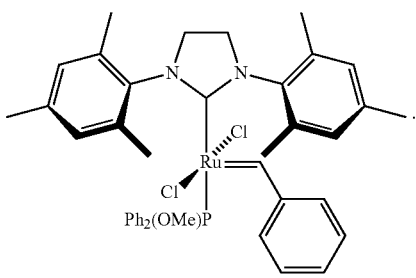

In one embodiment metal carbene olefin metathesis catalysts of the invention are represented by the structure of Formula (IIIb):

Formula (IIIb)

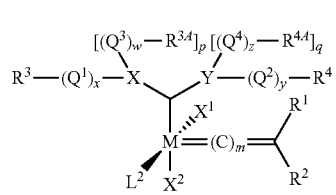

where M, $L^2$, p, q, m, w, x, y, z, $R^1$, $R^2$, $R^3$, $R^4$, X, Y, $R^{3A}$, $R^{4A}$, $X^1$, $X^2$, $Q^1$, $Q^2$, $Q^3$, $Q^4$ are as defined above for a complex having the structure of Formula (III); and wherein the complex is a positional isomer, wherein $X^1$ and $X^2$ are bonded to M in a cis orientation; and with the proviso that the catalyst of Formula (IIIb) is not of structure:

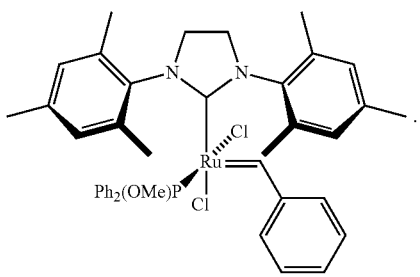

A particular class of carbene ligands having the structure of Formula (II), where $R^{3,4}$ and $R^{4,4}$ are linked to form a cyclic group and at least one of X or Y is a nitrogen, or at least one of $Q^3$ or $Q^4$ is a heteroatom-containing hydrocarbylene or substituted heteroatom-containing hydrocarbylene, where at least one heteroatom is a nitrogen, are commonly referred to as N-heterocyclic carbene (NHC) ligands.

Preferably, $R^{3,4}$ and $R^{4,4}$ are linked to form a cyclic group so that the carbene ligand $L^1$, has the structure of Formula (IV):

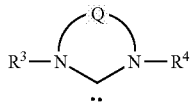

Formula (IV)

wherein: at least one of $R^3$ and $R^4$, or both, $R^3$ and $R^4$, are alicyclic or aromatic of one to about five rings, and optionally containing one or more heteroatoms and/or substituents; Q is a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups, Q is often, although not necessarily, a two-atom linkage or a three-atom linkage.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are 2,4,6-trimethylphenyl (i.e., mesityl or Mes as defined herein). As another example, $R^3$ and $R^4$ are 2,6-diisopropylphenyl (i.e., DIPP or DiPP as defined herein).

Examples of N-heterocyclic carbene (NHC) ligands and acyclic diaminocarbene ligands suitable as $L^1$ thus include, but are not limited to the following, where DIPP or DiPP is 2,6-diisopropylphenyl and Mes is 2,4,6-trimethylphenyl:

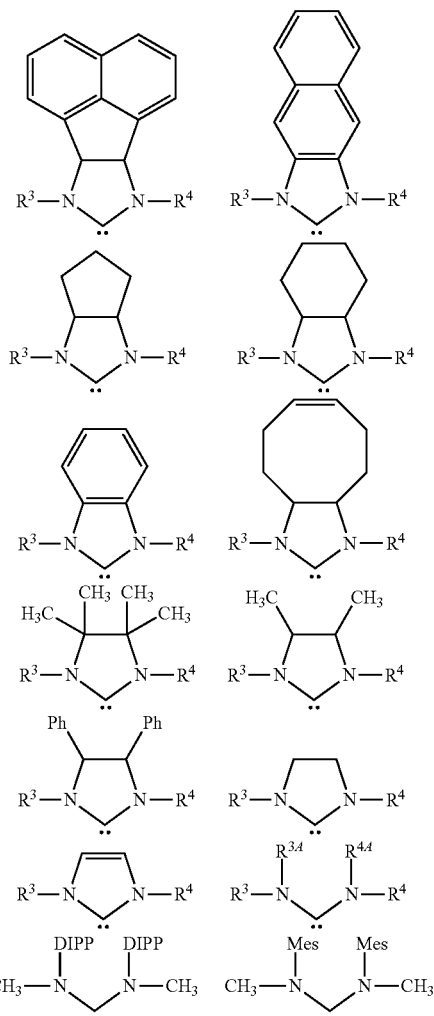

An additional example of an N-heterocyclic carbene (NHC) ligand suitable as $L^1$ includes 1,3-Bis(2,4,6-trimethylphenyl)-2-imidazolidinylidene) (i.e., sIMes):

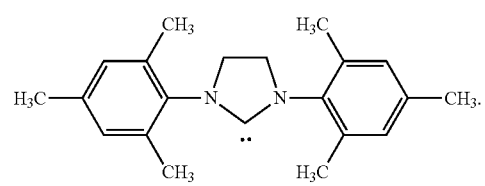

An additional example of an N-heterocyclic carbene (NHC) ligand suitable as $L^1$ includes 1,3-Bis(2,4,6-trimethylphenyl)imidazol-2-ylidene) (i.e., IMes):

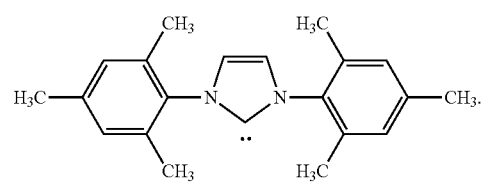

Additional examples of N-heterocyclic carbene (NHC) ligands and acyclic diaminocarbene ligands suitable as $L^1$ thus include, but are not limited to the following:

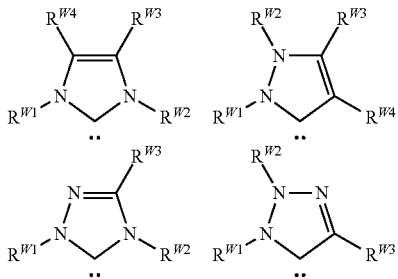

wherein: $R^{W1}$, $R^{W2}$, $R^{W3}$, $R^{W4}$ are independently hydrogen, unsubstituted hydrocarbyl, substituted hydrocarbyl, or heteroatom containing hydrocarbyl, and where one or both of $R^{W3}$ and $R^{W4}$ may be independently selected from halogen, nitro, amido, carboxyl, alkoxy, aryloxy, sulfonyl, carbonyl, thio, or nitroso groups. Additional examples of N-heterocyclic carbene (NHC) ligands suitable as $L^1$ are further described in U.S. Pat. Nos. 7,378,528; 7,652,145; 7,294,717; 6,787,620; 6,635,768; and 6,552,139, the contents of each are incorporated herein by reference. Moreover, thermally activated N-Heterocyclic Carbene Precursors as disclosed in U.S. Pat. No. 6,838,489, the contents of which are incorporated herein by reference, may also be used with the present invention.

When $R^3$ and $R^4$ are aromatic, they are typically although not necessarily composed of one or two aromatic rings, which may or may not be substituted, e.g., $R^3$ and $R^4$ may be phenyl, substituted phenyl, biphenyl, substituted biphenyl, or the like. In one preferred embodiment, $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Preferably, any substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ are 2,4,6-trimethylphenyl; and as another example, $R^3$ and $R^4$ are 2,6-diisopropylphenyl.

In another embodiment, $L^2$ is a phosphinite ligand represented by Formula (1): $(R^{3p})(R^{2p})POR^{1p}$ wherein: $R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl.

In one example, $R^{1p}$ is selected from methyl (—CH$_3$), ethyl (—CH$_2$CH$_3$), isopropyl (—CH(CH$_3$)$_2$), n-butyl (—CH$_2$CH$_2$CH$_2$CH$_3$), sec-butyl (—CH(CH$_3$)(CH$_2$CH$_3$)), tert-butyl (—C(CH$_3$)$_3$), 4-methoxyphenyl (—(C$_6$H$_4$)(para-OCH$_3$), benzyl (—CH$_2$C$_6$H$_5$), or phenyl (—C$_6$H$_5$); and $R^{2p}$ and $R^{3p}$ are each phenyl (—C$_6$H$_5$). In another example, $R^{1p}$ is selected from methyl (—CH$_3$), ethyl (—CH$_2$CH$_3$), isopropyl (—CH(CH$_3$)$_2$), 4-methoxyphenyl (—(C$_6$H$_4$)(para-OCH$_3$), or phenyl (—C$_6$H$_5$); and $R^{2p}$ and $R^{3p}$ are each phenyl (—C$_6$H$_5$). In another example, $R^{1p}$ is selected from methyl (—CH$_3$), ethyl (—CH$_2$CH$_3$), isopropyl (—CH(CH$_3$)$_2$), or phenyl (—C$_6$H$_5$); and $R^{2p}$ and $R^{3p}$ are each phenyl (—C$_6$H$_5$). In another example, $R^{1p}$ is selected from methyl (—CH$_3$), isopropyl (—CH(CH$_3$)$_2$), or phenyl (—C$_6$H$_5$); and $R^{2p}$ and $R^{3p}$ are each phenyl (—C$_6$H$_5$). In another example, $R^{1p}$ is selected from methyl (—CH$_3$), ethyl (—CH$_2$CH$_3$), or isopropyl (—CH(CH$_3$)$_2$); and $R^{2p}$ and $R^{3p}$ are each phenyl (—C$_6$H$_5$). In another example, $R^{1p}$ is phenyl (—C$_6$H$_5$); and $R^{2p}$ and $R^{3p}$ are each phenyl (—C$_6$H$_5$).

In another embodiment, $L^2$ is a phosphonite ligand represented by Formula (2): $R^{10p}P(OR^{9p})(OR^{8p})$, wherein: $R^{8p}$, $R^{9p}$, $R^{10p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl.

In one example, $R^{8p}$ and $R^{9p}$ are each independently selected from methyl, ethyl, isopropyl, n-butyl, sec-butyl, tert-butyl, 4-methoxyphenyl, benzyl, or phenyl; and $R^{10p}$ is phenyl. In another example, $R^{8p}$ and $R^{9p}$ are each methyl, ethyl, isopropyl, n-butyl, sec-butyl, tert-butyl, 4-methoxyphenyl, benzyl, or phenyl; and $R^{10p}$ is phenyl. In another example, $R^{8p}$ and $R^{9p}$ are each methyl, ethyl, isopropyl, or phenyl; and $R^{10p}$ is phenyl. In another example, $R^{8p}$ and $R^{9p}$ are each methyl, isopropyl, or phenyl; and $R^{10p}$ is phenyl. In another example, $R^{8p}$ and $R^{9p}$ are each methyl, or isopropyl; and $R^{10p}$ is phenyl. In another example, $R^{8p}$ and $R^{9p}$ are each phenyl; and $R^{10p}$ is phenyl.

In certain embodiments, $R^1$ and $R^2$ are independently selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group will contain 4 to 12, preferably 5, 6, 7, or 8 ring atoms.

In preferred catalysts, $R^1$ is hydrogen and $R^2$ is selected from $C_1$-$C_{20}$ alkyl, $C_2$-$C_{20}$ alkenyl, and $C_5$-$C_{24}$ aryl, more preferably $C_1$-$C_6$ alkyl, $C_2$-$C_6$ alkenyl, and $C_5$-$C_{14}$ aryl. Still more preferably, $R^2$ is phenyl, vinyl, methyl, isopropyl, or t-butyl, optionally substituted with one or more moieties selected from $C_1$-$C_6$ alkyl, $C_1$-$C_6$ alkoxy, phenyl, and a functional group Fn as defined earlier herein. Most preferably, $R^2$ is phenyl or vinyl substituted with one or more moieties selected from methyl, ethyl, chloro, bromo, iodo, fluoro, nitro, dimethylamino, methyl, methoxy, and phenyl. Optimally, $R^2$ is phenyl or —CH=C(CH$_3$)$_2$. Furthermore, $R^1$ and $R^2$ may be taken together to form an indenylidene moiety, preferably phenylindenylidene.

In certain embodiments, $X^1$ and $X^2$ are anionic ligands, and may be the same or different, or are linked together to form a cyclic group, typically although not necessarily a five- to eight-membered ring. In preferred embodiments, $X^1$ and $X^2$ are each independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, NO$_3$, —N=C=O, —N=C=S, or $C_5$-$C_{24}$ arylsulfinyl. Optionally, $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. In more preferred embodiments, $X^1$ and $X^2$ are halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. In even more preferred embodiments, $X^1$ and $X^2$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. In the most preferred embodiments, $X^1$ and $X^2$ are each chloride.

In another embodiment, metal carbene olefin metathesis catalysts of the invention are represented by the structure of Formula (V):

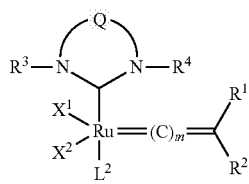

Formula (V)

wherein
Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers;
$R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;
$X^1$ and $X^2$ are independently halogen; and are bonded to Ru in a trans orientation or in a cis orientation;
$L^2$ is a phosphinite or a phosphonite ligand;
m is 0, 1, or 2;
$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and the catalyst of Formula (V) is not of structures:

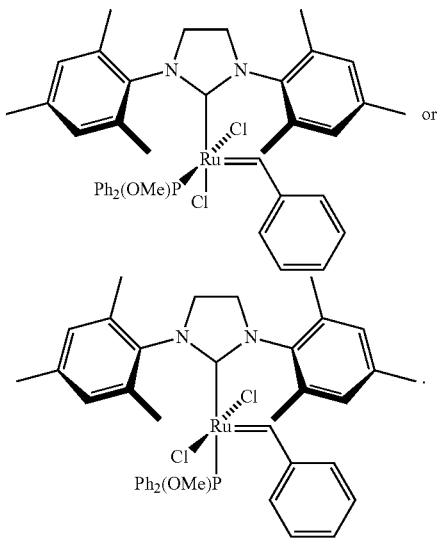

In another embodiment, metal carbene olefin metathesis catalysts of the invention are represented by the structure of Formula (V): wherein Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers; $R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;
$X^1$ and $X^2$ are independently halogen; and are bonded to Ru in a trans orientation;
$L^2$ is a phosphinite or a phosphonite ligand;
m is 0, 1, or 2;
$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and
the catalyst of Formula (V) is not of structure:

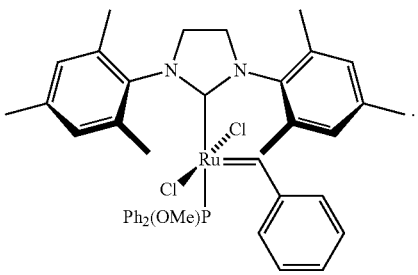

In another embodiment, metal carbene olefin metathesis catalysts of the invention are represented by the structure of Formula (V):
m is 0;
Q is a two-atom linkage having the structure —$CR^{11}R^{12}$—$CR^{13}R^{14}$—, wherein $R^{11}$, $R^{12}$, $R^{13}$, and $R^{14}$ are independently hydrogen;
$R^3$ and $R^4$ are each phenyl substituted with up to three substituents selected from methyl or isopropyl;
$X^1$ and $X^2$ are Cl; and are bonded to Ru in a trans orientation;
$L^2$ is a phosphinite ligand;
$R^1$ is hydrogen, $R^2$ is phenyl, vinyl, optionally substituted with one or more moieties selected from $C_1$-$C_6$ alkyl, or $C_1$-$C_6$ alkoxy; or $R^1$ and $R^2$ may be linked together to form a phenylindenylidene;
and the catalyst of Formula (V) is not of structure:

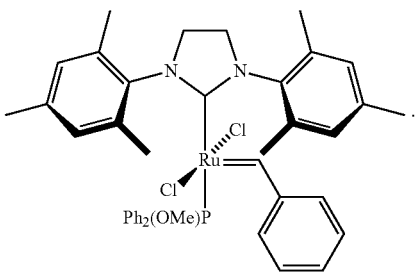

In another embodiment, metal carbene olefin metathesis catalysts of the invention are represented by the structure of Formula (V):
m is 0;
Q is a two-atom linkage having the structure —$CR^{11}R^{12}$—$CR^{13}R^{14}$—, wherein $R^{11}$, $R^{12}$, $R^{13}$, and $R^{14}$ are independently hydrogen;
$R^3$ and $R^4$ are each phenyl substituted with up to three substituents selected from methyl or isopropyl;
$X^1$ and $X^2$ are Cl; and are bonded to Ru in a trans orientation;
$L^2$ is a phosphonite ligand;
$R^1$ is hydrogen, $R^2$ is phenyl, vinyl, optionally substituted with one or more moieties selected from $C_1$-$C_6$ alkyl, or $C_1$-$C_6$ alkoxy; or $R^1$ and $R^2$ may be linked together to form a phenylindenylidene.

In another embodiment, metal carbene olefin metathesis catalysts of the invention are represented by the structure of Formula (V):
Q is a two-atom linkage having the structure —$CR^{11}R^{12}$—$CR^{13}R^{14}$—, wherein $R^{11}$, $R^{12}$, $R^{13}$, and $R^{14}$ are independently hydrogen;

$R^3$ and $R^4$ are each phenyl substituted with up to three substituents selected from methyl or isopropyl;
$X^1$ and $X^2$ are Cl; and are bonded to Ru in a trans orientation;
$L^2$ is a phosphinite or a phosphonite ligand;
m is 0;
$R^1$ is hydrogen, $R^2$ is phenyl, phenyl-o-isopropyl —CH=CH(tert-butyl) or —CH=C(CH$_3$)$_2$; or $R^1$ and $R^2$ may be linked together to form a phenylindenylidene; and
the catalyst of Formula (V) is not of structure:

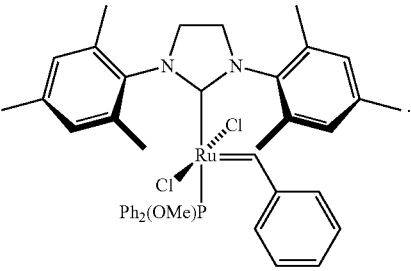

In another embodiment, metal carbene olefin metathesis catalysts of the invention are represented by the structure of Formula (V): wherein Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^1$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers; $R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;
$X^1$ and $X^2$ are independently halogen; and are bonded to Ru in a cis orientation;
$L^2$ is a phosphinite or a phosphonite ligand;
m is 0, 1, or 2;
$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and
the catalyst of Formula (V) is not of structure:

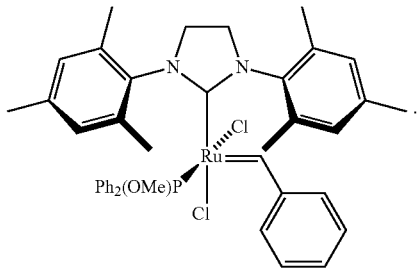

In one embodiment metal carbene olefin metathesis catalysts of the invention are represented by the structure of Formula (Va):

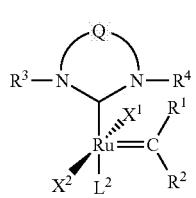

Formula (Va)

wherein
Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers;
$R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;

$X^1$ and $X^2$ are independently halogen; and are bonded to Ru in a trans orientation;
$L^2$ is a phosphinite or a phosphonite ligand;
m is 0, 1, or 2;
$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and with the proviso that the catalyst of Formula (Va) is not of structure:

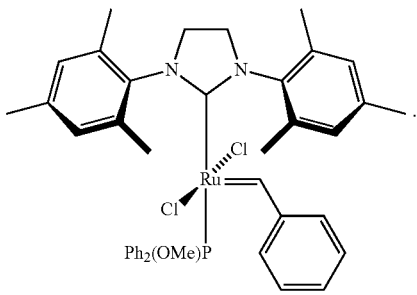

In one embodiment metal carbene olefin metathesis catalysts of the invention are represented by the structure of Formula (Va):
where $L^2$, $R^1$, $R^2$, $X^1$ and $X^2$ are as defined above for a complex having the structure of Formula (V); Q, $R^3$ and $R^4$ are as defined above for an N-heterocyclic carbene (NHC) ligand having the structure of Formula (IV) or Formula (V); and wherein the complex is a positional isomer, wherein $X^1$ and $X^2$ are bonded to Ru in a trans orientation; and with the proviso that the catalyst of Formula (Va) is not of structure:

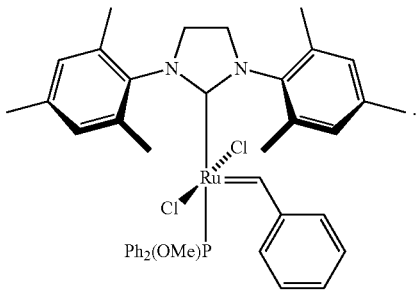

In one embodiment metal carbene olefin metathesis catalysts of the invention are represented by the structure of Formula (Vb):

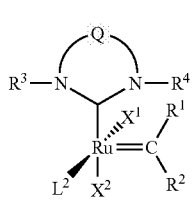

Formula (Vb)

wherein

Q is a two-atom linkage having the structure —$CR^{11}R^{12}$—$CR^{13}R^{14}$— or —$CR^{11}$=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers;

$R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;

$X^1$ and $X^2$ are independently halogen; and are bonded to Ru in a cis orientation;

$L^2$ is a phosphinite or a phosphonite ligand;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and with the proviso that the catalyst of Formula (Vb) is not of structure:

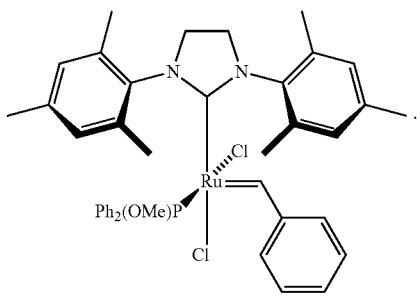

In one embodiment metal carbene olefin metathesis catalysts of the invention are represented by the structure of Formula (Vb):

where $L^2$, $R^1$, $R^2$, $X^1$ and $X^2$ are as defined above for a complex having the structure of Formula (V); Q, $R^3$ and $R^4$ are as defined above for an N-heterocyclic carbene (NHC) ligand having the structure of Formula (IV) or Formula (V); and wherein the complex is a positional isomer, wherein $X^1$ and $X^2$ are bonded to Ru in a cis orientation; and with the proviso that the catalyst of Formula (Vb) is not of structure:

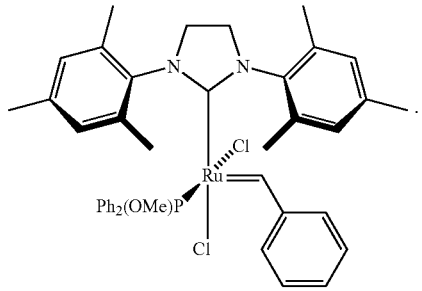

In certain embodiments, metal carbene olefin metathesis catalysts of the invention are represented by the structure of Formula (VI):

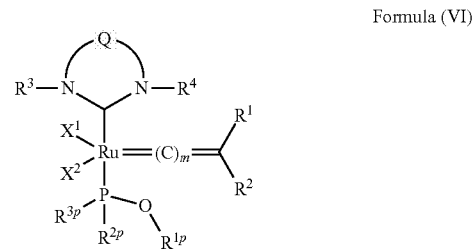

Formula (VI)

wherein: Q is a two-atom linkage having the structure —$CR^{11}R^{12}$—$CR^{13}R^{14}$— or —CR=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers;

$R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;

$X^1$ and $X^2$ are independently halogen; and are bonded to Ru in a trans orientation or in a cis orientation;

$R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and the catalyst of Formula (VI) is not of structures:

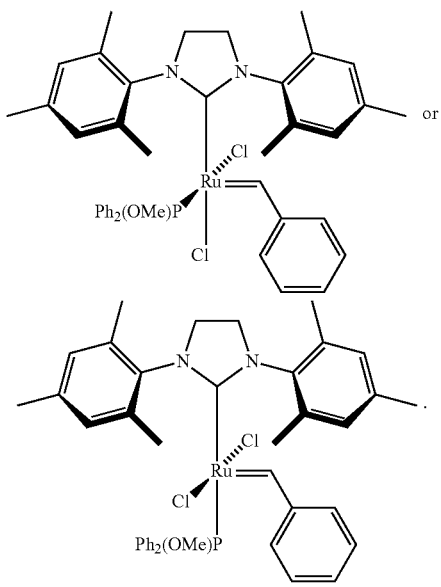

or

In certain embodiments, metal carbene olefin metathesis catalysts of the invention are represented by the structure of Formula (VI):

wherein: Q is a two-atom linkage having the structure —$CR^{11}R^{12}$—$CR^{13}R^{14}$— wherein $R^{11}$, $R^{12}$, $R^{13}$, and $R^{14}$ are independently hydrogen;

$R^3$ and $R^4$ are the same and are phenyl, wherein each phenyl is substituted with up to three substituents selected from $C_1$-$C_{20}$ alkyl;

$X^1$ and $X^2$ are independently halogen; and are bonded to Ru in a trans orientation;

$R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl;

m is 0 or 1;

$R^1$ is hydrogen, and $R^2$ is phenyl, —CH=CH(tert-butyl) or —CH=C(CH$_3$)$_2$, or $R^1$ and $R^2$ may be taken together to form an indenylidene moiety, preferably phenylindenylidene; and the catalyst of Formula (VI) is not of structure:

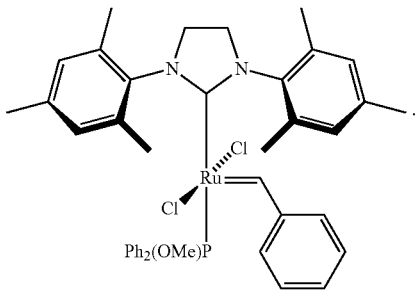

In certain embodiments, metal carbene olefin metathesis catalysts of the invention are represented by the structure of Formula (VI):

wherein: Q is a two-atom linkage having the structure —$CR^{11}R^{12}$—$CR^{13}R^{14}$— wherein $R^{11}$, $R^{12}$, $R^{13}$, and $R^{14}$ are independently hydrogen;

$R^3$ and $R^4$ are the same and are phenyl, wherein each phenyl is substituted with up to three substituents selected from $C_1$-$C_{20}$ alkyl;

$X^1$ and $X^2$ are independently halogen; and are bonded to Ru in a trans orientation;

$R^{1p}$, $R^{2p}$, $R^{3p}$ are each independently methyl, ethyl, isopropyl, n-butyl, sec-butyl, tert-butyl, 4-methoxyphenyl, benzyl or phenyl;

m is 0 or 1;

$R^1$ is hydrogen, and $R^2$ is phenyl, —CH=CH(tert-butyl) or —CH=C(CH$_3$)$_2$, or $R^1$ and $R^2$ may be taken together to form an indenylidene moiety, preferably phenylindenylidene; and the catalyst of Formula (VI) is not of structure:

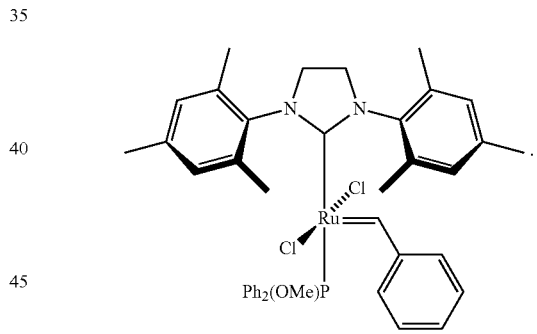

In certain embodiments, metal carbene olefin metathesis catalysts of the invention are represented by the structure of Formula (VI):

wherein: Q is a two-atom linkage having the structure —$CR^{11}R^{12}$—$CR^{13}R^{14}$— wherein $R^{11}$, $R^{12}$, $R^{13}$, and $R^{14}$ are independently hydrogen;

$R^3$ and $R^4$ are the same and are phenyl, wherein, each phenyl is substituted with up to three substituents selected from $C_1$-$C_{20}$ alkyl;

$X^1$ and $X^2$ are independently chloride; and are bonded to Ru in a trans orientation;

$R^{1p}$ is methyl, ethyl, isopropyl or phenyl;

$R^{2p}$ is phenyl;

$R^{3p}$ is phenyl;

m is 0 or 1;

$R^1$ is hydrogen, and $R^2$ is phenyl, —CH=CH(tert-butyl) or —CH=C(CH$_3$)$_2$, or $R^1$ and $R^2$ may be taken together to form an indenylidene moiety, preferably phenylindenylidene; and the catalyst of Formula (VI) is not of structure:

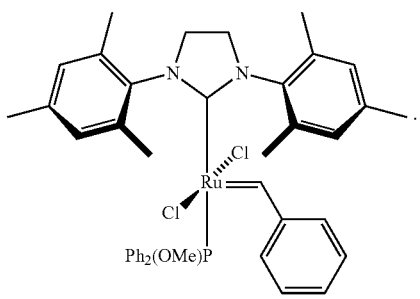

In certain embodiments, metal carbene olefin metathesis catalysts of the invention are represented by the structure of Formula (VI):
wherein: Q is a two-atom linkage having the structure —$CR^{11}R^{12}$—$CR^{13}R^{14}$— wherein $R^{11}$, $R^{12}$, $R^{13}$, and $R^{14}$ are independently hydrogen;
$R^3$ and $R^4$ are the same and are phenyl, wherein each phenyl is substituted with up to three substituents selected from $C_1$-$C_{20}$ alkyl;
$X^1$ and $X^2$ are independently halogen; and are bonded to Ru in a cis orientation;
$R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl;
m is 0 or 1;
$R^1$ is hydrogen, and $R^2$ is phenyl, —CH=CH(tert-butyl) or —CH=C(CH$_3$)$_2$, or $R^1$ and $R^2$ may be taken together to form an indenylidene moiety, preferably phenylindenylidene; and
the catalyst of Formula (VI) is not of structure:

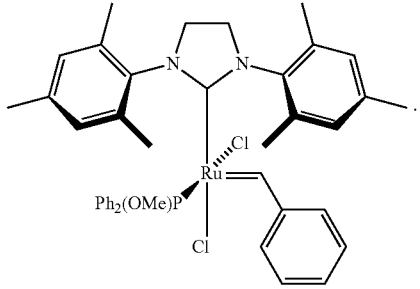

In certain embodiments, metal carbene olefin metathesis catalysts of the invention are represented by the structure of Formula (VI):
wherein: Q is a two-atom linkage having the structure —$CR^{11}R^{12}$—$CR^{13}R^{14}$— wherein $R^{11}$, $R^{12}$, $R^{13}$, and $R^{14}$ are independently hydrogen;
$R^3$ and $R^4$ are the same and are phenyl, and each phenyl is substituted with up to three substituents selected from $C_1$-$C_{20}$ alkyl;
$X^1$ and $X^2$ are independently halogen; and are bonded to Ru in a cis orientation;
$R^{1p}$, $R^{2p}$, $R^{3p}$ are each independently methyl, ethyl, isopropyl, n-butyl, sec-butyl, tert-butyl, 4-methoxyphenyl, benzyl or phenyl;
m is 0 or 1;
$R^1$ is hydrogen, and $R^2$ is phenyl, —CH=CH(tert-butyl) or —CH=C(CH$_3$)$_2$, or $R^1$ and $R^2$ may be taken together to form an indenylidene moiety, preferably phenylindenylidene; and the catalyst of Formula (VI) is not of structure:

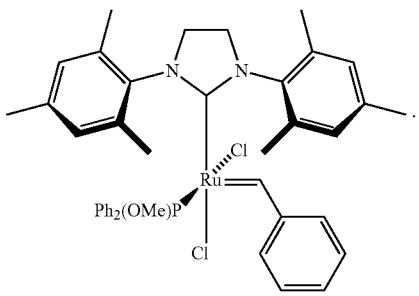

In certain embodiments, metal carbene olefin metathesis catalysts of the invention are represented by the structure of Formula (VI):
wherein: Q is a two-atom linkage having the structure —$CR^{11}R^{12}$—$CR^{13}R^{14}$— wherein $R^{11}$, $R^{12}$, $R^{13}$, and $R^{14}$ are independently hydrogen;
$R^3$ and $R^4$ are the same and are phenyl, wherein each phenyl is substituted with up to three substituents selected from $C_1$-$C_{20}$ alkyl;
$X^1$ and $X^2$ are chloride; and are bonded to Ru in a cis orientation;
$R^{1p}$ is methyl, isopropyl or phenyl;
$R^{2p}$ is phenyl;
$R^{3p}$ is phenyl;
m is 0 or 1;
$R^1$ is hydrogen, and $R^2$ is phenyl, —CH=CH(tert-butyl) or —CH=C(CH$_3$)$_2$, or $R^1$ and $R^2$ may be taken together to form an indenylidene moiety, preferably phenylindenylidene; and
the catalyst of Formula (VI) is not of structure:

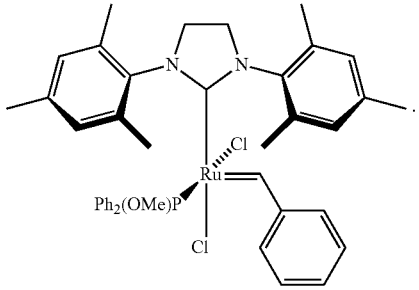

In one embodiment metal carbene olefin metathesis catalysts of the invention are represented by the structure of Formula (VIa):

Formula (VIa)

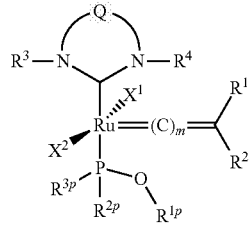

wherein: Q is a two-atom linkage having the structure —$CR^{11}R^{12}$—$CR^{13}R^{14}$— or —CR=$CR^{13}$—, preferably —CR$^{11}$R$^{12}$—CR$^{13}$R$^{14}$—, wherein R$^{11}$, R$^{12}$, R$^{13}$, and R$^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, C$_1$-C$_{12}$ alkyl, substituted C$_1$-C$_{12}$ alkyl, C$_1$-C$_{12}$ heteroalkyl, substituted C$_1$-C$_{12}$ heteroalkyl, phenyl, or substituted phenyl, alternatively, any two of R$^{11}$, R$^{12}$, R$^{13}$, and R$^{14}$ may be linked together to form a substituted or unsubstituted, saturated or unsaturated ring structure; e.g., a C$_4$-C$_{12}$ alicyclic group or a C$_5$ or C$_6$ aryl group, which may itself be substituted, e.g., with linked or fused alicyclic or aromatic groups, or with other substituents, or any one or more of R$^{11}$, R$^{12}$, R$^{13}$, and R$^{14}$ comprises one or more of the linkers;

R$^3$ and R$^4$ may be unsubstituted phenyl or phenyl substituted with one or more substituents such as C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, C$_6$-C$_{24}$ aralkyl, C$_6$-C$_{24}$ alkaryl, or halide, or are aromatic, they are typically although not necessarily, composed of one or two aromatic rings, which may or may not be substituted, e.g., R$^3$ and R$^4$ may be phenyl, substituted phenyl, biphenyl, substituted biphenyl, or the like, preferably R$^3$ and R$^4$ are the same and are each unsubstituted phenyl or phenyl substituted with up to three substituents selected from C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, C$_6$-C$_{24}$ aralkyl, C$_6$-C$_{24}$ alkaryl, and halide, preferred substituents present are hydrogen, C$_1$-C$_{12}$ alkyl, C$_1$-C$_{12}$ alkoxy, C$_5$-C$_{14}$ aryl, substituted C$_5$-C$_{14}$ aryl, or halide;

X$^1$ and X$^2$ are independently halogen; and are bonded to Ru in a trans orientation;

R$^{1p}$, R$^{2p}$, R$^{3p}$ are each independently substituted or unsubstituted C$_6$-C$_{10}$ aryl, or substituted or unsubstituted C$_1$-C$_{10}$ alkyl, or substituted or unsubstituted C$_3$-C$_8$ cycloalkyl;

m is 0, 1, or 2;

R$^1$ and R$^2$ are independently hydrogen, hydrocarbyl, substituted hydrocarbyl, heteroatom-containing hydrocarbyl, substituted heteroatom-containing hydrocarbyl, or functional groups, or R$^1$ and R$^2$ may be linked together to form a ring (for example C$_4$-C$_{10}$ ring, or C$_5$-C$_6$ ring) that may be substituted or unsubstituted, saturated or unsaturated and may be fused or linked to a further ring (for example a C$_4$-C$_{10}$ ring or a C$_5$-C$_6$ ring); and the catalyst of Formula (VIa) is not of structure:

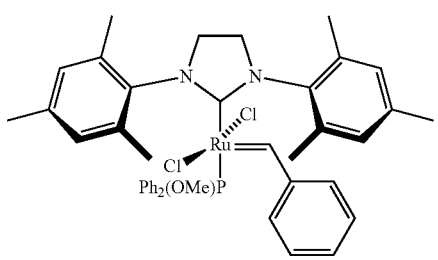

In one embodiment metal carbene olefin metathesis catalysts of the invention are represented by the structure of Formula (VIa):

where R$^1$, R$^2$, R$^3$, R$^4$, X$^1$, X$^2$, m, R$^{1p}$, R$^{2p}$, R$^{3p}$, and Q are as defined above for a complex having the structure of Formula (VI); and wherein the complex is a positional isomer, wherein X$^1$ and X$^2$ are bonded to Ru in a trans orientation; and with the proviso that the catalyst of Formula (VIa) is not of structure:

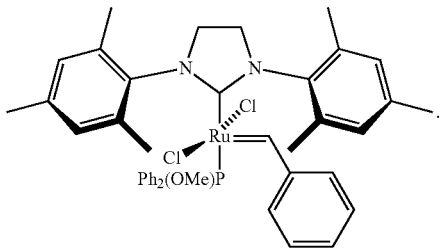

In one embodiment metal carbene olefin metathesis catalysts of the invention are represented by the structure of Formula (VIb):

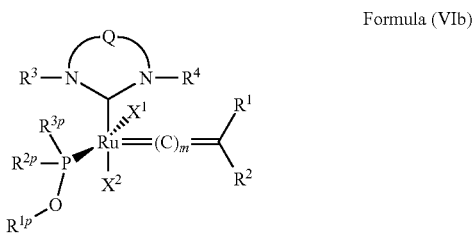

Formula (VIb)

wherein: Q is a two-atom linkage having the structure —CR$^{11}$R$^{12}$—CR$^{13}$R$^{14}$— or —CR=CR$^{13}$—, preferably —CR$^{11}$R$^{12}$—CR$^{13}$R$^{14}$—, wherein R$^{11}$, R$^{12}$, R$^{13}$, and R$^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, C$_1$-C$_{12}$ alkyl, substituted C$_1$-C$_{12}$ alkyl, C$_1$-C$_{12}$ heteroalkyl, substituted C$_1$-C$_{12}$ heteroalkyl, phenyl, or substituted phenyl, alternatively, any two of R$^{11}$, R$^{12}$, R$^{13}$, and R$^{14}$ may be linked together to form a substituted or unsubstituted, saturated or unsaturated ring structure; e.g., a C$_4$-C$_{12}$ alicyclic group or a C$_5$ or C$_6$ aryl group, which may itself be substituted, e.g., with linked or fused alicyclic or aromatic groups, or with other substituents, or any one or more of R$^{11}$, R$^{12}$, R$^{13}$, and R$^{14}$ comprises one or more of the linkers;

R$^3$ and R$^4$ may be unsubstituted phenyl or phenyl substituted with one or more substituents such as C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, C$_6$-C$_{24}$ aralkyl, C$_6$-C$_{24}$ alkaryl, or halide, or are aromatic, they are typically although not necessarily, composed of one or two aromatic rings, which may or may not be substituted, e.g., R$^3$ and R$^4$ may be phenyl, substituted phenyl, biphenyl, substituted biphenyl, or the like, preferably R$^3$ and R$^4$ are the same and are each unsubstituted phenyl or phenyl substituted with up to three substituents selected from C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, C$_6$-C$_{24}$ aralkyl, C$_6$-C$_{24}$ alkaryl, and halide, preferred substituents present are hydrogen, C$_1$-C$_{12}$ alkyl, C$_1$-C$_{12}$ alkoxy, C$_5$-C$_{14}$ aryl, substituted C$_5$-C$_{14}$ aryl, or halide;

X$^1$ and X$^2$ are independently halogen; and are bonded to Ru in a cis orientation;

$R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring); and the catalyst of Formula (VIb) is not of structure:

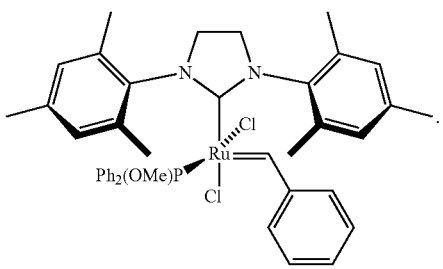

In one embodiment metal carbene olefin metathesis catalysts of the invention are represented by the structure of Formula (VIb):

where $R^1$, $R^2$, $R^3$, $R^4$, $X^1X^2$, m, $R^{1p}$, $R^{2p}$, $R^{3p}$, and Q are as defined above for a complex having the structure of Formula (VI); and wherein the complex is a positional isomer, wherein $X^1$ and $X^2$ are bonded to Ru in a cis orientation; and with the proviso that the catalyst of Formula (VIb) is not of structure:

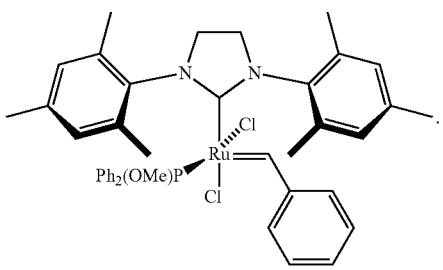

In certain embodiments, metal carbene olefin metathesis catalysts of the invention are represented by the structure of Formula (VII):

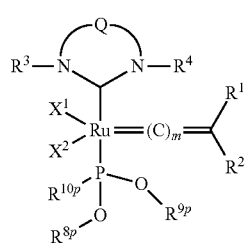

Formula (VII)

wherein: Q is a two-atom linkage having the structure —$CR^{11}R^{12}$—$CR^{13}R^{14}$— or —CR=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers;

$R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;

$X^1$ and $X^2$ are independently halogen; and are bonded to Ru in a trans orientation or in a cis orientation;

$R^{8p}$, $R^{9p}$, $R^{10p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring).

In other embodiments, metal carbene olefin metathesis catalysts of the invention are represented by the structure of Formula (VII), wherein:

Q is a two-atom linkage having the structure —$CR^{11}R^{12}$—$CR^{13}R^{14}$— wherein $R^{11}$, $R^{12}$, $R^{13}$, and $R^{14}$ are independently hydrogen;

$R^3$ and $R^4$ are the same and are each phenyl substituted with up to three substituents selected from $C_1$-$C_{20}$ alkyl;

$X^1$ and $X^2$ are independently halogen; and are bonded to Ru in a trans orientation;

$R^{8p}$, $R^{9p}$, $R^{10p}$ are each independently methyl, ethyl, isopropyl, n-butyl, sec-butyl, tert-butyl, 4-methoxyphenyl, benzyl, or phenyl;

m is 0 or 1; and $R^1$ is hydrogen, and $R^2$ is phenyl, 2-isopropoxyphenyl or —CH=$C(CH_3)_2$, or $R^1$ and $R^2$ may be taken together to form an indenylidene moiety, preferably phenylindenylidene.

In other embodiments, metal carbene olefin metathesis catalysts of the invention are represented by the structure of Formula (VII), wherein:

Q is a two-atom linkage having the structure —CR$^{11}$R$^{12}$—CR$^{13}$R$^{14}$— wherein R$^{11}$, R$^{12}$, R$^{13}$, and R$^{14}$ are independently hydrogen;
R$^3$ and R$^4$ are the same and are each phenyl substituted with up to three substituents selected from C$_1$-C$_{20}$ alkyl;
X$^1$ and X$^2$ are independently halogen; and are bonded to Ru in a cis orientation;
R$^{8p}$, R$^{9p}$, R$^{10p}$ are each independently methyl, ethyl, isopropyl, n-butyl, sec-butyl, tert-butyl, 4-methoxyphenyl, benzyl, or phenyl;
m is 0 or 1; and
R$^1$ is hydrogen, and R$^2$ is phenyl, 2-isopropoxyphenyl or —CH=C(CH$_3$)$_2$, or R$^1$ and R$^2$ may be taken together to form an indenylidene moiety, preferably phenylindenylidene.

In other embodiments, metal carbene olefin metathesis catalysts of the invention are represented by the structure of Formula (VII), wherein:
Q is a two-atom linkage having the structure —CR$^{11}$R$^{12}$—CR$^{13}$R$^{14}$— wherein R$^{11}$, R$^{12}$, R$^{13}$, and R$^{14}$ are independently hydrogen;
R$^3$ and R$^4$ are the same and are mesityl;
X$^1$ and X$^2$ are chloride, and are bonded to Ru in a trans orientation;
R$^{8p}$ is methyl;
R$^{9p}$ is methyl;
R$^{10p}$ is phenyl;
m is 0 or 1; and
R$^1$ is hydrogen, and R$^2$ is phenyl, 2-isopropoxyphenyl or —CH=C(CH$_3$)$_2$, or R$^1$ and R$^2$ may be taken together to form an indenylidene moiety, preferably phenylindenylidene.

In other embodiments, metal carbene olefin metathesis catalysts of the invention are represented by the structure of Formula (VII), wherein:
Q is a two-atom linkage having the structure —CR$^{11}$R$^{12}$—CR$^{13}$R$^{14}$— wherein R$^{11}$, R$^{12}$, R$^{13}$, and R$^{14}$ are independently hydrogen;
R$^3$ and R$^4$ are the same and are mesityl;
X$^1$ and X$^2$ are chloride, and are bonded to Ru in a cis orientation;
R$^{8p}$ is methyl;
R$^{9p}$ is methyl;
R$^{10p}$ is phenyl;
m is 0 or 1; and
R$^1$ is hydrogen, and R$^2$ is phenyl, 2-isopropoxyphenyl or —CH=C(CH$_3$)$_2$, or R$^1$ and R$^2$ may be taken together to form an indenylidene moiety, preferably phenylindenylidene.

In one embodiment metal carbene olefin metathesis catalysts of the invention are represented by the structure of Formula (VIIa):

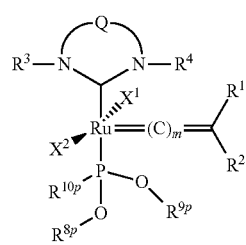

Formula (VIIa)

wherein: Q is a two-atom linkage having the structure —CR$^{11}$R$^{12}$—CR$^{13}$R$^{14}$— or —CR=CR$^{13}$—, preferably —CR$^{11}$R$^{12}$—CR$^{13}$R$^{14}$—, wherein R$^{11}$, R$^{12}$, R$^{13}$, and R$^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, C$_1$-C$_{12}$ alkyl, substituted C$_1$-C$_{12}$ alkyl, C$_1$-C$_{12}$ heteroalkyl, substituted C$_1$-C$_{12}$ heteroalkyl, phenyl, or substituted phenyl, alternatively, any two of R$^{11}$, R$^{12}$, R$^{13}$, and R$^{14}$ may be linked together to form a substituted or unsubstituted, saturated or unsaturated ring structure; e.g., a C$_4$-C$_{12}$ alicyclic group or a C$_5$ or C$_6$ aryl group, which may itself be substituted, e.g., with linked or fused alicyclic or aromatic groups, or with other substituents, or any one or more of R$^{11}$, R$^{12}$, R$^{13}$, and R$^{14}$ comprises one or more of the linkers;
R$^3$ and R$^4$ may be unsubstituted phenyl or phenyl substituted with one or more substituents such as C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, C$_6$-C$_{24}$ aralkyl, C$_6$-C$_{24}$ alkaryl, or halide, or are aromatic, they are typically although not necessarily, composed of one or two aromatic rings, which may or may not be substituted, e.g., R$^3$ and R$^4$ may be phenyl, substituted phenyl, biphenyl, substituted biphenyl, or the like, preferably R$^3$ and R$^4$ are the same and are each substituted phenyl or phenyl substituted with up to three substituents selected from C$_1$-C$_{20}$ alkyl, substituted C$_1$-C$_{20}$ alkyl, C$_1$-C$_{20}$ heteroalkyl, substituted C$_1$-C$_{20}$ heteroalkyl, C$_5$-C$_{24}$ aryl, substituted C$_5$-C$_{24}$ aryl, C$_5$-C$_{24}$ heteroaryl, C$_6$-C$_{24}$ aralkyl, C$_6$-C$_{24}$ alkaryl, and halide, preferred substituents present are hydrogen, C$_1$-C$_{12}$ alkyl, C$_1$-C$_{12}$ alkoxy, C$_5$-C$_{14}$ aryl, substituted C$_5$-C$_{14}$ aryl, or halide;
X$^1$ and X$^2$ are independently halogen; and are bonded to Ru in a trans orientation;
R$^{8p}$, R$^{9p}$, R$^{10p}$ are each independently substituted or unsubstituted C$_6$-C$_{10}$ aryl, or substituted or unsubstituted C$_1$-C$_{10}$ alkyl, or substituted or unsubstituted C$_3$-C$_8$ cycloalkyl;
m is 0, 1, or 2;
R$^1$ and R$^2$ are independently hydrogen, hydrocarbyl, substituted hydrocarbyl, heteroatom-containing hydrocarbyl, substituted heteroatom-containing hydrocarbyl, or functional groups, or R$^1$ and R$^2$ may be linked together to form a ring (for example C$_4$-C$_{10}$ ring, or C$_5$-C$_6$ ring) that may be substituted or unsubstituted, saturated or unsaturated and may be fused or linked to a further ring (for example a C$_4$-C$_{10}$ ring or a C$_5$-C$_6$ ring).

In one embodiment metal carbene olefin metathesis catalysts of the invention are represented by the structure of Formula (VIIa):
where R$^1$, R$^2$, R$^3$, R$^4$, X$^1$X$^2$, m, R$^{8p}$, R$^{9p}$, R$^{10p}$, and Q are as defined above for a complex having the structure of Formula (VII); and wherein the complex is a positional isomer, wherein X$^1$ and X$^2$ are bonded to Ru in a trans orientation.

In one embodiment metal carbene olefin metathesis catalysts of the invention are represented by the structure of Formula (VIIb):

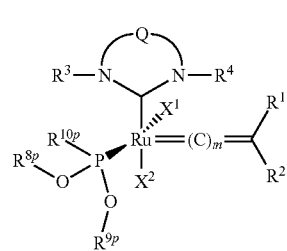

Formula (VIIb)

wherein: Q is a two-atom linkage having the structure —$CR^{11}R^{12}$—$CR^{13}R^{14}$— or —$CR$=$CR^{13}$—, preferably —$CR^{11}R^{12}$—$CR^{13}R^{14}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups, or are preferably independently hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, or substituted phenyl, alternatively, any two of $R^{11}$, $R^{12}$, $R^{13}$, and $R^{14}$ may be linked together to form a substituted or unsubstituted, saturated or unsaturated ring structure; e.g., a $C_4$-$C_{12}$ alicyclic group or a $C_5$ or $C_6$ aryl group, which may itself be substituted, e.g., with linked or fused alicyclic or aromatic groups, or with other substituents, or any one or more of $R^{11}$, $R^{12}$, $R^{13}$, and $R^{14}$ comprises one or more of the linkers;

$R^3$ and $R^4$ may be unsubstituted phenyl or phenyl substituted with one or more substituents such as $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide, or are aromatic, they are typically although not necessarily, composed of one or two aromatic rings, which may or may not be substituted, e.g., $R^3$ and $R^4$ may be phenyl, substituted phenyl, biphenyl, substituted biphenyl, or the like, preferably $R^3$ and $R^4$ are the same and are each unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, and halide, preferred substituents present are hydrogen, $C_1$-$C_{12}$ alkyl, $C_1$-$C_{12}$ alkoxy, $C_5$-$C_{14}$ aryl, substituted $C_5$-$C_{14}$ aryl, or halide;

$X^1$ and $X^2$ are independently halogen; and are bonded to Ru in a cis orientation;

$R^{8p}$, $R^{9p}$, $R^{10p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl;

m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or functional groups, or $R^1$ and $R^2$ may be linked together to form a ring (for example $C_4$-$C_{10}$ ring, or $C_5$-$C_6$ ring) that may be substituted or unsubstituted, saturated or unsaturated and may be fused or linked to a further ring (for example a $C_4$-$C_{10}$ ring or a $C_5$-$C_6$ ring).

In one embodiment metal carbene olefin metathesis catalysts of the invention are represented by the structure of Formula (VIIb):

where $R^1$, $R^2$, $R^3$, $R^4$, $X^1X^2$, m, $R^{8p}$, $R^{9p}$, $R^{10p}$, and Q are as defined above for a complex having the structure of Formula (VII); and wherein the complex is a positional isomer, wherein $X^1$ and $X^2$ are bonded to Ru in a cis orientation.

Numerous embodiments of the metal carbene olefin metathesis catalysts of the invention are described in more detail infra.

Non-limiting examples of metal carbene olefin metathesis catalysts having the structure of Formula (VI) include the following, some of which for convenience are identified throughout this disclosure by reference to their molecular weight:

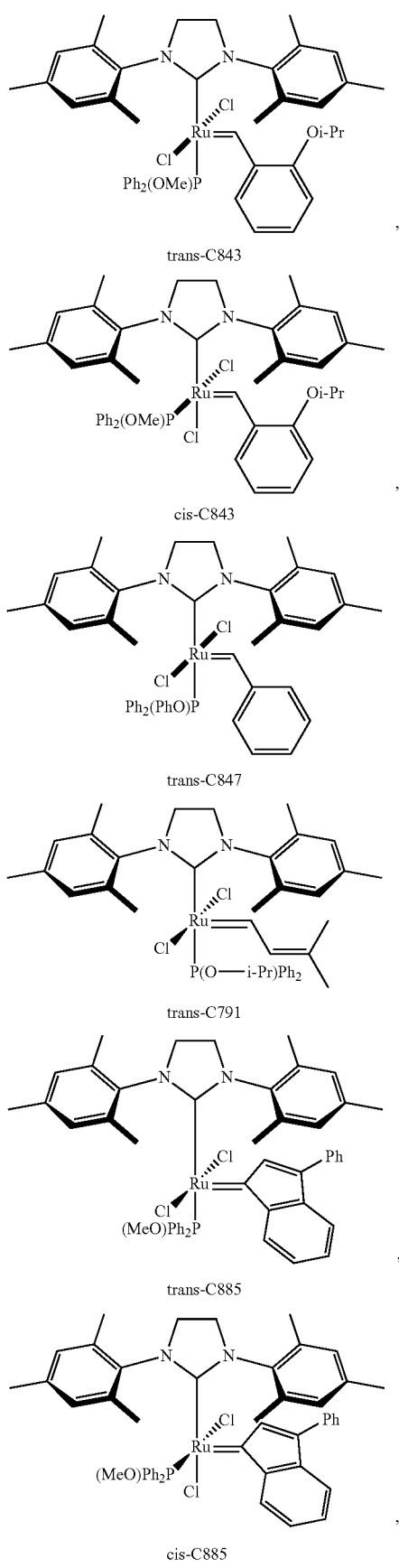

trans-C843, cis-C843, trans-C847, trans-C791, trans-C885, cis-C885

-continued
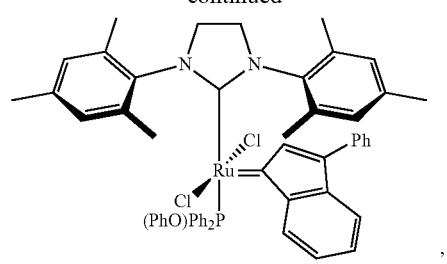
trans-C947
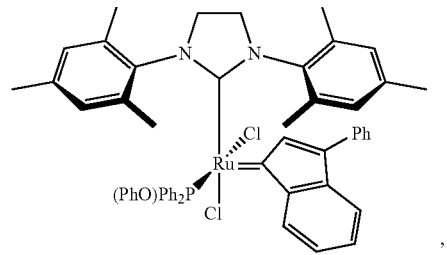
cis-C947
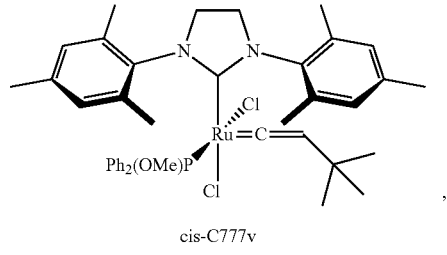
cis-C777v
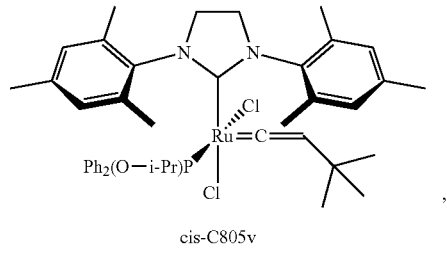
cis-C805v
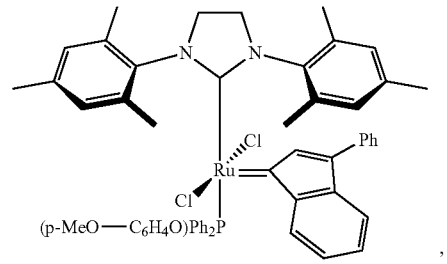
trans-C977
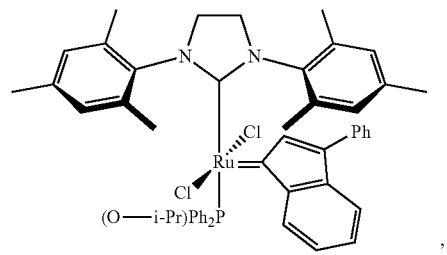
trans-C913
-continued
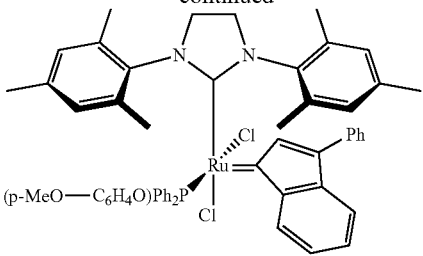
cis-C977
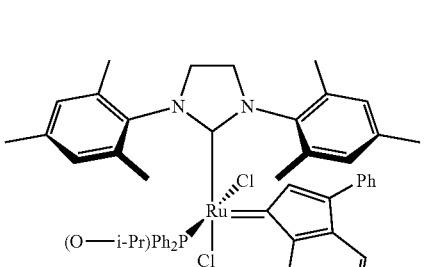
Cis-C913
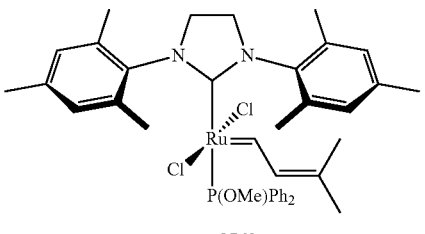
trans-C763
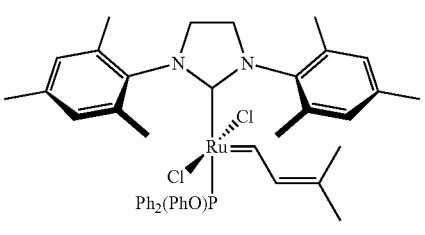
trans-C825
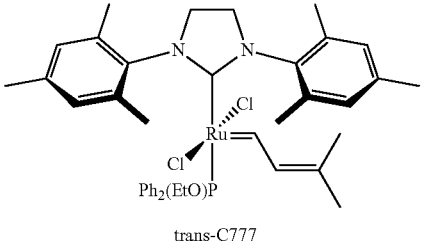
trans-C777
Non-limiting examples of metal carbene olefin metathesis catalysts having the structure of Formula (VII) include the following, some of which for convenience are identified throughout this disclosure by reference to their molecular weight:

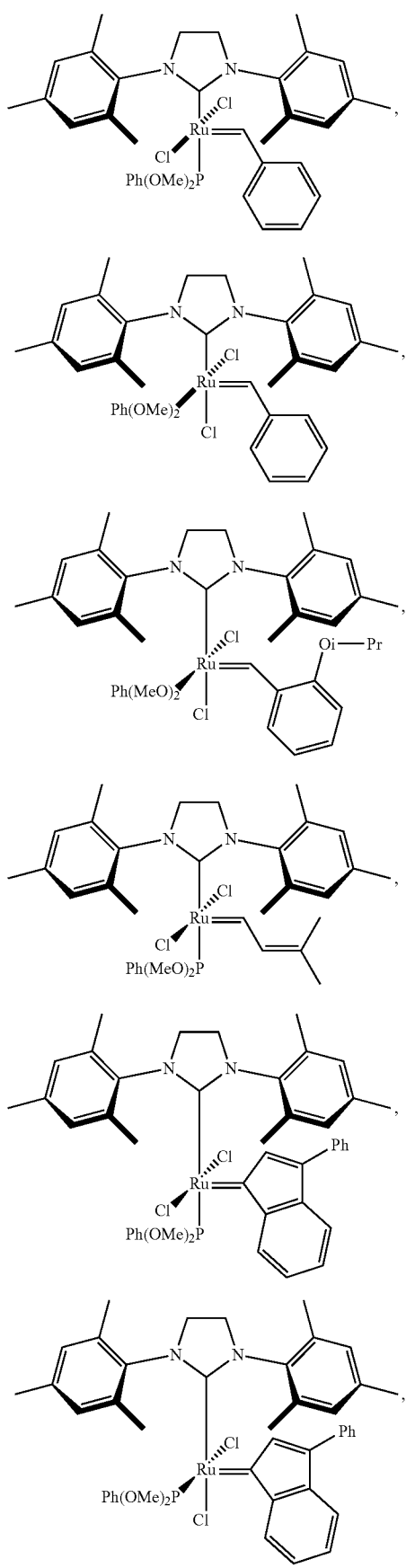

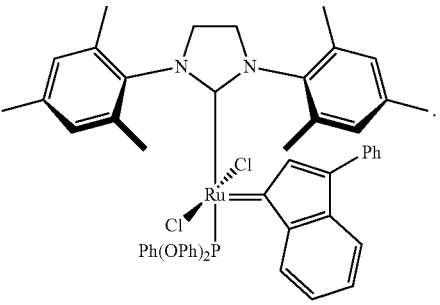

Further examples of metal carbene olefin metathesis catalysts having the structure of Formula (VI) disclosed herein include the following: trans-RuCl$_2$(sIMes)(CHC$_6$H$_4$Oi-Pr) (Ph$_2$P(OMe)) (trans-C843); trans-RuCl$_2$(sIMes) (Benzylidene)(Ph$_2$P(OPh)) (trans-C847); trans-RuCl$_2$ (sIMes) (Phenylindenylidene) (Ph$_2$P(OMe)) (trans-C885); trans-RuCl$_2$(sIMes) (Phenylindenylidene)(Ph$_2$P(OPh)) (trans-C947); trans-RuCl$_2$ (sIMes) (Phenylindenylidene) (Ph$_2$P(O-p-C$_6$H$_4$OMe)) (trans-C977); trans-RuCl$_2$(sIMes) (Phenylindenylidene)(Ph$_2$P(OiPr)) (trans-C913); trans-RuCl$_2$(sIMes)(3-methyl-2-butenylidene)(Ph$_2$P(OiPr)) (trans-C791); trans-RuCl$_2$(sIMes) (3-methyl-2-butenylidene) (Ph$_2$P(OMe)) (trans-C763); trans-RuCl$_2$(sIMes) (3-methyl-2-butenylidene)(Ph$_2$P(OEt)) (trans-C777); trans-RuCl$_2$(sIMes)(3-methyl-2-butenylidene)(Ph$_2$P(OPh)) (trans-C825).

Further examples of metal carbene olefin metathesis catalysts having the structure of Formula (VI) disclosed herein include the following: trans-RuCl$_2$(sIMes)(CHC$_6$H$_4$Oi-Pr) (Ph$_2$P(OMe)) (trans-C843).

Further examples of metal carbene olefin metathesis catalysts having the structure of Formula (VI) disclosed herein include the following: trans-RuCl$_2$(sIMes) (Benzylidene) (Ph$_2$P(OPh))(trans-C847).

Further examples of metal carbene olefin metathesis catalysts having the structure of Formula (VI) disclosed herein include the following: trans-RuCl$_2$ (sIMes) (Phenylindenylidene)(Ph$_2$P(OMe)) (trans-C885); trans-RuCl$_2$(sIMes) (Phenylindeny lidene) (Ph$_2$P(OPh)) (trans-C947); trans-RuCl$_2$(sIMes)(Phenylindenylidene) (Ph$_2$P(O-p-C$_6$H$_4$OMe)) (trans-C977); trans-RuCl$_2$(sIMes)(Phenylindenylidene) (Ph$_2$P(OiPr)) (trans-C913); trans-RuCl$_2$(sIMes)(3-methyl-2-butenylidene) (Ph$_2$P(OPh)) (trans-C825).

Further examples of metal carbene olefin metathesis catalysts having the structure of Formula (VI) disclosed herein include the following: trans-RuCl$_2$(sIMes)(3-methyl-2-butenylidene)(Ph$_2$P(OiPr)) (trans-C791); trans-RuCl$_2$(sIMes) (3-methyl-2-butenylidene) (Ph$_2$P(OMe)) (trans-C763); trans-RuCl$_2$(sIMes)(3-methyl-2-butenylidene)(Ph$_2$P(OEt)) (trans-C777).

Further examples of metal carbene olefin metathesis catalysts having the structure of Formula (VI) disclosed herein include the following: cis-RuCl$_2$(sIMes)(CHC$_6$H$_4$Oi-Pr) (Ph$_2$P(OMe)) (cis-C843); cis-RuCl$_2$ (sIMes) (Phenylindenylidene) (Ph$_2$P(OMe)) (cis-C885); cis-RuCl$_2$(sIMes) (Phenylindenylidene) (Ph$_2$P(OPh)) (cis-C947); cis-RuCl$_2$ (sIMes) (Phenylindenylidene)(Ph$_2$P(O-p-C$_6$H$_4$OMe)) (cis-C977); cis-RuCl$_2$(sIMes) (Phenylindenylidene) (Ph$_2$P(O-i-Pr)) (cis-C913); cis-RuCl$_2$(sIMes) (Phenylindenylidene) (PhP(OMe)$_2$) (cis-C834); cis-RuCl$_2$(sIMes)(t-butylvinylidene)(Ph₂P(OMe)) (cis-C777v); cis-RuCl₂(sIMes)(t-butylvinylidene) (Ph₂P(O-i-Pr)) (cis-C805v).

Further examples of metal carbene olefin metathesis catalysts having the structure of Formula (VI) disclosed herein include the following: cis-RuCl₂(sIMes)(CHC₆H₄Oi-Pr) (Ph₂P(OMe)) (cis-C843).

Further examples of metal carbene olefin metathesis catalysts having the structure of Formula (VI) disclosed herein include the following: cis-RuCl₂ (sIMes) (Phenylindenylidene)(Ph₂P(OMe)) (cis-C885); cis-RuCl₂(sIMes)(Phenylindenylidene) (Ph₂P(OPh)) (cis-C947); cis-RuCl₂ (sIMes)(Phenylindenylidene)(Ph₂P(O-p-C₆H₄OMe)) (cis-C977); cis-RuCl₂(sIMes) (Phenylindenylidene) (Ph₂P(O-i-Pr)) (cis-C913).

Further examples of metal carbene olefin metathesis catalysts having the structure of Formula (VI) disclosed herein include the following: cis-RuCl₂(sIMes)(t-butylvinylidene) (Ph₂P(OMe)) (cis-C777v); cis-RuCl₂(sIMes)(t-butylvinylidene) (Ph₂P(O-i-Pr)) (cis-C805v).

Further examples of metal carbene olefin metathesis catalysts having the structure of Formula (VII) disclosed herein include the following: trans-RuCl₂ (sIMes)(Benzylidene) (PhP(OMe)₂) (trans-C739); trans-RuCl₂(sIMes) (Phenylindenylidene) (PhP(OMe)₂) (trans-C834); trans-RuCl₂(sIMes) (3-methyl-2-butenylidene)(PhP(OMe)₂) (trans-C717); cis-RuCl₂(sIMes)(Benzylidene) (PhP(OMe)₂) (cis-739); cis-RuCl₂(sIMes)(CHC₆H₄Oi-Pr)(PhP(OMe)₂) (cis-C797); cis-RuCl₂(sIMes)(Phenylindenylidene)(PhP(OMe)₂) (cis-C834);

Further examples of metal carbene olefin metathesis catalysts having the structure of Formula (VII) disclosed herein include the following: trans-RuCl₂ (sIMes)(Benzylidene) (PhP(OMe)₂) (trans-C739); trans-RuCl₂(sIMes) (Phenylindenylidene) (PhP(OMe)₂) (trans-C834); trans-RuCl₂(sIMes) (3-methyl-2-butenylidene)(PhP(OMe)₂) (trans-C717); cis-RuCl₂ (sIMes)(Benzylidene)(PhP(OMe)₂); trans-RuCl₂ (sIMes)(Phenylindenylidene)(PhP(OPh)₂) (trans-C963).

Further examples of metal carbene olefin metathesis catalysts having the structure of Formula (VII) disclosed herein include the following: (cis-739); cis-RuCl₂(sIMes) (CHC₆H₄Oi-Pr)(PhP(OMe)₂) (cis-C797); cis-RuCl₂(sIMes) (Phenylindenylidene)(PhP(OMe)₂) (cis-C834).

The present invention concerns also processes for preparing the metal carbene olefin metathesis catalysts described above. The metal carbene olefin metathesis catalysts according to the invention can be prepared analogously to conventional methods as understood by the person skilled in the art of synthetic organic chemistry. For example, synthetic Schemes 2 and 3 set forth below, illustrate how the compounds according to the invention can be made.

Scheme 2

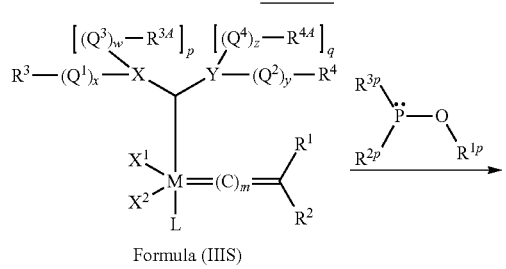

Formula (IIIS)

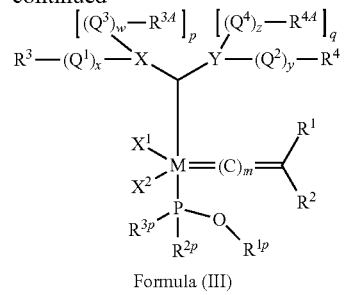

Formula (III)

The metal carbene olefin metathesis catalysts according to Formula (III), wherein L² is a phosphinite ligand, were prepared according to general Scheme 3. In general, a metal carbene olefin metathesis represented by Formula (IIIS), wherein R³, R⁴, Q, X¹, X², m, R¹ and R² are defined as in the case of Formula (III) and L is a neutral electron donor ligand, is reacted with an excess of phosphinite to produce the corresponding metal carbene olefin metathesis catalysts represented by Formula (VI).

Scheme 3

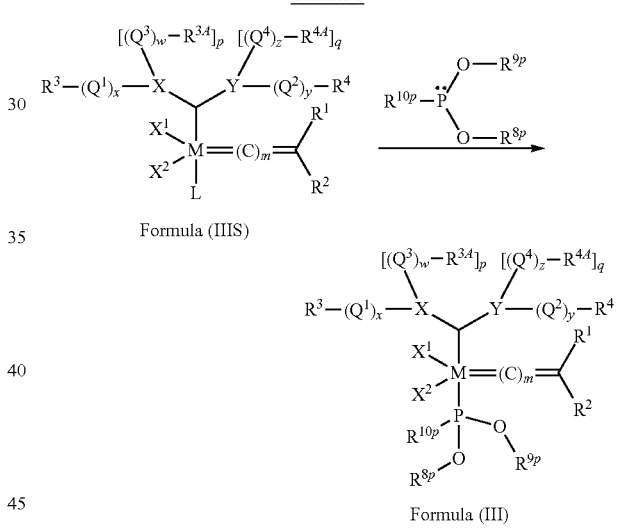

Formula (III)

The metal carbene olefin metathesis catalysts according to Formula (III), wherein L² is a phosphonite ligand, were prepared according to general Scheme 3. In general, a metal carbene olefin metathesis represented by Formula (IIIS), as described above, is reacted with an excess of phosphonite to produce the corresponding metal carbene olefin metathesis catalysts represented by Formula (III).

In one embodiment, the reaction in synthetic Schemes 2 or 3, takes place under degassed N₂ at room temperature or at high temperature in dichloromethane or toluene. Once the reaction is completed, the mixture is cooled to room temperature, the solvent is removed under high vacuum, and the residue is purified on a silica gel column and then recrystallized to afford the new metal carbene olefin metathesis catalyst.

At this stage, those skilled in the art will appreciate that many additional compounds that fall under the scope of the invention may be prepared by performing various common chemical reactions. Details of certain specific chemical transformations are provided in the examples.

The metal carbene olefin metathesis catalysts may be utilized in olefin metathesis reactions according to techniques known in the art. For example, the metal carbene olefin metathesis catalysts are typically added to a resin composition as a solid, a solution, or as a suspension. When the metal carbene olefin metathesis catalysts are added to a resin composition as a suspension, the metal carbene olefin metathesis catalysts are suspended in a dispersing carrier such as mineral oil, paraffin oil, soybean oil, tri-isopropylbenzene, or any hydrophobic liquid which has a sufficiently high viscosity so as to permit effective dispersion of the catalyst(s), and which is sufficiently inert and which has a sufficiently high boiling point so that is does not act as a low-boiling impurity in the olefin metathesis reaction. It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate (e.g., cyclic olefins).

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate (e.g, cyclic olefins).

When expressed as the molar ratio of monomer to catalyst, the catalyst (the "monomer to catalyst ratio"), loading will generally be present in an amount that ranges from a low of about 10,000,000:1, 1,000,000:1, 500,000:1 or 200,00:1, to a high of about 100,000:1 60,000:1, 50,000:1, 45,000;1, 40,000:1, 30,000:1, 20,000:1, 10,000:1, 5,000:1, or 1,000:1.

Cyclic Olefins

Resin compositions that may be used with the present invention disclosed herein comprise one or more cyclic olefins. In general, any cyclic olefin suitable for metathesis reactions disclosed herein may be used. Such cyclic olefins may be optionally substituted, optionally heteroatom-containing, mono-unsaturated, di-unsaturated, or poly-unsaturated $C_5$ to $C_{24}$ hydrocarbons that may be mono-, di-, or poly-cyclic. The cyclic olefin may generally be any strained or unstrained cyclic olefin, provided the cyclic olefin is able to participate in a ROMP reaction either individually or as part of a ROMP cyclic olefin composition. While certain unstrained cyclic olefins such as cyclohexene are generally understood to not undergo ROMP reactions by themselves, under appropriate circumstances, such unstrained cyclic olefins may nonetheless be ROMP active. For example, when present as a co-monomer in a ROMP composition, unstrained cyclic olefins may be ROMP active. Accordingly, as used herein and as would be appreciated by the skilled artisan, the term "unstrained cyclic olefin" is intended to refer to those unstrained cyclic olefins that may undergo a ROMP reaction under any conditions, or in any ROMP composition, provided the unstrained cyclic olefin is ROMP active.

In general, the cyclic olefin may be represented by the structure of Formula (A)

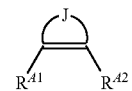

Formula (A)

wherein J, $R^{A1}$, and $R^{A2}$ are as follows:

$R^{A1}$ and $R^{A2}$ are selected independently from the group consisting of hydrogen, hydrocarbyl (e.g., $C_1$-$C_{20}$ alkyl, $C_5$-$C_{20}$ aryl, $C_5$-$C_{30}$ aralkyl, or $C_5$-$C_{30}$ alkaryl), substituted hydrocarbyl (e.g., substituted $C_1$-$C_{20}$ alkyl, $C_5$-$C_{20}$ aryl, $C_5$-$C_{30}$ aralkyl, or $C_5$-$C_{30}$ alkaryl), heteroatom-containing hydrocarbyl (e.g., $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl), and substituted heteroatom-containing hydrocarbyl (e.g., substituted $C_1$-$C_{20}$ heteroalkyl, $C_5$-$C_{20}$ heteroaryl, heteroatom-containing $C_5$-$C_{30}$ aralkyl, or heteroatom-containing $C_5$-$C_{30}$ alkaryl) and, if substituted hydrocarbyl or substituted heteroatom-containing hydrocarbyl, wherein the substituents may be functional groups ("Fn") such as phosphonato, phosphoryl, phosphanyl, phosphino, sulfonato, $C_1$-$C_{20}$ alkylsulfanyl, $C_5$-$C_{20}$ arylsulfanyl, $C_1$-$C_{20}$ alkylsulfonyl, $C_5$-$C_{20}$ arylsulfonyl, $C_1$-$C_{20}$ alkylsulfinyl, $C_5$-$C_{20}$ arylsulfinyl, sulfonamido, amino, amido, imino, nitro, nitroso, hydroxyl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, carboxyl, carboxylato, mercapto, formyl, $C_1$-$C_{20}$ thioester, cyano, cyanato, thiocyanato, isocyanate, thioisocyanate, carbamoyl, epoxy, styrenyl, silyl, silyloxy, silanyl, siloxazanyl, boronato, boryl, or halogen, or a metal-containing or metalloid-containing group (wherein the metal may be, for example, Sn or Ge). $R^{A1}$ and $R^{A2}$ may itself be one of the aforementioned groups, such that the Fn moiety is directly bound to the olefinic carbon atom indicated in the structure. In the latter case, however, the functional group will generally not be directly bound to the olefinic carbon through a heteroatom containing one or more lone pairs of electrons, e.g., an oxygen, sulfur, nitrogen, or phosphorus atom, or through an electron-rich metal or metalloid such as Ge, Sn, As, Sb, Se, Te, etc. With such functional groups, there will normally be an intervening linkage Z*, such that $R^{A1}$ and/or $R^{A2}$ then has the structure —(Z*)$_n$-Fn wherein n is 1, Fn is the functional group, and Z* is a hydrocarbylene linking group such as an alkylene, substituted alkylene, heteroalkylene, substituted heteroalkene, arylene, substituted arylene, heteroarylene, or substituted heteroarylene linkage.

J is a saturated or unsaturated hydrocarbylene, substituted hydrocarbylene, heteroatom-containing hydrocarbylene, or substituted heteroatom-containing hydrocarbylene linkage, wherein when J is substituted hydrocarbylene or substituted heteroatom-containing hydrocarbylene, the substituents may include one or more —(Z*)$_n$-Fn groups, wherein n is 0 or 1, and Fn and Z* are as defined previously. Additionally, two or more substituents attached to ring carbon (or other) atoms within J may be linked to form a bicyclic or polycyclic olefin. J will generally contain in the range of approximately 5 to 14 ring atoms, typically 5 to 8 ring atoms, for a monocyclic olefin, and, for bicyclic and polycyclic olefins, each ring will generally contain 4 to 8, typically 5 to 7, ring atoms.

Mono-unsaturated cyclic olefins encompassed by Formula (A) may be represented by the Formula (B)

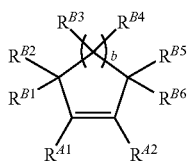

Formula (B)

wherein b is an integer generally although not necessarily in the range of 1 to 10, typically 1 to 5, $R^{A1}$ and $R^{A2}$ are as defined above for Formula (A), and $R^{B1}$, $R^{B2}$, $R^{B3}$, $R^{B4}$, $R^{B5}$, and $R^{B6}$ are independently selected from the group consisting of hydrogen, hydrocarbyl, substituted hydrocarbyl, heteroatom-containing hydrocarbyl, substituted heteroatom-containing hydrocarbyl and —$(Z^*)_n$-Fn where n, $Z^*$, and Fn are as defined previously, and wherein if any of the $R^{B1}$ through $R^{B6}$ moieties is substituted hydrocarbyl or substituted heteroatom-containing hydrocarbyl, the substituents may include one or more —$(Z^*)_n$-Fn groups. Accordingly, $R^{B1}$, $R^{B2}$, $R^{B3}$, $R^{B4}$, $R^{B5}$, and $R^{B6}$ may be, for example, hydrogen, hydroxyl, $C_1$-$C_{20}$ alkyl, $C_5$-$C_{20}$ aryl, $C_1$-$C_{20}$ alkoxy, $C_5$-$C_{20}$ aryloxy, $C_2$-$C_{20}$ alkoxycarbonyl, $C_5$-$C_{20}$ aryloxycarbonyl, amino, amido, nitro, etc. Furthermore, any of the $R^{B1}$, $R^{B2}$, $R^{B3}$, $R^{B4}$, $R^{B5}$, and $R^{B6}$ moieties can be linked to any of the other $R^{B1}$, $R^{B2}$, $R^{B3}$, $R^{B4}$, $R^{B5}$, and $R^{B6}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is 0 or 1, $Z^*$ and Fn are as defined previously, and functional groups (Fn) provided above.

Examples of monounsaturated, monocyclic olefins encompassed by Formula (B) include, without limitation, cyclopentene, cyclohexene, cycloheptene, cyclooctene, cyclononene, cyclodecene, cycloundecene, cyclododecene, tricyclodecene, tetracyclodecene, octacyclodecene, and cycloeicosene, and substituted versions thereof such as 1-methylcyclopentene, 1-ethylcyclopentene, 1-isopropylcyclohexene, 1-chloropentene, 1-fluorocyclopentene, 4-methylcyclopentene, 4-methoxy-cyclopentene, 4-ethoxy-cyclopentene, cyclopent-3-ene-thiol, cyclopent-3-ene, 4-methylsulfanyl-cyclopentene, 3-methylcyclohexene, 1-methylcyclooctene, 1,5-dimethylcyclooctene, etc.

Monocyclic diene reactants encompassed by Formula (A) may be generally represented by the Formula (C)

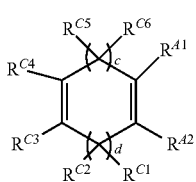

Formula (C)

wherein c and d are independently integers in the range of 1 to about 8, typically 2 to 4, preferably 2 (such that the reactant is a cyclooctadiene), $R^{A1}$ and $R^{A2}$ are as defined above for Formula (A), and $R^{C1}$, $R^{C2}$, $R^{C3}$, $R^{C4}$, $R^{C5}$, and $R^{C6}$ are defined as for $R^{B1}$ through $R^{B6}$. In this case, it is preferred that $R^{C3}$ and $R^{C4}$ be non-hydrogen substituents, in which case the second olefinic moiety is tetrasubstituted. Examples of monocyclic diene reactants include, without limitation, 1,3-cyclopentadiene, 1,3-cyclohexadiene, 1,4-cyclohexadiene, 5-ethyl-1,3-cyclohexadiene, 1,3-cycloheptadiene, cyclohexadiene, 1,5-cyclooctadiene, 1,3-cyclooctadiene, and substituted analogs thereof. Triene reactants are analogous to the diene Formula (C), and will generally contain at least one methylene linkage between any two olefinic segments.

Bicyclic and polycyclic olefins encompassed by Formula (A) may be generally represented by the Formula (D)

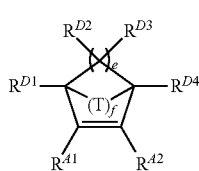

Formula (D)

wherein $R^{A1}$ and $R^{A2}$ are as defined above for Formula (A), $R^{D1}$, $R^{D2}$, $R^{D3}$, and $R^{D4}$ are as defined for $R^{B1}$ through $R^{B6}$, e is an integer in the range of 1 to 8 (typically 2 to 4), f is generally 1 or 2; T is lower alkylene or alkenylene (generally substituted or unsubstituted methyl or ethyl), $CHR^{G1}$, $C(R^{G1})_2$, O, S, N—$R^{G1}$, P—$R^{G1}$, O=P—$R^{G1}$, $Si(R^{G1})_2$, B—$R^{G1}$, or As—$R^{G1}$ where $R^{G1}$ is alkyl, alkenyl, cycloalkyl, cycloalkenyl, aryl, alkaryl, aralkyl, or alkoxy. Furthermore, any of the $R^{D1}$, $R^{D2}$, $R^{D3}$, and $R^{D4}$ moieties can be linked to any of the other $R^{D1}$, $R^{D2}$, $R^{D3}$, and $R^{D4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —$(Z^*)_n$-Fn where n is 0 or 1, $Z^*$ and Fn are as defined previously, and functional groups (Fn) provided above.

Cyclic olefins encompassed by Formula (D) are in the norbornene family. As used herein, norbornene means any compound that includes at least one norbornene or substituted norbornene moiety, including without limitation norbornene, substituted norbornene(s), norbornadiene, substituted norbornadiene(s), polycyclic norbornenes, and substituted polycyclic norbornene(s). Norbornenes within this group may be generally represented by the Formula (E)

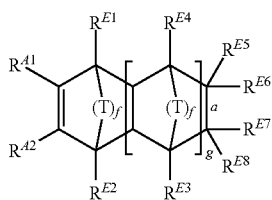

Formula (E)

wherein $R^{A1}$ and $R^A$ are as defined above for Formula (A), T is as defined above for Formula (D), $R^{E1}$, $R^{E2}$, $R^{E3}$, $R^{E4}$, $R^{E5}$, $R^{E6}$, $R^{E7}$, and $R^{E8}$ are as defined for $R^{B1}$ through $R^{B6}$, and "a" represents a single bond or a double bond, f is generally 1 or 2, "g" is an integer from 0 to 5, and when "a" is a double bond one of $R^{E5}$, $R^{E6}$ and one of $R^{E7}$, $R^{E8}$ is not present.

Furthermore, any of the $R^{E5}$, $R^{E6}$, $R^{E7}$, and $R^{E8}$ moieties can be linked to any of the other $R^{E5}$, $R^{E6}$, $R^{E7}$, and $R^{E8}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The cyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is 0 or 1, Z* and Fn are as defined previously, and functional groups (Fn) provided above.

More preferred cyclic olefins possessing at least one norbornene moiety have the Formula (F):

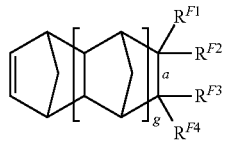

Formula (F)

wherein, $R^{F1}$, $R^{F2}$, $R^{F3}$, and $R^{F4}$, are as defined for $R^{B1}$ through $R^{B6}$, and "a" represents a single bond or a double bond, "g" is an integer from 0 to 5, and when "a" is a double bond one of $R^{F1}$, $R^{F2}$ and one of $R^{F3}$, $R^{F4}$ is not present.

Furthermore, any of the $R^{F1}$, $R^{F2}$, $R^3$, and $R^{F4}$ moieties can be linked to any of the other $R^{F1}$, $R^{F2}$, $R^{F3}$, and $R^{F4}$ moieties to provide a substituted or unsubstituted alicyclic group containing 4 to 30 ring carbon atoms or a substituted or unsubstituted aryl group containing 6 to 18 ring carbon atoms or combinations thereof and the linkage may include heteroatoms or functional groups, e.g., the linkage may include without limitation an ether, ester, thioether, amino, alkylamino, imino, or anhydride moiety. The alicyclic group can be monocyclic, bicyclic, or polycyclic. When unsaturated the cyclic group can contain monounsaturation or multiunsaturation, with monounsaturated cyclic groups being preferred. When substituted, the rings contain monosubstitution or multisubstitution wherein the substituents are independently selected from hydrogen, hydrocarbyl, substituted hydrocarbyl, heteroatom-containing hydrocarbyl, substituted heteroatom-containing hydrocarbyl, —(Z*)$_n$-Fn where n is 0 or 1, Z* and Fn are as defined previously, and functional groups (Fn) provided above.

One route for the preparation of hydrocarbyl substituted and functionally substituted norbornenes employs the Diels-Alder cycloaddition reaction in which cyclopentadiene or substituted cyclopentadiene is reacted with a suitable dienophile at elevated temperatures to form the substituted norbornene adduct generally shown by the following reaction Scheme 4:

SCHEME 4

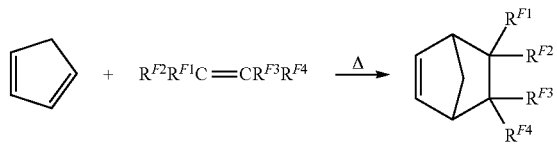

wherein, $R^{F1}$ to $R^{F4}$ are as previously defined for Formula (F).

Other norbornene adducts can be prepared by the thermal pyrolysis of dicyclopentadiene in the presence of a suitable dienophile. The reaction proceeds by the initial pyrolysis of dicyclopentadiene to cyclopentadiene followed by the Diels-Alder cycloaddition of cyclopentadiene and the dienophile to give the adduct shown below in Scheme 5:

SCHEME 5

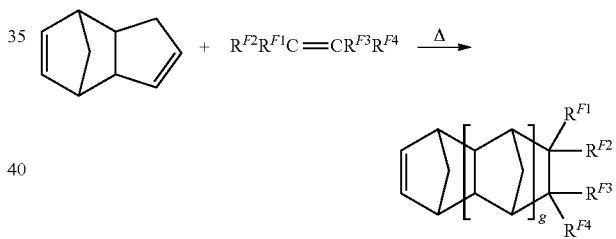

wherein "g" is an integer from 0 to 5, and $R^{F1}$ to $R^{F4}$ are as previously defined for Formula (F).

Norbornadiene and higher Diels-Alder adducts thereof similarly can be prepared by the thermal reaction of cyclopentadiene and dicyclopentadiene in the presence of an acetylenic reactant as shown below in Scheme 6:

SCHEME 6

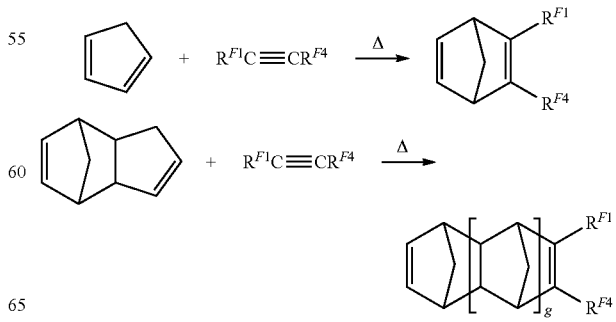

wherein "g" is an integer from 0 to 5, $R^{F1}$ and $R^{F4}$ are as previously defined for Formula (F).

Examples of bicyclic and polycyclic olefins thus include, without limitation, dicyclopentadiene (DCPD); trimer and other higher order oligomers of cyclopentadiene including without limitation tricyclopentadiene (cyclopentadiene trimer), cyclopentadiene tetramer, and cyclopentadiene pentamer; ethylidenenorbornene; dicyclohexadiene; norbornene; 5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethyoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5,6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyltetracyclododecene; 8-methoxycarbonyltetracyclododecene; 8-methyl-8-tetracyclododecene; 8-cyanotetracyclododecene; pentacyclopentadecene; pentacyclohexadecene; and the like, and their structural isomers, stereoisomers, and mixtures thereof. Additional examples of bicyclic and polycyclic olefins include, without limitation, $C_2$-$C_{12}$ hydrocarbyl substituted norbornenes such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, and 5-butenyl-2-norbornene, and the like. It is well understood by one in the art that bicyclic and polycyclic olefins as disclosed herein may consist of a variety of structural isomers and/or stereoisomers, any and all of which are suitable for use in the present invention. Any reference herein to such bicyclic and polycyclic olefins unless specifically stated includes mixtures of any and all such structural isomers and/or stereoisomers.

Preferred cyclic olefins include $C_5$ to $C_{24}$ unsaturated hydrocarbons. Also preferred are $C_5$ to $C_{24}$ cyclic hydrocarbons that contain one or more (typically 2 to 12) heteroatoms such as O, N, S, or P. For example, crown ether cyclic olefins may include numerous O heteroatoms throughout the cycle, and these are within the scope of the invention. In addition, preferred cyclic olefins are $C_5$ to $C_{24}$ hydrocarbons that contain one or more (typically 2 or 3) olefins. For example, the cyclic olefin may be mono-, di-, or tri-unsaturated. Examples of cyclic olefins include without limitation cyclooctene, cyclododecene, and (c,t,t)-1,5,9-cyclododecatriene.

The cyclic olefins may also comprise multiple (typically 2 or 3) rings. For example, the cyclic olefin may be mono-, di-, or tri-cyclic. When the cyclic olefin comprises more than one ring, the rings may or may not be fused. Preferred examples of cyclic olefins that comprise multiple rings include norbornene, dicyclopentadiene, tricyclopentadiene, and 5-ethylidene-2-norbornene.

The cyclic olefin may also be substituted, for example, a $C_5$ to $C_{24}$ cyclic hydrocarbon wherein one or more (typically 2, 3, 4, or 5) of the hydrogens are replaced with non-hydrogen substituents. Suitable non-hydrogen substituents may be chosen from the substituents described hereinabove. For example, functionalized cyclic olefins, i.e., $C_5$ to $C_{24}$ cyclic hydrocarbons wherein one or more (typically 2, 3, 4, or 5) of the hydrogens are replaced with functional groups, are within the scope of the invention. Suitable functional groups may be chosen from the functional groups described hereinabove. For example, a cyclic olefin functionalized with an alcohol group may be used to prepare a telechelic polymer comprising pendent alcohol groups. Functional groups on the cyclic olefin may be protected in cases where the functional group interferes with the metathesis catalyst, and any of the protecting groups commonly used in the art may be employed. Acceptable protecting groups may be found, for example, in Greene et al., Protective Groups in Organic Synthesis, 3rd Ed. (New York: Wiley, 1999). Examples of functionalized cyclic olefins include without limitation 2-hydroxymethyl-5-norbornene, 2-[(2-hydroxyethyl)carboxylate]-5-norbornene, cydecanol, 5-n-hexyl-2-norbornene, 5-n-butyl-2-norbornene.

Cyclic olefins incorporating any combination of the abovementioned features (i.e., heteroatoms, substituents, multiple olefins, multiple rings) are suitable for the methods disclosed herein. Additionally, cyclic olefins incorporating any combination of the abovementioned features (i.e., heteroatoms, substituents, multiple olefins, multiple rings) are suitable for the invention disclosed herein.

The cyclic olefins useful in the methods disclosed herein may be strained or unstrained. It will be appreciated that the amount of ring strain varies for each cyclic olefin compound, and depends upon a number of factors including the size of the ring, the presence and identity of substituents, and the presence of multiple rings. Ring strain is one factor in determining the reactivity of a molecule towards ring-opening olefin metathesis reactions. Highly strained cyclic olefins, such as certain bicyclic compounds, readily undergo ring opening reactions with olefin metathesis catalysts. Less strained cyclic olefins, such as certain unsubstituted hydrocarbon monocyclic olefins, are generally less reactive. In some cases, ring opening reactions of relatively unstrained (and therefore relatively unreactive) cyclic olefins may become possible when performed in the presence of the olefinic compounds disclosed herein. Additionally, cyclic olefins useful in the invention disclosed herein may be strained or unstrained.

The resin compositions of the present invention may comprise a plurality of cyclic olefins. A plurality of cyclic olefins may be used to prepare metathesis polymers from the olefinic compound. For example, two cyclic olefins selected from the cyclic olefins described hereinabove may be employed in order to form metathesis products that incorporate both cyclic olefins. Where two or more cyclic olefins are used, one example of a second cyclic olefin is a cyclic alkenol, i.e., a $C_5$-$C_{24}$ cyclic hydrocarbon wherein at least one of the hydrogen substituents is replaced with an alcohol or protected alcohol moiety to yield a functionalized cyclic olefin.

The use of a plurality of cyclic olefins, and in particular when at least one of the cyclic olefins is functionalized, allows for further control over the positioning of functional groups within the products. For example, the density of cross-linking points can be controlled in polymers and macromonomers prepared using the methods disclosed herein. Control over the quantity and density of substituents and functional groups also allows for control over the physical properties (e.g., melting point, tensile strength, glass transition temperature, etc.) of the products. Control over these and other properties is possible for reactions using only a single cyclic olefin, but it will be appreciated that the use of a plurality of cyclic olefins further enhances the range of possible metathesis products and polymers formed.

More preferred cyclic olefins include dicyclopentadiene; tricyclopentadiene; dicyclohexadiene; norbornene;

5-methyl-2-norbornene; 5-ethyl-2-norbornene; 5-isobutyl-2-norbornene; 5,6-dimethyl-2-norbornene; 5-phenylnorbornene; 5-benzylnorbornene; 5-acetylnorbornene; 5-methoxycarbonylnorbornene; 5-ethoxycarbonyl-1-norbornene; 5-methyl-5-methoxy-carbonylnorbornene; 5-cyanonorbornene; 5,5,6-trimethyl-2-norbornene; cyclo-hexenylnorbornene; endo, exo-5,6-dimethoxynorbornene; endo, endo-5,6-dimethoxynorbornene; endo, exo-5-6-dimethoxycarbonylnorbornene; endo, endo-5,6-dimethoxycarbonylnorbornene; 2,3-dimethoxynorbornene; norbornadiene; tricycloundecene; tetracyclododecene; 8-methyltetracyclododecene; 8-ethyl-tetracyclododecene; 8-methoxycarbonyltetracyclododecene; 8-methyl-8-tetracyclo-dodecene; 8-cyanotetracyclododecene; pentacyclopentadecene; pentacyclohexadecene; higher order oligomers of cyclopentadiene such as cyclopentadiene tetramer, cyclopentadiene pentamer, and the like; and $C_2$-$C_{12}$ hydrocarbyl substituted norbornenes such as 5-butyl-2-norbornene; 5-hexyl-2-norbornene; 5-octyl-2-norbornene; 5-decyl-2-norbornene; 5-dodecyl-2-norbornene; 5-vinyl-2-norbornene; 5-ethylidene-2-norbornene; 5-isopropenyl-2-norbornene; 5-propenyl-2-norbornene; and 5-butenyl-2-norbornene, and the like. Even more preferred cyclic olefins include dicyclopentadiene, tricyclopentadiene, and higher order oligomers of cyclopentadiene, such as cyclopentadiene tetramer, cyclopentadiene pentamer, and the like, tetracyclododecene, norbornene, and $C_2$-$C_{12}$ hydrocarbyl substituted norbornenes, such as 5-butyl-2-norbornene, 5-hexyl-2-norbornene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene, and the like.

It is to be understood that while the invention has been described in conjunction with specific embodiments thereof, that the description above as well as the examples that follow are intended to illustrate and not limit the scope of the invention. Other aspects, advantages, and modifications within the scope of the invention will be apparent to those skilled in the art to which the invention pertains.

Resin Compositions and Articles

Commercially important ROMP resin formulations are generally based on readily available and inexpensive cyclic olefins or polycyclic olefins such as dicyclopentadiene (DCPD), tricyclopentadiene (TCPD) and various other cycloalkenes. In one embodiment the cyclic olefin composition used in preparing the resin compositions and/or ROMP compositions of the invention, is dicyclopentadiene containing about 0% or about 6% or about 24% or about 40% or about 70% of tricyclopentadiene.

Resin compositions according to the invention generally comprise at least one cyclic olefin, where the resin composition is combined with at least one metal carbene olefin metathesis catalyst to form a ROMP composition.

Resin compositions according to the invention generally comprise at least one cyclic olefin, where the resin composition is combined with at least one metal carbene olefin metathesis catalyst of the invention to form a ROMP composition.

ROMP compositions according to the invention comprise at least one resin composition and at least one metal carbene olefin metathesis catalyst, wherein the resin composition comprises at least one cyclic olefin.

ROMP compositions according to the invention, comprise at least one resin composition and at least one metal carbene olefin metathesis catalyst selected from:

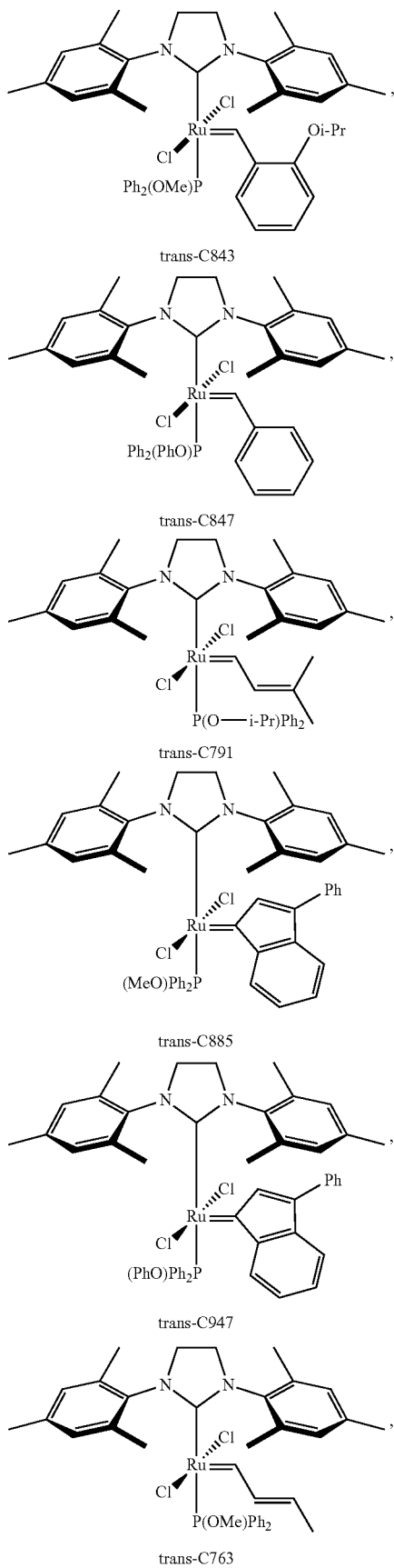

-continued

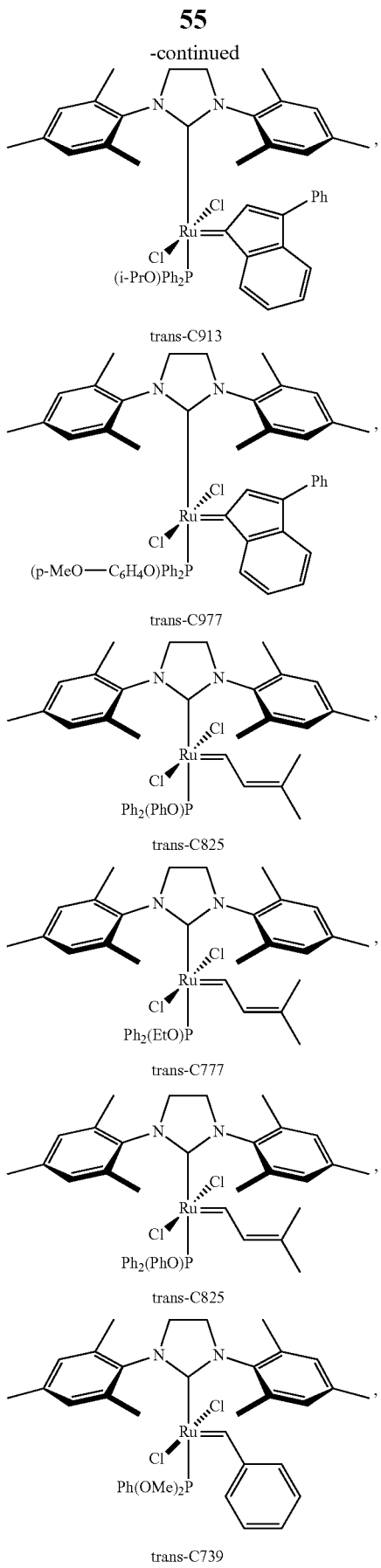

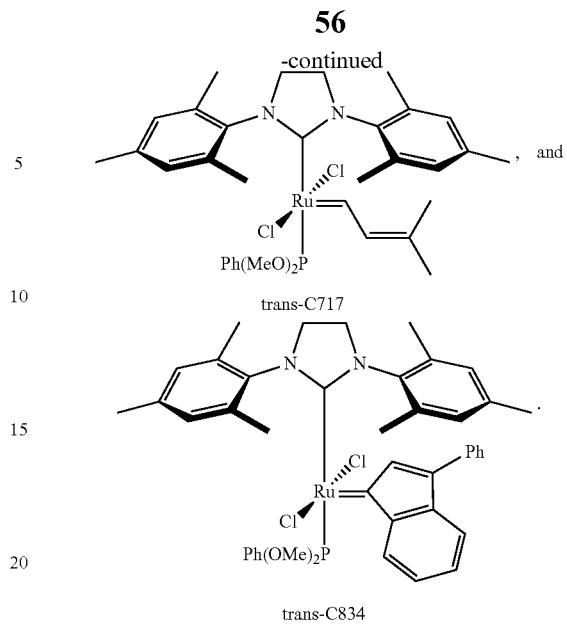

ROMP compositions according to the invention comprise at least one resin composition and at least one metal carbene olefin metathesis catalyst, wherein the resin composition comprises at least one cyclic olefin, wherein the at least one cyclic olefin is a norbornene derivative.

ROMP compositions according to the invention comprise at least one resin composition and at least one metal carbene olefin metathesis catalyst, wherein the resin composition comprises at least one cyclic olefin, wherein the at least one cyclic olefin is dicyclopentadiene.

ROMP compositions according to the invention comprise at least one resin composition and at least one metal carbene olefin metathesis catalyst, wherein the resin composition comprises at least one cyclic olefin, wherein the at least one cyclic olefin is tricyclopentadiene.

ROMP compositions according to the invention comprise at least one resin composition and at least one metal carbene olefin metathesis catalyst, wherein the resin composition comprises at least one cyclic olefin, wherein the at least one cyclic olefin is tetracyclopentadiene.

ROMP compositions according to the invention comprise at least one resin composition and at least one metal carbene olefin metathesis catalyst, wherein the resin composition comprises at least one cyclic olefin, wherein the at least one cyclic olefin is a norbornene derivative, such as 5-butyl-2-norbornene, 5-hexyl-2-norborene, 5-octyl-2-norbornene, 5-decyl-2-norbornene, 5-dodecyl-2-norbornene, 5-vinyl-2-norbornene, 5-ethylidene-2-norbornene, 5-isopropenyl-2-norbornene, 5-propenyl-2-norbornene, 5-butenyl-2-norbornene.

In another embodiment, resin compositions according to the invention may additionally comprise at least one exogenous inhibitor. Exogenous inhibitors or "gel modification additives", for use in the present invention are disclosed in U.S. Pat. No. 5,939,504, the contents of which are also incorporated herein by reference. Non-limiting examples of exogenous inhibitors or "gel modification additives" include water, tetrahydrofuran (THF), 2-methyltetrahydrofuran (2-Me-THF), diethyl ether ($(C_2H_5)_2O$), methyl-tert-butyl ether ($CH_3OC(CH_3)_3$), dimethoxyethane ($CH_3OCH_2CH_2OCH_3$), diglyme ($CH_3OCH_2OCH_2OCH_3$), trimethylphosphine ($PMe_3$), triethylphosphine ($PEt_3$), tributylphosphine ($PBu_3$), tri(ortho-tolyl)phosphine ($P\text{-}o\text{-}tolyl_3$), tri-tert-butylphosphine (P-tert-Bu$_3$), tricyclopentylphosphine (PCp$_3$), tricyclohexylphosphine (PCy$_3$), triisopropylphosphine (P-i-Pr$_3$), trioctylphosphine (POct$_3$), triisobutylphosphine (P-i-Bu$_3$), triphenylphosphine (PPh$_3$), tri(pentafluorophenyl)phosphine (P(C$_6$F$_5$)$_3$), methyldiphenylphosphine (PMePh$_2$), dimethylphenylphosphine (PMe$_2$Ph), diethylphenylphosphine (PEt$_2$Ph), trimethylphosphite (P(OMe)$_3$), triethylphosphite, (P(OEt)$_3$), triisopropylphosphite (P(O-i-Pr)$_3$), tributylphosphite (P(OBu)$_3$), triphenylphosphite (P(OPh)$_3$, and tribenzylphosphine (P(CH$_2$Ph)$_3$), 2-cyclohexenone, and triphenylphosphine oxide. Preferred exogenous inhibitors include triphenylphosphine, tricyclohexylphosphine, and tributylphosphine. The most preferred exogenous inhibitor is triphenylphosphine. When formulated or combined with a resin composition, the concentration of the exogenous inhibitor typically ranges from 0.001-10 phr, particularly 0.01-5 phr, more particularly 0.05-3 phr. Exogenous inhibitors may be added to the resin composition in the absence of solvent, or as organic solutions. A single exogenous inhibitor may be used, or a combination of two or more different exogenous inhibitors may be used.

In another embodiment, resin compositions according to the invention may additionally comprise a hydroperoxide gel modifier. Hydroperoxide gel modifiers for use in the present invention are disclosed in International Pat. App. No. PCT/US2012/042850, the contents of which are also incorporated herein by reference. Non-limiting examples of hydroperoxide gel modifiers include tert-butyl hydroperoxide, tert-amyl hydroperoxide, cumene hydroperoxide, diisopropyl benzene hydroperoxide, (2,5-dihydroperoxy)-2,5-dimethylhexane, cyclohexyl hydroperoxide, triphenylmethyl hydroperoxide, pinane hydroperoxide (e.g., Glidox® 500; LyondellBasell), and paramenthane hydroperoxide (e.g., Glidox® 300; LyondellBasell). More preferably, the hydroperoxides suitable for use include tert-butyl hydroperoxide and cumene hydroperoxide. Hydroperoxide gel-modification additives may be added to the reaction mixture in the absence of solvent, or as organic or aqueous solutions. A single hydroperoxide compound may be used as the gel-modification additive, or a combination of two or more different hydroperoxide compounds may be used. All concentrations of hydroperoxide which delay the onset of the gel-state of a particular metathesis polymerization. Advantageously, the use of hydroperoxides gel modifiers has been found to substantially maintain the properties of the cured polymer including peak exotherm temperature and mechanical properties. While not necessarily limited, the hydroperoxide concentration is advantageously between 0.01 and 1000 equivalents with respect to catalyst. In other embodiments the hydroperoxide concentration may be between 0.1 and 20 equivalents with respect to catalyst. Generally, higher concentrations of hydroperoxide will lead to longer pot life. Additionally, in other embodiments the hydroperoxide concentration may be between 0.05 and 100 equivalents with respect to catalyst. Additionally, in other embodiments the hydroperoxide concentration may be between 0.1 and 50 equivalents with respect to catalyst.

In another embodiment, resin compositions of the invention may additionally comprise at least one 5-alkenyl-2-norbornene as a pot life adjusting agent. 5-alkenyl-2-norbornenes for use in the present invention are disclosed in U.S. Pat. No. 5,204,427 and non-limiting examples include 5-vinylbicyclo[2.2.1]hepto-2-ene (5-vinyl-2-norbornene); 5-isopropenylbicyclo[2.2.1]hepto-2-ene (5-isopropenyl-2-norbornene); 5-vinyl-4-vinylbicyclo[2.2.1]hepto-2-ene (5-vinyl-4-vinyl-2-norbornene); 5-propenyl-bicyclo[2.2.1]hepto-2-ene (5-propenyl-2-norbornene); 5-butenyl-bicyclo[2.2.1]hepto-2-ene (5-butenyl-2-norbornene; 5-pentenyl-bicyclo[2.2.1]hepto-2-ene (5-pentenyl-2-norbornene); and their monomethyl, monochloro, and dichloro substituents, including the endo and exo isomers, and mixtures thereof. More preferred 5-alkenyl-2-norbornene(s) include 5-vinyl-2-norbornene, 5-isopropenyl-2-noborbornene, 5-propenyl-2-norbornene, and 5-butenyl-2-norbornene, including the endo and exo isomers, and mixtures thereof. The most preferred 5-alkenyl-2-norborne pot life adjusting agent is 5-vinyl-2-norbornene, including the endo and exo isomers, and mixtures thereof. 5-alkenyl-2-norbornene pot life adjusting agents are normally employed in the resin composition at levels of about 0.01 phr to 10 phr, more preferably at levels of about 0.1 phr to 5 phr, even more preferably at levels of about 0.1 phr to 3 phr. 5-alkenyl-2-norborne pot life adjusting agents may be added to the resin composition in the absence of solvent, or as organic solutions. A single 5-alkenyl-2-norborne pot life adjusting agent may be used as a pot life adjusting agent, or a combination of two or more different 5-alkenyl-2-norbornene pot life adjusting agents may be used.

Resin compositions of the invention may be optionally formulated with additives. Suitable additives include, but are not limited to, gel modifiers, hardness modulators, impact modifiers, elastomers, antioxidants, antiozonants, stabilizers, crosslinkers, fillers, binders, coupling agents, thixotropes, wetting agents, biocides, plasticizers, pigments, flame retardants, dyes, fibers and reinforcement materials, including sized reinforcements and substrates, such as those treated with finishes, coatings, coupling agents, film formers and/or lubricants. Furthermore, the amount of additives present in the resin compositions may vary depending on the particular type of additive used. The concentration of the additives in the resin compositions typically ranges from, for example, 0.001-85 percent by weight, particularly, from 0.1-75 percent by weight, or even more particularly, from 2-60 percent by weight.

Resin compositions of the invention may additionally comprise a crosslinker, for example, a crosslinker selected from dialkyl peroxides, diacyl peroxides, and peroxyacids. Examples of such crosslinkers are disclosed in U.S. Pat. No. 5,728,785, the contents of which are incorporated herein by reference.

In another embodiment, resin compositions of the invention may additionally comprise at least one crosslinking monomer. Examples of crosslinking monomers include: fused multicyclic ring systems and linked multicyclic ring systems, as described in International Patent Application WO0276613A1 and in U.S. Pat. No. 6,281,307B1.

In another embodiment, resin compositions of the invention may additionally comprise at least one impact modifier. Suitable impact modifiers or elastomers include without limitation natural rubber, butyl rubber, polyisoprene, polybutadiene, polyisobutylene, ethylene-propylene copolymer, styrene-butadiene-styrene triblock rubber, random styrene-butadiene rubber, styrene-isoprene-styrene triblock rubber, styrene-ethylene/butylene-styrene copolymer, styrene-ethylene/propylene-styrene copolymer, ethylene-propylene-diene terpolymers, ethylene-vinyl acetate, and nitrile rubbers. Preferred impact modifiers or elastomers are polybutadiene Diene 55AC10 (Firestone), polybutadiene Diene 55AM5 (Firestone), EPDM Royalene 301T, EPDM Buna T9650 (Bayer), styrene-ethylene/butylene-styrene copolymer Kraton G1651H, Polysar Butyl 301 (Bayer), polybutadiene Taktene 710 (Bayer), styrene-ethylene/butylene-styrene Kraton G1726M, Ethylene-Octene Engage 8150 (DuPont- Dow), styrene-butadiene Kraton D1184, EPDM Nordel 1070 (DuPont-Dow), and polyisobutylene Vistanex MML-140 (Exxon), hydrogenated styrene-ethylene/butylene-styrene copolymer Kraton G1650M, hydrogenated styrene-ethylene/butylene-styrene copolymer Kraton G1657M, and styrene-butadiene block copolymer Kraton D1101, impact modifiers according to the invention generally manufactured by Addivant™ sold under the trade names of Royaltuf® (e.g., Royaltuf® 498, Royaltuf® 485) or high performance elastomers manufactured by Kraton Polymers sold under the trade names of Kraton® (e.g., Kraton® G1650, Kraton® G1652, Kraton® FG1901, Kraton® FG1924). Such materials are normally employed in the resin composition at levels of about 0.10 phr to 10 phr, but more preferably at levels of about 0.1 phr to 5 phr. Various polar impact modifiers or elastomers can also be used.

In another embodiment, resin compositions of the invention may additionally comprise at least one antioxidant. In another embodiment, resin compositions of the invention may additionally comprise at least one antiozonant. Antioxidants and antiozonants include any antioxidant or antiozonant used in the rubber or plastics industry. An "Index of Commercial Antioxidants and Antiozonants, Fourth Edition" is available from Goodyear Chemicals, The Goodyear Tire and Rubber Company, Akron, Ohio 44316. Suitable stabilizers (i.e., antioxidants or antiozonants) include without limitation: 2,6-di-tert-butyl-4-methylphenol (BHT); styrenated phenol, such as Wingstay® S (Goodyear); 2- and 3-tert-butyl-4-methoxyphenol; alkylated hindered phenols, such as Wingstay C (Goodyear); 4-hydroxymethyl-2,6-di-tert-butylphenol; 2,6-di-tert-butyl-4-sec-butylphenol; 2,2'-methylenebis(4-methyl-6-tert-butylphenol); 2,2'-methylenebis(4-ethyl-6-tert-butylphenol); 4,4'-methylenebis(2,6-di-tert-butylphenol); miscellaneous bisphenols, such as Cyanox® 53 (Cytec Industries Inc.) and Permanax WSO; 2,2'-ethylidenebis(4,6-di-tert-butylphenol); 2,2'-methylenebis(4-methyl-6-(1-methylcyclohexyl)phenol); 4,4'-butylidenebis(6-tert-butyl-3-methylphenol); polybutylated Bisphenol A; 4,4'-thiobis(6-tert-butyl-3-methylphenol); 4,4'-methylenebis(2,6-dimethylphenol); 1,1'-thiobis(2-naphthol); methylene bridged polyaklylphenol, such as Ethyl antioxidant 738; 2,2'-thiobis(4-methyl-6-tert-butylphenol); 2,2'-isobutylidenebis(4,6-dimethylphenol); 2,2'-methylenebis(4-methyl-6-cyclohexylphenol); butylated reaction product of p-cresol and dicyclopentadiene, such as Wingstay L; tetrakis(methylene-3,5-di-tert-butyl-4-hydroxyhydrocinnamate)methane, i.e., Irganox® 1010 (BASF); 1,3,5-trimethyl-2,4,6-tris(3,5-di-tert-butyl-4-hydroxybenzyl)benzene, e.g., Ethanox®330 (Albemarle Corporation); 4,4'-methylenebis (2,6-di-tertiary-butylphenol), e.g., Ethanox 4702 or Ethanox 4710; 1,3,5-tris(3,5-di-tert-butyl-4-hydroxybenzyl)isocyanurate, i.e., Good-Rite® 3114 (Emerald Performance Materials), 2,5-di-tert-amylhydroquinone, tert-butylhydroquinone, tris(nonylphenylphosphite), bis(2,4-di-tert-butyl)pentaerythritol)diphosphite, distearyl pentaerythritol diphosphite, phosphited phenols and bisphenols, such as Naugard® 492 (Chemtura Corporation), phosphite/phenolic antioxidant blends, such as Irganox B215; di-n-octadecyl(3,5-di-tert-butyl-4-hydroxybenzyl) phosphonate, such as Irganox 1093; 1,6-hexamethylene bis (3-(3,5-di-tert-butyl-4-hydroxyphenylpropionate), such as Irganox 259, and octadecyl-3,5-di-tert-butyl-4-hydroxyhydrocinnamate, i.e., Irganox 1076, tetrakis(2,4-di-tert-butylphenyl)4,4'-biphenylylenediphosp honite, diphenylamine, and 4,4'-diemthoxydiphenylamine. Antioxidants and/or antiozonants are normally employed in the resin composition at levels of about 0.10 phr to 10 phr, but more preferably at levels of about 0.1 phr to 5 phr.

In another embodiment, resin compositions of the invention may further comprise at least one filler. Suitable fillers include, for example, metallic density modulators, microparticulate density modulators, organic fillers, inorganic fillers, such as, for example, microspheres, and macroparticulate density modulators, such as, for example, glass or ceramic beads. Metallic density modulators include, but are not limited to, powdered, sintered, shaved, flaked, filed, particulated, or granulated metals, metal oxides, metal nitrides, and/or metal carbides, and the like. Preferred metallic density modulators include, among others, tungsten, tungsten carbide, aluminum, titanium, iron, lead, silicon oxide, aluminum oxide, boron carbide, and silicon carbide. Microparticulate density modulators include, but are not limited to, glass, metal, thermoplastic (either expandable or pre-expanded) or thermoset, and/or ceramic/silicate microspheres. Macroparticulate density modulators include, but are not limited to, glass, plastic, or ceramic beads; metal rods, chunks, pieces, or shot; hollow glass, ceramic, plastic, or metallic spheres, balls, or tubes; and the like. Organic fillers include, but are not limited to, powedered, particules, flakes, flour, shells, of polytetrafluoroethylene, polyethylene, polyethylene ultra high molecular weight (PE-UHMWPE), polypropylene, polystyrene, acrylic, polyamides, aromatic polyamides, aramid fibers, carbon nanotubes, carbon fibers, graphite, carbon black, polysulfone, polyethersulfone, polyphenylsulfone, fluorinates etheylene proppylene (FEP), polyether ethyl ketone (PEEK), polyvinylidene fluoride, polyamide imide, polyester, cellulose fibers, wood flour, wood fibers. Inorganic fillers include, but are not limited to, powedered, particules, flakes, flour, shells, fibers of aluminum trihydrate, barium sulfate, calcium sulfate, calcium carbonate, phosphates, talc, clay, mica, montmorillonite, molybdenum disulfide ($MoS_2$), tungsten disulfide ($WS_2$), boron nitrate, glass, silicates, aluminosilicates, magnesium oxide, zinc oxide, wollastonite, barite.

In another embodiment, resin compositions of the invention may further comprise at least one reinforcing material. Suitable reinforcing materials include those that add to the strength or stiffness of a polymer composite when incorporated with the polymer. Reinforcing materials can be in the form of filaments, fibers, rovings, mats, weaves, fabrics, knitted material, cloth, or other known structures. Suitable reinforcement materials include glass fibers and fabrics, carbon fibers and fabrics, aramid fibers and fabrics, polyolefin fibers or fabrics (including ultrahigh molecular weight polyethylene fabrics such as those produced by Honeywell under the Spectra® trade name), and polyoxazole fibers or fabrics (such as those produced by the Toyobo Corporation under the Zylon® trade name). Reinforcing materials containing surface finishes, sizings, or coatings are particularly suitable for the described invention including Ahlstrom glass roving (R338-2400), Johns Manville glass roving (Star ROV®-086), Owens Corning rovings (OCV 366-AG-207, R25H-X14-2400, SE1200-207, SE1500-2400, SE2350-250), PPG glass rovings (Hybon® 2002, Hybon® 2026), Toho Tenax® carbon fiber tow (HTR-40), and Zoltek carbon fiber tow (Panex® 35). Furthermore, any fabrics prepared using reinforcing materials containing surface finishes, sizings or coatings are suitable for the invention. Advantageously, the invention does not require the expensive process of removing of surface finishes, sizings, or coatings from the reinforcing materials. Additionally, glass fibers or fabrics may include without limitation A-glass, E-glass or S-glass, S-2 glass, C-glass, R-glass, ECR-glass, M-glass, D-glass, and quartz, and silica/quartz. Preferred glass fiber reinforcements are those with finishes formulated for use with epoxy, vinyl ester, and/or polyurethane resins. When formulated for use with a combination of these resin types, the reinforcements are sometimes described as "multi-compatible." Such reinforcements are generally treated during their manufacture with organosilane coupling agents comprising vinyl, amino, glycidoxy, or methacryloxy functional groups (or various combinations thereof) and are coated with a finish to protect the fiber surface and facilitate handling and processing (e.g., spooling and weaving). Finishes typically comprise a mixture of chemical and polymeric compounds such as film formers, surfactants, and lubricants. Especially preferred glass reinforcements are those containing some amount of amino-functionalized silane coupling agent. Especially preferred finishes are those comprising and epoxy-based and/or polyurethane-based film formers. Examples of preferred glass-fiber reinforcements are those based on Hybon® 2026, 2002, and 2001 (PPG) multi-compatible rovings; Ahlstrom R338 epoxysilane-sized rovings; StarRov® 086 (Johns Manville) soft silane sized multi-compatible rovings; OCV™ 366, SE 1200, and R25H (Owens Corning) multi-compatible rovings; OCV™ SE 1500 and 2350 (Owens Corning) epoxy-compatible rovings; and Jushi Group multi-compatible glass rovings (752 type, 396 type, 312 type, 386 type). Additional suitable polymer fibers and fabrics may include without limitation one or more of polyester, polyamide (for example, NYLON polamide available from E.I. DuPont, aromatic polyamide (such as KEVLAR aromatic polyamide available from E.I. DuPont, or P84 aromatic polyamide available from Lenzing Aktiengesellschaft), polyimide (for example KAPTON polyimide available from E.I. DuPont, polyethylene (for example, DYNEEMA polyethylene from Toyobo Co., Ltd.). Additional suitable carbon fibers may include without limitation AS2C, AS4, AS4C, AS4D, AS7, IM6, IM7, IM9, and PV42/850 from Hexcel Corporation; TORAYCA T300, T300J, T400H, T600S, T700S, T700G, T800H, T800S, T1000G, M35J, M40J, M46J, M50J, M55J, M60J, M30S, M30G and M40 from Toray Industries, Inc.; HTS12K/24K, G30-500 3k/6K/12K, G30-500 12K, G30-700 12K, G30-7000 24K F402, G40-800 24K, STS 24K, HTR 40 F22 24K 1550tex from Toho Tenax, Inc.; 34-700, 34-700WD, 34-600, 34-600WD, and 34-600 unsized from Grafil Inc.; T-300, T-650/35, T-300C, and T-650/35C from Cytec Industries. Additionally suitable carbon fibers may include without limitation AKSACA (A42/D011), AKSACA (A42/D012), Blue Star Starafil (10253512-90), Blue Star Starafil (10254061-130), SGL Carbon (C30 T050 1.80), SGL Carbon (C50 T024 1.82), Grafil (347R1200U), Grafil (THR 6014A), Grafil (THR 6014K), Hexcel Carbon (AS4C/EXP 12K), Mitsubishi (Pyrofil TR 50S 12L AF), Mitsubishi (Pyrofil TR 50S 12L AF), Toho Tenax (T700SC 12000-50C), Toray (T700SC 12000-90C), Zoltek (Panex 35 50K, sizing 11), Zoltek (Panex 35 50K, sizing 13). Additional suitable carbon fabrics may include without limitation Carbon fabrics by Vectorply (C-L 1800) and Zoltek (Panex 35 UD Fabic-PX35UD0500-1220). Additionally suitable glass fabrics may include without limitation glass fabrics as supplied by Vectorply (E-LT 3500-10) based on PPG Hybon® 2026; Saertex (U14EU970-01190-T2525-125000) based on PPG Hybon® 2002; Chongqing Polycomp International Corp. (CPIC® Fiberglass) (EKU 1150(0)/50-600); and Owens Corning (L1020/07A06 Xweft 200tex).

Resin compositions according to the invention may further comprise a sizing composition, or be used to provide improved adhesion to substrate materials that are sized with certain commercial silanes commonly used in the industry. As is known in the art, glass fibers are typically treated with a chemical solution (e.g., a sizing composition) soon after their formation to reinforce the glass fibers and protect the strands' mechanical integrity during processing and composite manufacture. Sizing treatments compatible with olefin metathesis catalysts and polydicyclopentadiene composites have been described in U.S. Pat. Nos. 6,890,650 and 6,436,476, the disclosures of both of which are incorporated herein by reference. However, these disclosures are based on the use of specialty silane treatments that are not commonly used in industrial glass manufacture. By comparison, the current invention may provide improved mechanical properties for polymer-glass composites that are sized with silanes commonly used in the industry.

Glass sizing formulations typically comprise at least one film former (typically a film forming polymer), at least one silane, and at least one lubricant. Any components of a sizing formulation that do not interfere with or substantially decrease the effectiveness of the metathesis catalyst or olefin polymerization reaction are considered to be compatible with the current invention and may generally be used herein.

Film formers that are compatible with ROMP catalysts include epoxies, polyesters, polyurethanes, polyolefins, and/or polyvinyl acetates. Other common film formers that do not adversely affect the performance of the olefin metathesis catalyst may also be used. Film formers are typically used as nonionic, aqueous emulsions. More than one film former may be used in a given sizing formulation, to achieve a desired balance of glass processability and composite mechanical properties.

More particularly, the film former may comprise a low molecular weight epoxy emulsion, defined as an epoxy monomer or oligomer with an average molecular weight per epoxide group (EEW) of less than 500, and/or a high molecular weight epoxy emulsion, defined as an epoxy monomer or oligomer with an average molecular weight per epoxide group (EEW) of greater than 500. Examples of suitable low molecular weight products include aqueous epoxy emulsions produced by Franklin International, including Franklin K8-0203 (EEW 190) and Franklin E-102 (EEW 225-275). Other examples of low molecular weight epoxy emulsions are available from Hexion, including EPI-REZ™ 3510-W-60 (EEW 185-215), and EPI-REZ™ 3515-W-60 (EEW 225-275). Further examples of low molecular weight epoxy emulsions are available from COIM, including Filco 309 (EEW 270) and Filco 306 (EEW 330). Further examples of low molecular weight epoxy emulsions are available from DSM, including Neoxil®965 (EEW 220-280) and Neoxil® 4555 (EEW 220-260). Examples of suitable high molecular weight epoxy emulsion products include epoxy emulsions produced by Hexion, including EPI-REZ™ 3522-W-60 (EEW 615-715).

Aqueous emulsions of modified epoxies, polyesters, and polyurethanes may also be used in the film former. Examples of suitable modified epoxy products include emulsions produced by DSM, including Neoxil® 2626 (a plasticized epoxy with an EEW of 500-620), Neoxil® 962/D (an epoxy-ester with an EEW of 470-550), Neoxil® 3613 (an epoxy-ester with an EEW of 500-800), Neoxil® 5716 (an epoxy-novolac with an EEW of 210-290), Neoxil® 0035 (a plasticized epoxy-ester with an EEW of 2500), and Neoxil® 729 (a lubricated epoxy with an EEW of 200-800). Further examples of modified epoxy emulsions are available from COIM, including Filco 339 (an unsaturated polyester-epoxy with an EEW of 2000) and Filco 362 (an epoxy-ester with an EEW of 530). Examples of suitable polyester products include emulsions produced by DSM, including Neoxil® 954/D, Neoxil® 2635, and Neoxil® 4759 (unsaturated bisphenolic polyesters). Additional suitable products from DSM include Neoxil® 9166 and Neoxil® 968/60 (adipate polyesters). Further examples of suitable products include emulsions produced by COIM, including Filco 354/N (unsaturated bisphenolic polyester), Filco 350 (unsaturated polyester), and Filco 368 (saturated polyester). Examples of suitable polyurethane products include emulsions produced by Bayer Material Science, including Baybond® 330 and Baybond® 401.

The film former may also comprise polyolefins or polyolefin-acrylic copolymers, polyvinylacetates, modified polyvinylacetates, or polyolefin-acetate copolymers. Suitable polyolefins include, but are not limited to, polyethylenes, polypropylenes, polybutylenes, and copolymers thereof, and the polyolefins may be oxidized, maleated, or otherwise treated for effective film former use. Examples of suitable products include emulsions produced by Michelman, including Michem® Emulsion 91735, Michem® Emulsion 35160, Michem® Emulsion 42540, Michem® Emulsion 69230, Michem® Emulsion 34040M1, Michem® Prime 4983R, and Michem® Prime 4982SC. Examples of suitable products include emulsions produced by HB Fuller, including PD 708H, PD 707, and PD 0166. Additional suitable products include emulsions produced by Franklin International, including Duracet® 637. Additional suitable products include emulsions produced by Celanese, including Vinamul® 8823 (plasticized polyvinylacetate), Dur-O-Set® E-200 (ethylene-vinyl acetate copolymer), Dur-O-Set® TX840 (ethylene-vinyl acetate copolymer), and Resyn® 1971 (epoxy-modified polyvinylacetate).

While not limited thereto, preferred film formers include low- and high-molecular weight epoxies, saturated and unsaturated polyesters, and polyolefins, such as Franklin K80-203, Franklin E-102, Hexion 3510-W-60, Hexion 3515-W-60, and Michelman 35160.

Nonionic lubricants may also be added to the sizing composition. Suitable nonionic lubricants that are compatible with ROMP compositions include esters of polyethylene glycols and block copolymers of ethylene oxide and propylene oxide. More than one nonionic lubricant may be used in a given sizing formulation if desired, e.g., to achieve a desired balance of glass processability and composite mechanical properties.

Suitable lubricants may contain polyethylene glycol (PEG) units with an average molecular weight between 200 and 2000, preferably between 200-600. These PEG units can be esterified with one or more fatty acids, including oleate, tallate, laurate, stearate, and others. Particularly preferred lubricants include PEG 400 dilaurate, PEG 600 dilaurate, PEG 400 distearate, PEG 600 distearate, PEG 400 dioleate, and PEG 600 dioleate. Examples of suitable products include compounds produced by BASF, including MAPEG® 400 DO, MAPEG® 400 DOT, MAPEG® 600 DO, MAPEG® 600 DOT, and MAPEG® 600 DS. Additional suitable products include compounds produced by Zschimmer & Schwarz, including Mulsifan 200 DO, Mulsifan 400 DO, Mulsifan 600 DO, Mulsifan 200 DL, Mulsifan 400 DL, Mulsifan 600 DL, Mulsifan 200 DS, Mulsifan 400 DS, and Mulsifan 600 DS. Additional suitable products include compounds produced by Cognis, including Agnique® PEG 300 DO, Agnique® PEG 400 DO, and Agnique® PEG 600 DO.

Suitable nonionic lubricants also include block copolymers of ethylene oxide and propylene oxide. Examples of suitable products include compounds produced by BASF, including Pluronic® L62, Pluronic® L101, Pluronic® P103, and Pluronic® P105.

Cationic lubricants may also be added to the sizing composition. Cationic lubricants that are compatible with ROMP include modified polyethyleneimines, such as Emery 6760L produced by Pulcra Chemicals.

Silane coupling agent may optionally be added to the sizing composition, non-limiting examples including, methacrylate, acrylate, amino, or epoxy functionalized silanes along with alkyl, alkenyl, and norbornenyl silanes.

Optionally, the sizing composition may contain one or more additives for modifying the pH of the sizing resin. One preferred pH modifier is acetic acid.

The sizing composition may optionally contain other additives useful in glass sizing compositions. Such additives may include emulsifiers, defoamers, cosolvents, biocides, antioxidants, and additives designed to improve the effectiveness of the sizing composition. The sizing composition can be prepared by any method and applied to substrate materials for use herein, such as glass fibers or fabric, by any technique or method.

In another embodiment, resin compositions of the invention may additionally comprise at least one adhesion promoter. One class of adhesion promoters for use in the present invention are disclosed in International Pat. App. No. PCT/US2012/042850, the contents of which are also incorporated herein by reference. Non-limiting examples of adhesion promoters that may be used in the present invention disclosed herein are generally compounds containing at least two isocyanate groups (such as, for example, methylene diphenyl diisocyanate and hexamethylene diisocyanate). The adhesion promoter may be a diisocyanate, triisocyanate, or polyisocyanate (i.e., containing four or more isocyanate groups). The adhesion promoter may be a mixture of at least one diisocyanate, triisocyanate, or polyisocyanate. In a more particular aspect of the invention, the adhesion promoter comprises, or is limited to, a diisocyanate compound, or mixtures of diisocyanate compounds.

In general, adhesion promoters that may be used in the present invention may be any compound having at least two isocyanate groups. Suitable adhesion promoters include, without limitation, isocyanate compounds comprising at least two isocyanate groups, and wherein the compounds are selected from hydrocarbyl, substituted hydrocarbyl, heteroatom-containing hydrocarbyl, substituted heteroatom-containing hydrocarbyl, and functionalized hydrocarbyl compounds. As described above, suitable hydrocarbyl adhesion promoter compounds generally include alkyl, cycloalkyl, alkylene, alkenyl, alkynyl, aryl, cycloalkyl, alkaryl, and aralkyl compounds. Substituted heteroatom-containing, and functionalized hydrocarbyl adhesion promoter compounds include the afore-mentioned hydrocarbyl compounds, as well as the variations thereof noted hereinabove.

Adhesion promoters that may be used in the present invention may be an alkyl diisocyanate. An alkyl diisocyanate refers to a linear, branched, or cyclic saturated or unsaturated hydrocarbon group typically although not necessarily containing 1 to about 24 carbon atoms, preferably a diisocyanate containing 2 to about 12 carbon atoms, and more preferably a diisocyanate containing 6 to 12 carbon atoms such as hexamethylene diisocyanate (HDI), octamethylene diisocyanate, decamethylene diisocyanate, and the like. Cycloalkyl diisocyanates contain cyclic alkyl group, typically having 4 to 16 carbon atoms. A preferred cycloalkyl diisocyanate containing 6 to about 12 carbon atoms are cyclohexyl, cyclooctyl, cyclodecyl, and the like. A more preferred cycloalkyl diisocyanate originates as a condensation product of acetone called 5-isocyanato-1-(isocyanatomethyl)-1,3,3-trimethyl-cyclohexane, commonly known as Isophorone diisocyanate (IPDI) and the isomers of isocyanato-[(isocyanatocyclohexyl)methyl]cyclohexane ($H_{12}$MDI). $H_{12}$MDI is derived from the hydrogenated form of the aryl diisocyanate methylene diphenyl diisocyanate (MDI).

Adhesion promoters that may be used in the present invention may be an aryl diisocyanate. Aryl diisocyanates refers to aromatic diisocyanates containing a single aromatic ring or multiple aromatic rings that are fused together, directly linked, or indirectly linked (such that the different aromatic rings are bound to a common group such as a methylene or ethylene moiety). Preferred aryl diisocyanates contain 5 to 24 carbon atoms, and particularly preferred aryl diisocyanates contain 5 to 14 carbon atoms. Exemplary aryl diisocyanates contain one aromatic ring or two fused or linked aromatic rings, e.g., phenyl, tolyl, xylyl, naphthyl, biphenyl, diphenylether, benzophenone, and the like. Preferred aromatic diisocyanates include toluene diisocyanates, tetramethylxylene diisocyanate (TMXDI), and methylene diphenyl diisocyanate (MDI), which may comprise any mixture of its three isomers, 2.2'-MDI, 2,4'-MDI, and 4,4'-MDI.

Adhesion promoters that may be used in the present invention may be a polymer-containing isocyanate, such as, for example, diisocyanates. Polymer-containing isocyanates refers to a polymer-containing two or more terminal and/or pendant alkyl or aryl isocyanate groups. The polymer-containing isocyanates generally have to have a minimal solubility in the resin to provide improved mechanical properties. Preferred polymer-containing isocyanates include, but are not limited to, PM200 (poly MDI), Lupranate® (poly MDI from BASF), Krasol® isocyanate terminated polybutadiene prepolymers, such as, for example, Krasol® LBD2000 (TDI based), Krasol® LBD3000 (TDI based), Krasol® NN-22 (MDI based), Krasol® NN-23 (MDI based), Krasol® NN-25 (MDI based), and the like. Krasol® isocyanate terminated polybutadiene prepolymers are available from Cray Valley.

Adhesion promoters that may be used in the present invention may be a trimer of alkyl diisocyanates and aryl diisocyanates. In its simplest form, any combination of polyisocyanate compounds may be trimerized to form an isocyanurate ring containing isocyanate functional groups. Trimers of alkyl diisocyanate and aryl diisocyanates may also be referred to as isocyanurates of alkyl diisocyanate or aryl diisocyanate. Preferred alkyl diisocyanate and aryl diisocyanate trimers include, but are not limited to, hexamethylene diisocyanate trimer (HDIt), isophorone diisocyanate trimer, toluene diisocyanate trimer, tetramethylxylene diisocyanate trimer, methylene diphenyl diisocyanate trimers, and the like. More preferred adhesion promoters are toluene diisocyanates, tetramethylxylene diisocyanate (TMXDI), and methylene diphenyl diisocyanate (MDI) including any mixture of its three isomers 2.2'-MDI, 2,4'-MDI and 4,4'-MDI; liquid MDI; solid MDI; hexamethylenediisocyanatetrimer (HDIt); hexamethylenediisocyanate (HDI); isophorone diisocyanate (IPDI); 4,4'-methylene bis (cyclohexyl isocyanate) (H12MDI); polymeric MDI (PM200); MDI prepolymer (Lupranate®5080); liquid carbodiimide modified 4,4'-MDI (Lupranate® MM103); liquid MDI (Lupranate® MI); liquid MDI (Mondur® ML); and liquid MDI (Mondur® MLQ). Even more preferred adhesion promoters are methylene diphenyl diisocyanate (MDI) including any mixture of its three isomers 2,2'-MDI, 2,4'-MDI and 4,4'-MDI; liquid MDI; solid MDI; hexamethylenediisocyanatetrimer (HDIt); hexamethylene diisocyanate (HDI); isophorone diisocyanate (IPDI); 4,4'-methylene bis (cyclohexyl isocyanate) (H12MDI); polymeric MDI (PM200); MDI prepolymer (Lupranate® 5080); liquid carbodiimide modified 4,4'-MDI (Lupranate® MM103); liquid MDI) (Lupranate® MI); liquid MDI (Mondur® ML); liquid MDI (Mondur® MLQ).

Any concentration of adhesion promoter which improves the mechanical properties of the olefin composite (e.g. ROMP polymer composite) is sufficient for the invention. In general, suitable amounts of adhesion promoter range from 0.001-50 phr, particularly 0.05-10 phr, more particularly 0.1-10 phr, or even more particularly 0.5-4.0 phr. One or more adhesion promoters may be used in the present invention.

Additional adhesion promoters suitable for use in the present invention comprise functionalized silanes of the formula $Fn-(A)_n-Si(Y^*)_3$, wherein $Y^*$ is selected from halide (preferably chloride) or OR; Fn is a functional group selected from acrylate, methacrylate, allyl, vinyl, alkene, cycloalkene, or norbornene; A is a divalent linking group selected from hydrocarbylene, substituted hydrocarbylene, heteroatom-containing hydrocarbylene, or substituted heteroatom-containing hydrocarbylene; n is 0 or 1; and R is selected from hydrocarbyl, substituted hydrocarbyl, heteroatom-containing hydrocarbyl, or substituted heteroatom-containing hydrocarbyl, preferably lower alkyl, more preferably methyl, ethyl, or isopropyl; and a peroxide selected from dialkyl and diaryl peroxides.

Additional adhesion promoters for use in the present invention and methods for their use include those disclosed in International Pat. App. No. PCT/US00/03002, the contents of which are incorporated herein by reference.

Articles may include, but are not limited to, those formed by standard manufacturing techniques including casting, centrifugal casting, pultrusion, molding, rotational molding, open molding, reaction injection molding (RIM), resin transfer molding (RTM), pouring, vacuum impregnation, surface coating, filament winding and other methods known to be useful for production of polymer articles and/or polymer composite articles. Furthermore, the compositions and articles of manufacture of the invention are not limited to a single polymer-surface interface but include also multilayers and laminates containing multiple polymer-surface interfaces. The invention is also suitable for manufacture of articles by the infusion of the resin into a porous material. Such porous materials include but are not limited to wood, cement, concrete, open-cell and reticulated foams and sponges, papers, cardboards, felts, ropes or braids of natural or synthetic fibers, and various sintered materials. Additionally, other manufacturing techniques include without limitation cell casting, dip casting, continuous casting, embedding, potting, encapsulation, film casting or solvent casting, gated casting, mold casting, slush casting, extrusion, mechanical foaming, chemical foaming, physical foaming, compression molding or matched die molding, spaying, spray up, Vacuum Assisted Resin Transfer Molding (VARTM), Seeman's Composite Resin Infusion Molding Process (SCRIMP), blow molding, in mold coating, in-mold painting or injection, vacuum forming, Reinforced Reaction Injection Molding (RRIM), Structural Reaction Injection Molding (SRIM), thermal expansion transfer molding (TERM), resin injection recirculation molding (RICM), controlled atmospheric pressure resin infusion (CAPRI), hand-layup. For manufacturing techniques requiring the use of a RIM or impingement style mixhead, including without limitation RIM, SRIM, and RRIM, articles of manufacture may be molded using a single mixhead or a plurality of mixheads as well as a plurality of material injection streams (e.g., two resin streams and one catalyst stream). As the invention allows for increasingly faster cycle times and increasingly higher mold temperatures using any of the aforementioned manufacturing techniques, particularly mold temperatures above 90° C., it may become necessary to mold ROMP compositions of the invention under high pressures or under vacuum to prevent defects caused by mixing issues and/or entrapped gases.

Furthermore, the present invention also allows for the making of articles of manufacture of any configuration, weight, size, thickness, or geometric shape. Examples of articles of manufacture include without limitation any molded or shaped article for use as an aerospace component, a marine component, an automotive component, a sporting goods component, an electrical component, and industrial component, medical component, dental component, or military component. In one embodiment an article may be a turbine component used on aircraft or general power generation. In one embodiment, turbine components may include without limitation one or more of an inlet, pylon, pylon fairing, an acoustic panel, a thrust reverser panel, a fan blade, a fan containment case, a bypass duct, an aerodynamic cowl, or an airfoil component. In one embodiment, an article may be a turbine blade component or may be a turbine blade. In one embodiment, an article may be a wind rotor blade, tower, spar cap, or nacelle for wind turbines. In one embodiment, an article may be an airframe component. Examples of aerospace components may include without limitation one or more of fuselage skin, wing, fairing, doors, access panel, aerodynamic control surface, or stiffener. In one embodiment an article may be an automotive component. Examples of automotive components may include without limitation one or more of body panel, fender, spoiler, truck bed, protective plate, hood, longitudinal rail, pillar, or door. Examples of industrial components may include without limitation one or more of risers platforms, impact protection structures for oil and gas; bridges, pipes, pressure vessels, power poles, coils, containers, tanks, liners, containment vessels, articles for application in corrosive environments (e.g., chlor-alkali, caustic, acidic, brine, etc.), centralizers (e.g. oilfield centralizer), electrolytic cell covers, reinforcement structures for concrete architectures and roads, or radiators. Examples of electrical components may include without limitation one or more wound articles, such as coils or electric motors, or insulating devices. In one embodiment, an article may be an eddy-current shielding component of a magnetic resonance imaging system or shielding component for any electromagnetic radiation. In one embodiment, an article may be a military component including without limitation ballistics resistant armor for personnel or vehicles, or ballistics resistant structures for protecting personnel or equipment. In one embodiment, an article may be a sporting goods component including without limitation an arrow shaft, a tennis racket frame, a hockey stick, compound bow limbs, or a golf club shaft. In one embodiment, an article may be an object used in offshore applications, where the object is at least partially coated with a ROMP composition of the invention, where the object includes but is not limited to pipes, pipelines, pipe fittings, hoses, hose fittings, tanks, containers, drums, manifolds, risers, field joints, configurations designated as Christmas trees (oil field Christmas tree, subsea Christmas tree), jumpers, spool pieces, configurations designated as pipeline end termination (PLET), configurations designated as pipeline end manifolds (PLEM), robotic parts, devices and vehicles used in sub-sea applications, configurations designated as subsea dog houses, and other sub-sea architectures and equipment. Other non-limiting examples of offshore applications include insulation materials (e.g., thermal insulation) and field joint coating material.

In a preferred embodiment, the metathesis reactions disclosed herein are carried out under a dry, inert atmosphere. Such an atmosphere may be created using any inert gas, including such gases as nitrogen and argon. The use of an inert atmosphere is optimal in terms of promoting catalyst activity, and reactions performed under an inert atmosphere typically are performed with relatively low catalyst loading. The reactions disclosed herein may also be carried out in an oxygen-containing and/or a water-containing atmosphere, and in one embodiment, the reactions are carried out under ambient conditions. The presence of oxygen or water in the reaction may, however, necessitate the use of higher catalyst loadings as compared with reactions performed under an inert atmosphere. Where the vapor pressure of the reactants allows, the reactions disclosed herein may also be carried out under reduced pressure.

The reactions disclosed herein may be carried out in a solvent, and any solvent that is inert towards cross-metathesis may be employed. Generally, solvents that may be used in the metathesis reactions include organic, protic, or aqueous solvents, such as aromatic hydrocarbons, chlorinated hydrocarbons, ethers, aliphatic hydrocarbons, alcohols, water, or mixtures thereof. Example solvents include benzene, toluene, p-xylene, methylene chloride, 1,2-dichloroethane, dichlorobenzene, chlorobenzene, tetrahydrofuran, diethyl ether, pentane, methanol, ethanol, water, or mixtures thereof. In a preferred embodiment, the reactions disclosed herein are carried out neat, i.e., without the use of a solvent.

It will be appreciated that the temperature at which a metathesis reaction according to methods disclosed herein is conducted can be adjusted as needed over a wide range of temperatures. With highly active metathesis catalysts, olefin metathesis may occur at temperatures as low as −78° C. With increasingly latent catalysts, olefin metathesis may not be observed until temperatures of −40° C., −10° C., 0° C., 10° C., 20° C., 25° C., 35° C., 50° C., 70° C., 100° C., or 150° C. In one embodiment, the reactions are carried out at a temperature of at least about 35° C., and in another embodiment, the reactions are carried out at a temperature of at least about 50° C. In certain embodiments, a mold or preform may be filled with resin and catalyst at a temperature near room temperature (e.g., about 10-45° C., or preferably 15-40° C., or more preferably 20-35° C.) and then heated over a period time to a higher temperature (e.g., about 50-200° C., or preferably 70-150° C., or more preferably 90-120° C.) to allow polymerization to complete more quickly. In certain embodiments, a mold or preform may be preheated to a temperature considerably above room temperature (e.g., about 50-250° C., or about 50-200° C., or about 50-150° C., or about 40-80° C., or about 40-60° C., or about 60-80° C., or about 50-100° C., or about 100-150° C., or about 150-200° C.) and then filled quickly with resin and catalyst to allow for fast cycle times.

EXPERIMENTAL

General Information—Materials and Methods

In the following examples, efforts have been made to ensure accuracy with respect to numbers used (e.g., amounts, temperature, etc.) but some experimental error and deviation should be accounted for. The examples are to be considered as not being limiting of the invention described herein.

All reactions involving metal complexes were conducted in oven-dried glassware under an argon or nitrogen atmosphere using standard Schlenk techniques. Chemicals and solvents were obtained from Sigma-Aldrich, Strem, Alfa Aesar, Nexeo, Brenntag, AG Layne and TCI. Commercially available reagents were used as received unless otherwise noted. Silica gel was purchased from Fisher (0.040-0.063 m, EMD Millipore).

Catalyst starting materials C627 (RuCl$_2$(sIMes)(CHC$_6$H$_4$OPr$^i$))[CAS 301224-40-8], trans-748 (trans-RuCl$_2$(sIMes)(phenylindenylidene)(pyridine)) [CAS 103126-76-6], trans-C848 (trans-RuCl$_2$(sIMes)(CHPh)(PPh$_3$)) [CAS 246047-72-3], trans-727 (trans-RuCl$_2$(sIMes)(CHPh)(pyridine)$_2$) [CAS 357186-58-4], trans-C719v (trans-RuCl$_2$(sIMes)(t-butylvinylidene)(pyridine)$_2$) [CAS 496869-36-4], trans-C771 (trans-RuCl$_2$(sIMes)(CHPh)(P(n-Bu)$_3$) [CAS 388095-35-0], trans-C835 (trans-RuCl$_2$(sIMes)(phenylindenylidene)(PPh(Et)$_2$) [CAS 1403376-05-5], trans-C827 (RuCl$_2$(sIMes)(3-methyl-2-butenylidene)(PCy$_3$)) [CAS 253688-91-4] and trans-C705 (RuCl$_2$(sIMes)(3-methyl-2-butenylidene) (pyridine)$_2$) [CAS 507274-22-8] were prepared using known methods.

Ultrene® 99 dicyclopentadiene (DCPD) was obtained from Cymetech Corporation. A modified DCPD base resin containing 20-25% tricyclopentadiene (and small amounts of higher cyclopentadiene homologs) (DCPD-HT) was prepared by heat treatment of Ultrene® 99 DCPD generally as described in U.S. Pat. No. 4,899,005.

$^1$H and $^{13}$C NMR spectra were recorded on a Varian 400 MHz spectrometer. Chemical shifts are reported in ppm downfield from Me$_4$Si by using the residual solvent peak as an internal standard (CDCl$_3$—(δ 7.24 ppm; CD$_2$Cl$_2$—(δ 5.32 ppm). $^{31}$P NMR used a C$_6$D$_6$ solution of triphenylphosphine in a co-axial NMR tube as standard (δ—6.0 ppm). Spectra were analyzed and processed using Vnmr J 4.0 software.

The following abbreviations are used in the examples:

| | |
|---|---|
| DCM/CH$_2$Cl$_2$ | dichloromethane |
| N$_2$ | nitrogen |
| CDCl$_3$ | deuterated chloroform |
| SiO$_2$ | silicagel |
| mL | milliliter |
| ° C. | degrees Celsius |
| EtOAc | ethyl acetate |
| CD$_2$Cl$_2$ | deuterated dichloromethane |
| C627 | |
| h | hour |
| C$_6$D$_6$ | deuterated benzene |

C627

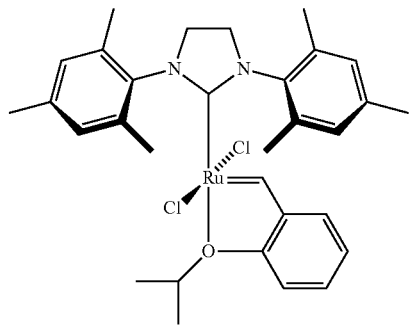

C627 trans-C727

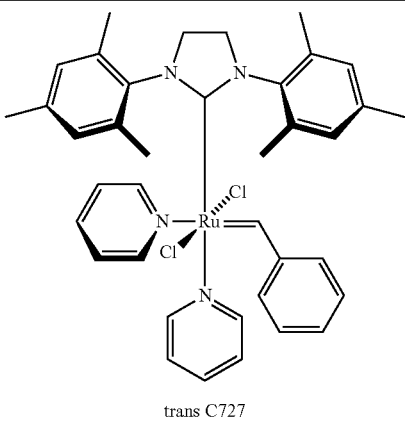

trans C727 trans-C719v

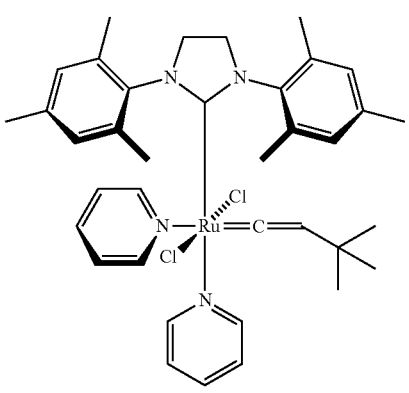

trans-C719v trans-C848

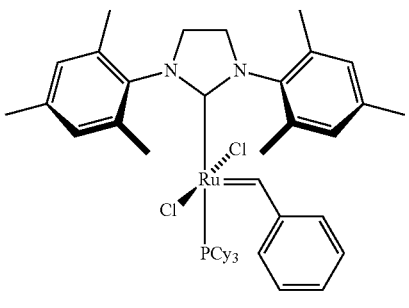

trans-C848 trans-C705

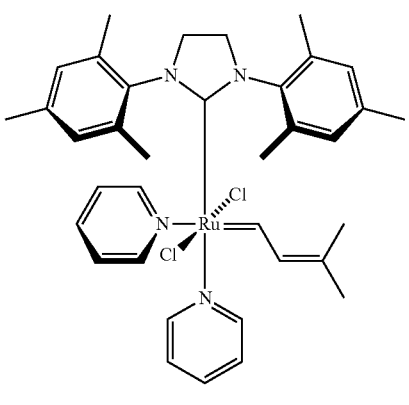

trans-C705

71
-continued trans-C748

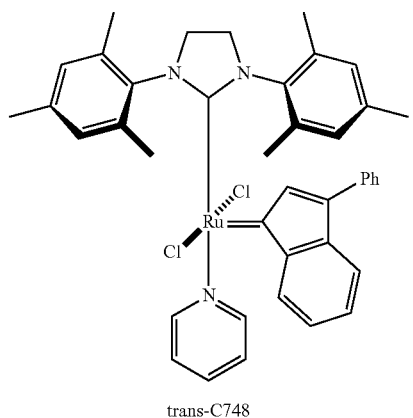

trans-C748 trans-C771

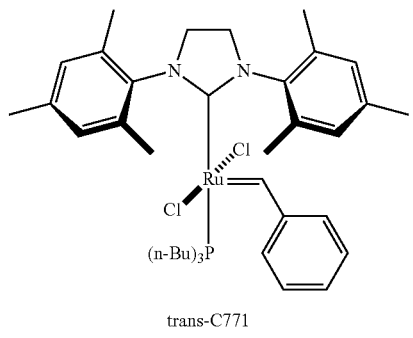

trans-C771 trans-C835

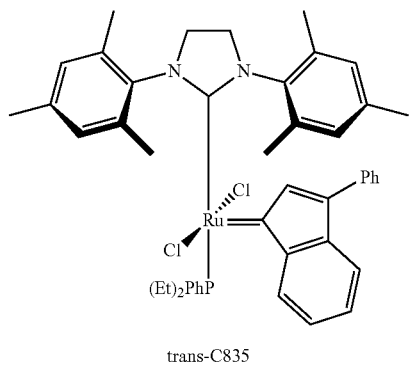

trans-C835 trans-C827

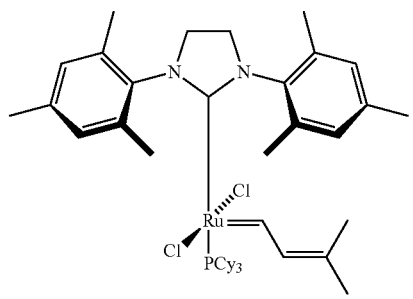

trans-C827

72
EXAMPLES

Example 1

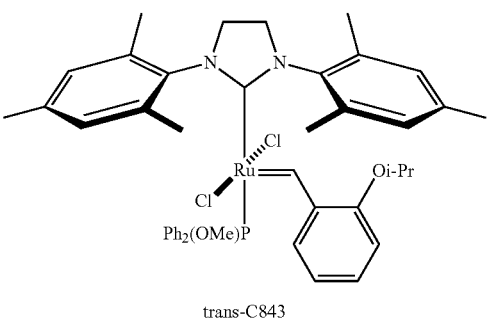

trans-C843 trans-RuCl$_2$(sIMes)(CHC$_6$H$_4$Oi-Pr)(Ph$_2$P(OMe)), trans-C843

C627 (1.0 g, 1.59 mmol) was dissolved in degassed DCM (25 mL) in an 1-neck round-bottomed flask with a magnetic stir bar under nitrogen, to which methyl diphenylphosphinite (0.379 g, 1.75 mmol) was added. The flask was capped with a gas adaptor. The mixture was degassed via N$_2$/vacuum cycle 3-times. After 1 h of stirring at room temperature, the solvent was removed under high vacuum. Degassed methanol (75 mL) was added to the residue. A purple solid was collected by a frit funnel with vacuum filtration. The solid was further dried under high vacuum for 16 h. Yield: 0.7 g (69%). $^1$H NMR (400 MHz, CDCl$_3$, ppm): δ 19.60 (s, Ru=CH, 1H), 7.95 (dd, J=8 Hz, J=2 Hz, 1H), 7.22-6.80 (b, 13H), 6.66 (b, 1H), 6.44 (d, J=8 Hz, 1H), 6.25 (t, J=8 Hz, 1H), 6.02 (b, 1H), 4.42 (septet, J=6 Hz, OCHMe2, 1H), 4.13-3.78 (b, NCH2CH2N, 4H), 3.11 (d, J=7 Hz, OCH$_3$, 3H), 2.72 (b, 3H), 2.58 (b, 3H), 2.52 (b, 3H), 2.30 (s, 3H), 2.03 (b, 3H), 1.85 (s, 3H), 1.49 (b, 3H), 1.29 (b, 3H). $^{31}$P NMR (162 MHz, CDCl$_3$): δ 135.7 (s).

Example 2

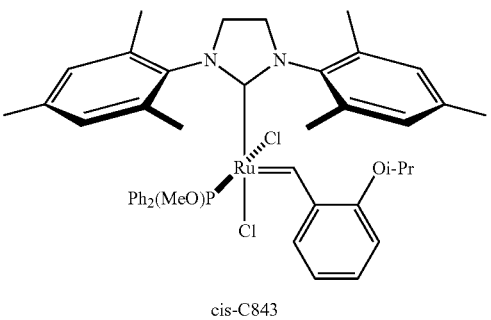

cis-C843 cis-RuCl$_2$(sIMes)(CHC$_6$H$_4$Oi-Pr)(Ph$_2$P(OMe)), cis-C843

C627 (35.0 g, 56 mmol) was dissolved in degassed CH$_2$Cl$_2$ (200 mL) in an 1-neck round-bottomed flask under nitrogen, to which methyl diphenylphosphinite (50 g, 231 mmol) was syringed. The flask was connected to a Friedrich condenser, which was in turn attached to vacuum/nitrogen line. The mixture was degassed by vacuum/nitrogen 3-times. An oil bath was used to heat the flask. The oil bath temperature was kept at 50° C. for 40 h and then cooled to room temperature. The solvent was removed under high vacuum. The residue was dissolved in a minimum amount of $CH_2Cl_2$ and loaded on top of $SiO_2$ gel column (4×3 in, D×H) and eluted with $CH_2Cl_2$. A red band which stuck on column was rinsed down by methanol. The solvent was removed by rotary evaporator and a green solid was obtained. The solid was further purified by recrystallization from $CH_2Cl_2$/Hexanes. Yield: 15 g (32%). $^1$H NMR (400 MHz, $C_6D_6$, ppm): δ 16.45 (d, J=24 Hz, Ru═CH, 1H), 10.11 (dd, J=8 Hz, J=2 Hz, 1H), 7.55 (t, J=9 Hz, 2H), 7.20 (ddd, J=9 Hz, J=7 Hz, J=2 Hz, 1H), 7.00 (m, 3H), 6.87 (dt, J=2 Hz, J=8 Hz, 2H), 6.79 (t, J=8 Hz, 1H), 6.75-6.65 (m, 3H), 6.61 (d, J=10 Hz), 6.20 (m, 2H), 4.11 (septet, J=6 Hz, —OCHMe$_2$, 1H), 3.50-3.06 (m, 4H), 3.38 (d, J=10 Hz, —OCH$_3$, 3H), 2.92 (s, 3H), 2.51 (s, 3H), 2.45 (s, 3H), 2.33 (s, 3H), 1.95 (s, 3H), 1.91 (s, 3H), 1.25 (d, J=6 Hz, 3H, OCH(CH$_3$)(CH$_3$), 3H), 0.97 (d, J=6 Hz, 3H, OCH(CH$_3$)(CH$_3$), 3H). $^{31}$P NMR (162 MHz, $C_6D_6$, ppm): δ 140.9 (b).

Example 3

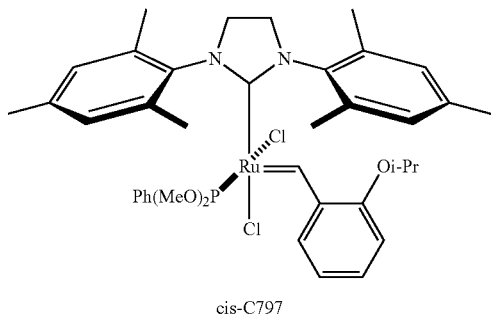

cis-C797 cis-RuCl$_2$(sIMes)(CHC$_6$H$_4$Oi-Pr)(PhP(OMe)$_2$), cis-C797:

To a round-bottomed flask was charged C627 (15.0 g), degassed $CH_2Cl_2$ (100 mL) and a magnetic stir bar under nitrogen, followed the addition of phosphonite PhP(OMe)$_2$ (4.1 g). The solution was stirred for 3.7 h and second portion of phosphonite PhP(OMe)$_2$ (2.05 g) was added. The solution was continued to stir for 2 more hours and the solution was concentrated by a rotary evaporator. A silica gel plug column (4×2.5 in, D×H) was pre-wetted with $CH_2Cl_2$. Low vacuum suction was used to assist elution. The crude was loaded on the top of the column. The first eluent was $CH_2Cl_2$ and a green fraction was collected, that was C627 as verified by NMR. The green fraction was followed by a yellow fraction that appeared to be an oxidation derivative of the phosphonite. The eluent was then switched to gradient mixture of $CH_2Cl_2$/EtOAc. A brown band containing the product was collected. The solvent was removed by a rotary evaporator and the residue was recrystallized from $CH_2Cl_2$/heptanes. Black crystalline solid was obtained (3.1 g). $^1$H NMR (400 MHz, CD$_2$Cl$_2$, ppm): δ 15.83 (d, J=24 Hz, 1H, Ru═CH), 9.16 (dd, J=8 Hz, J=2 Hz, 1H), 7.51 (m, 1H), 7.25 (m, 1H), 7.15 (m, 2H), 7.02-6.88 (m, 5H), 6.66 (s, 1H), 6.61 (d, J=8 Hz, 1H), 6.14 (s, 1H), 4.49 (septet, J=6 Hz, 1H, CHMe$_2$), 4.02-3.62 (m, 4H, CH$_2$CH$_2$), 3.33 (d, J=11 Hz, 3H, OCH$_3$), 3.05 (d, J=12 Hz, OCH$_3$), 2.67 (s, 3H, mestyl methyl), 2.62 (s, 3H, mestyl methyl), 2.46 (s, 3H, mestyl methyl), 2.33 (s, 3H, mestyl methyl), 2.22 (s, 3H, mestyl methyl), 1.95 (s, 3H, mestyl methyl), 1.46 (d, J=6 Hz, 3H, CH(CH$_3$)$_2$), 1.19 (d, J=6 Hz, 3H, CH(CH$_3$)$_2$). $^{31}$P NMR (161.8 MHz, CD$_2$Cl$_2$, ppm): δ 163.84 (b).

Example 4

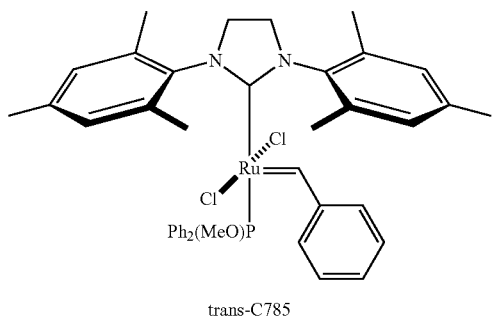

trans-C785 trans-RuCl$_2$(sIMes)(CHPh)(Ph$_2$P(OMe)), trans-C785 trans-C727 (4.35 g, 6.0 mmol) was dissolved in degassed $CH_2Cl_2$ (50 mL) with a magnetic stir bar under nitrogen in a round-bottomed flask. The flask was capped with a gas adaptor. Methyl diphenylphosphinite (2.6 g, 12 mmol) was syringed to the flask under nitrogen flow. The green solution turned brown immediately, which was continued to stir at room temperature for 1 h. The lights were removed under high vacuum, yielding a mixture of black oil and brown crystalline material. The flask was chilled by liquid nitrogen and the resulting solid was broken into small pieces with a spatula. Hexanes (50 mL) was added and the solvent was reduced by a rotary evaporator. The pink solid was collected by a frit funnel with vacuum filtration and washed with hexanes twice (2×25 mL). The solid was dried under high vacuum for 16 h. Yield: 2.91 g (62%). $^1$H NMR (400 MHz, $C_6D_6$, ppm): δ 19.33 (s, 1H, Ru═CH), 7.86 (d, J=8 Hz, 2H), 7.33 (m, 4H), 7.13 (t, J=8 Hz, 1H), 7.10-6.88 (m, 6H), 6.83 (s, 2H), 6.80 (m, 2H), 6.32 (s, 2H), 3.46-3.38 (m, 2H), 3.34-3.25 (m, 2H), 3.29 (d, J=12 Hz, 3H), 2.79 (s, 6H), 2.39 (s, 6H), 2.17 (s, 3H), 1.90 (s, 3H). $^{31}$P NMR (162 MHz, $C_6D_6$, ppm): δ 132.5 (s).

Example 5

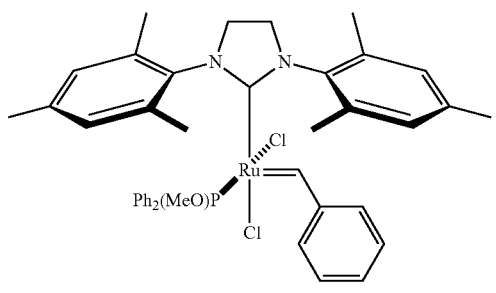

trans-C785 cis-RuCl$_2$(sIMes)(CHPh)(Ph$_2$P(OMe)), cis-C785 trans-C848 (10.0 g, 11.8 mmol) was dissolved in 1,2-dichloroethane (50 mL) with a magnetic stir bar in an 1-neck round-bottomed flask under nitrogen. Methyl diphenylphosphinite (5.1 g, 23.6 mmol) was added via syringe. A gas adaptor was connected to the flask which was then degassed by N$_2$/vacuum cycle 3-times. The flask was connected to nitrogen line and was heated in an oil bath to 70° C. The heating was continued for 16 h. The oil bath was removed and the flask was cooled to room temperature. The solvent was removed in a rotary evaporator. To the residue CH$_2$Cl$_2$ and hexanes (100 mL each) were added. The solvent was reduced to half with a rotary evaporator and solid came out. The solid was collected in a frit funnel with vacuum filtration. The solid was recrystallized from CH$_2$Cl$_2$/methanol and dried und high vacuum for 16 h, yielding a bluish grey solid (7.0 g). $^1$H NMR (400 MHz, CD$_2$Cl$_2$, ppm): δ 15.41 (d, J=25 Hz, 1H, Ru=CH), 7.45-6.95 (m, 17H), 6.65 (s, 1H), 6.10 (s, 1H), 4.04-3.90 (m, 3H), 3.74-3.66 (m, 1H), 3.59 (d, J=10 Hz, 3H, P(OCH$_3$)), 2.77 (s, 3H, ArCH$_3$), 2.69 (s, 3H, ArCH$_3$), 2.39 (s, 3H, ArCH$_3$), 2.37 (s, 3H, ArCH$_3$), 2.11 (s, 3H, ArCH$_3$), 1.95 (s, 3H, ArCH$_3$). $^{31}$P NMR (161.8 MHz, CD$_2$Cl$_2$, ppm): δ 132.32, 132.30.

Example 6

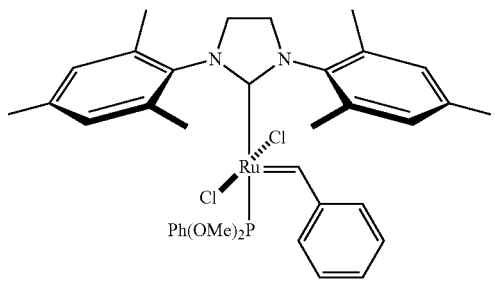

trans-C739 trans-RuCl$_2$(sIMes)(Benzylidene)(PhP(OMe)$_2$), trans-C739 trans-C727 (14.54 g, 20 mmol) was placed in a round-bottomed flask with a magnetic stir bar under N$_2$, to which degassed CH$_2$Cl$_2$ was added (100 mL). Phosphonite PhP(OMe)$_2$ (3.74 g, 22 mmol) was added. The reaction vessel was evacuated and refilled with N$_2$ (3×). The reaction was stirred under N$_2$ for 15 min at ambient temperature (20-25° C.). The solvent was removed under high vacuum to yield a crude solid. The crude solid was dissolved in CH$_2$Cl$_2$ and passed through a silica gel plug (4"×3", D×H). The first fraction was eluted off with CH$_2$Cl$_2$ and a second fraction was eluted off with EtOAc. The first fraction was concentrated by rotatory evaporator to a slurry which was filtered and washed with heptanes to give a yellowish brown solid (4.9 g). $^1$H NMR (400 MHz, CDCl$_3$, ppm): δ 18.81 (s, 1H), 765-7.63 (m, 2H), 7.37-7.41 (m, 1H), 7.21-7.17 (m, 1H), 7.01-6.96 (m, 6H), 6.85 (s, 2H), 6.35 (s, 2H), 4.07-4.05 (m, 2H), 3.94-3.92 (m, 2H), 3.13 (d, J=12 Hz, 6H, P(OCH$_3$)$_2$), 2.59 (s, 6H), 2.25 (s, 3H), 2.18 (s, 6H), 1.99 (s, 3H). $^{31}$P NMR (161.8 MHz, C$_6$D$_6$, ppm): δ 157.04 (s).

Example 7

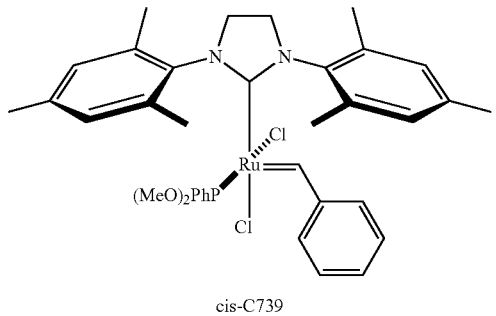

cis-C739 cis-RuCl$_2$(sIMes)(Benzylidene)(PhP(OMe)$_2$), cis-C739

(vide supra trans-RuCl$_2$(sIMes)(Benzylidene)(PhP(OMe)$_2$), trans-C739) The second fraction was concentrated by rotary evaporation to a slurry and filtered and washed with heptanes to yield a violet solid (2.2 g). The crude solid was dissolved in degassed CH$_2$Cl$_2$ (10 mL), followed by precipitation with degassed heptanes (100 mL). Violet crystalline material formed and were filtered and washed with heptanes and dried under high vacuum. Yield: 1.9 g. $^1$H NMR (400 MHz, CDCl$_3$, ppm): δ 15.24 (d, J=22.7 Hz, 1H), 7.81-7.79 (m, 2H), 7.48-7.44 (m, 1H), 7.22-7.18 (m, 2H), 7.17-7.13 (m, 1H), 7.05-7.01 (m, 2H), 6.98-6.96 (m, 2H), 6.94-6.89 (m, 2H), 6.86 (s, 1H), 6.12 (s, 1H), 4.00-3.94 (m, 1H), 3.92-3.85 (m, 2H), 3.73-3.69 (m, 1H), 3.33 (d, J=11 Hz, 3H), 3.08 (d, J=11 Hz, 3H), 2.68 (s, 3H), 2.62 (s, 3H), 2.55 (s, 3H), 2.31 (s, 3H), 2.10 (s, 3H), 2.05 (s, 3H). $^{31}$P NMR (161.8 MHz, C$_6$D$_6$, ppm): δ 158.40 (s).

Example 8

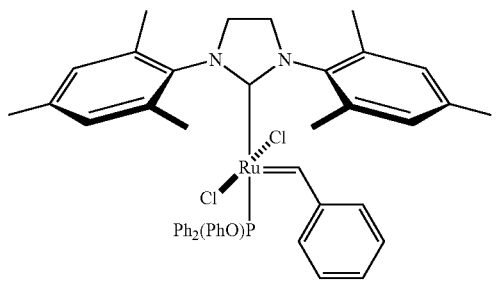

trans-C847 trans-RuCl$_2$(sIMes)(Benzylidene)(Ph$_2$P(OPh)), trans-C847 trans-C727 (7.27 g, 10 mmol) was placed in a round-bottomed flask with a magnetic stir bar under nitrogen, to which degassed CH$_2$Cl$_2$ was added (50 mL). Phosphinite Ph$_2$P(OPh) (3.06 g, 11 mmol) was added via syringe. The reaction vessel was evacuated and refilled with N$_2$ (3×). The reaction was stirred under N$_2$ for 15 min at ambient temperature (20-25° C.). The solvent was removed under high vacuum. Degassed toluene (50 mL) was added and the reaction vessel was vacated and backfilled with N2 (3×). The solvent was removed under high vacuum. The crude material was dissolved in $CH_2Cl_2$ and passed through a silica gel plug (3"×1", D×H). The silica gel plug was washed with $CH_2Cl_2$ and the organics were concentrated and heptanes (50 mL) were added to form a black oil and supernatant. The supernatant was allowed to sit, upon which a solid came out. The solid was filtered and washed with heptanes to yield a brown solid (0.7 g). $^1$H NMR (400 MHz, $CD_2Cl_2$, ppm): δ 18.80 (s, 1H), 7.71 (m, 2H), 7.44 (m, 1H), 7.27 (m, 2H), 7.13-7.02 (m, 10H), 6.92 (s, 2H), 6.85 (m, 2H), 6.78 (m, 1H), 6.44 (m, 2H), 6.38 (s, 2H), 4.10-4.03 (m, 2H), 3.96-3.90 (m, 2H), 2.58 (s, 6H), 2.37 (s, 3H), 2.22 (s, 6H), 2.00 (s, 3H). $^{31}$P NMR (161.8 MHz, $C_6D_6$, ppm): δ 134.58 (s).

Example 9

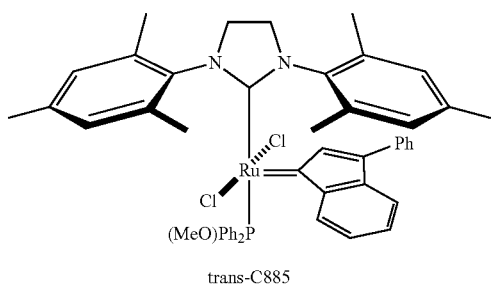

trans-C885 trans-RuCl$_2$(sIMes)(Phenylindenylidene)(Ph$_2$P(OMe)), trans-C885 trans-C748. 2Py (9.06 g, 10 mmol) was placed in a round-bottomed flask with a magnetic stir bar under nitrogen, to which heptanes were added (150 mL). Phosphinite Ph$_2$P(OMe) was added via syringe. The suspension gradually turned red after 1 h of stirring. The purple solid was collected using a frit funnel with vacuum filtration. The solid was then dried under high vacuum for 2 h. Yield: 8.6 g. $^1$H NMR (400 MHz, $CD_2Cl_2$, ppm): δ 8.09 (d, J=7 Hz, 1H), 7.60 (m, 2H), 7.54 (m, 1H), 7.41 (m, 2H), 7.32-6.98 (m, 14H), 6.61 (s, 1H), 6.44 (b, 1H), 6.08 (b, 1H), 4.16-3.80 (m, 4H), 3.23 (d, J=12 Hz, 3H), 2.72 (s, 6H), 2.43 (s, 3H), 2.20 (s, 3H), 2.05 (s, 3H), 1.83 (s, 3H). $^{31}$P NMR (161.8 MHz, $CD_2Cl_2$, ppm): δ 122.1 (s).

Example 10

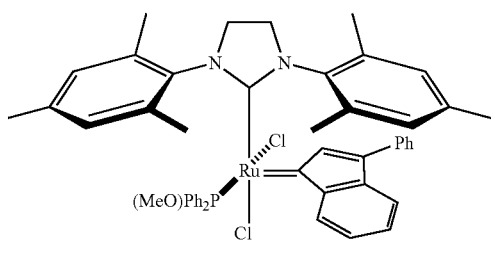

cis-C885 cis-RuCl$_2$(sIMes)(Phenylindenylidene)(Ph$_2$P(OMe)), cis-C885 trans-C748. 2Py (27.18 g, 30 mmol) was placed in a round-bottomed flask with a magnetic stir bar under nitrogen, to which degassed heptanes were added (500 mL). Phosphinite Ph$_2$P(OMe) (6.8 g, 31.5 mmol) was added via syringe. The reaction vessel was evacuated and refilled with N$_2$ (3×). The mixture was stirred under N$_2$ for 1 hr at ambient temperature (20-25° C.). Because there was some undissolved starting material, degassed $CH_2Cl_2$ (250 mL) was added and all solids were dissolved. The solution was passed through a silica plug (2.5"×1.5", D×H) and $CH_2Cl_2$ was used as eluent to remove the first red band of material, which was trans-C885. Then EtOAc was used as eluent to remove a second band that was concentrated and filtered providing brown crystals of cis-C885 (8.49 g). $^1$H NMR (400 MHz, $CD_2Cl_2$, ppm): δ 8.78 (dd, J=8 Hz, J=1 Hz, 1H), 7.52-7.24 (m, 8H), 7.13-6.89 (m, 9H), 6.75 (m, 2H), 6.43 (s, 1H), 6.40 (s, 1H), 6.24 (s, 1H), 6.11 (s, 1H), 3.98-3.63 (m, 4H), 3.66 (d, J=10 Hz, 3H), 2.79 (s, 3H), 2.56 (s, 3H), 2.54 (s, 3H), 2.21 (s, 3H), 1.95 (s, 3H), 1.66 (s, 3H). $^{31}$P NMR (161.8 MHz, $CD_2Cl_2$, ppm): δ 133.3 (s)

Example 11

Isomerization of cis-C885 to trans-C885

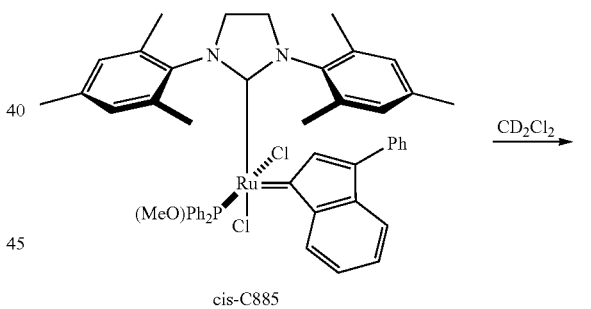

cis-C885

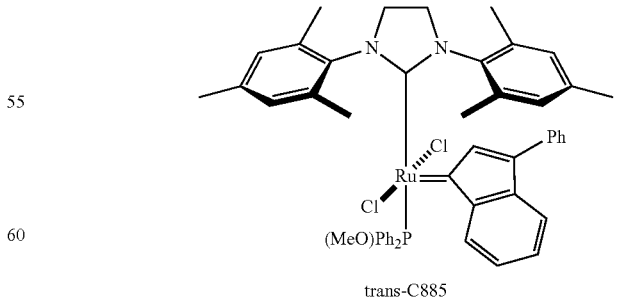

trans-C885

Cis-C885 (50 mg) was dissolved 0.5 mL $CD_2Cl_2$ in an NMR tube. The isomerization was monitored by NMR (FIG. 1, wherein C885B is cis-C885 and C885A is trans-C885).

Example 12

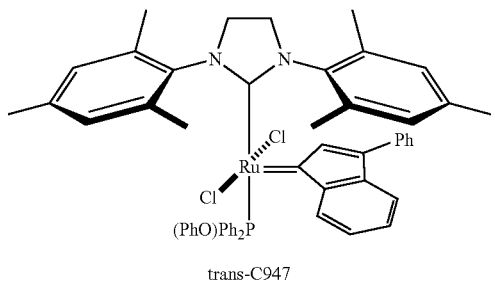

trans-C947 trans-RuCl$_2$(sIMes)(Phenylindenylidene)(Ph$_2$P(OPh)), trans-C947:

trans-C748. 2Py (90.6 g, 100 mmol) was placed in a round-bottomed flask with a magnetic stir bar under nitrogen, to which degassed toluene was added (1 L). Phosphinite Ph$_2$P(OPh) (30.58 g, 110 mmol) was added via syringe. The reaction vessel was evacuated and refilled with N$_2$ (3×). The reaction was stirred under N$_2$ for 1 hr at ambient temperature (20-25° C.). The solvent was removed under high vacuum. Degassed CH$_2$Cl$_2$ (1 L) was added and the reaction vessel was evacuated and refilled with N$_2$ (3×). The solvent was removed under high vacuum and the solid stood in the flask for 2 days. Degassed methanol was added and the precipitate was filtered and washed with methanol. The crude solid was dried under high vacuum. The crude solid was dissolved in CH$_2$Cl$_2$ and filtered through a silica plug (3"×1", D×H). The plug was washed with CH$_2$Cl$_2$ (500 mL). The combined organic eluents were concentrated to half the volume and degassed heptanes (500 mL) were added. The solution was then reduced further under high vacuum to yield a slurry that was filtered and washed with heptanes. The solid was dried under high vacuum to yield trans-C947 (67 g). $^1$H NMR (400 MHz, CDCl$_3$, ppm): δ 8.18 (d, J=7.4 Hz, 1H), 7.58-7.56 (m, 2H), 7.51-7.47 (m, 1H), 7.37-7.33 (m, 2H), 7.24-7.15 (m, 7H), 7.03-6.94 (m, 8H), 6.78-6.74 (m, 2H), 6.71 (s, 1H), 6.66-6.62 (m, 1H), 6.55-6.53 (m, 2H), 6.43 (s, 1H), 6.07 (s, 1H), 4.07-4.13 (m, 2H), 3.82-3.95 (m, 2H), 2.70 (s, 3H), 2.66 (s, 3H), 2.40 (s, 3H), 2.25 (s, 3H), 2.01 (s, 3H) 1.80 (s, 3H). $^{31}$P NMR (161.8 MHz, C$_6$D$_6$, ppm): δ 126.58 (s).

Example 13

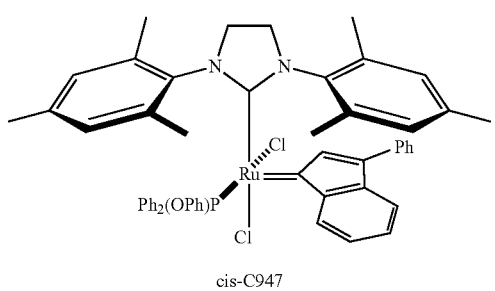

cis-C947 cis-RuCl$_2$(sIMes)(Phenylindenylidene)(Ph$_2$P(OPh)), cis-C947

(vide supra trans-RuCl$_2$(sIMes)(phenylindenylidene)(Ph$_2$P(OPh)), trans-C947). The silica gel plug from the trans-C947 synthesis was then washed with ethyl acetate and a second band came off, that was the cis product. The eluate was concentrated under high vacuum to yield brown crystals. The slurry was filtered and the filtrate was concentrated yielding cis product as brown crystals. The crystals were washed with EtOAc and kept under high vacuum for 16 hours. Yield: 15.0 g. $^1$H NMR (400 MHz, CDCl$_3$, ppm): δ 9.11 (d, J=0.8 Hz, 1H), 7.59-7.55 (m, 2H), 7.49-7.45 (m, 1H), 7.36-7.27 (m, 5H), 7.22-7.18 (m, 2H), 7.12-7.04 (m, 3H), 7.03-6.99 (m, 3H), 6.88-6.86 (m, 1H), 6.82 (s, 1H), 6.67-6.64 (m, 4H), 6.37-6.35 (m, 2H), 6.26 (m, 2H), 6.23 (s, 1H), 6.07 (s, 1H), 3.96-3.93 (m, 1H), 3.74-3.64 (m, 3H), 2.77 (s, 3H), 2.66 (s, 3H), 2.29 (s, 3H), 2.12 (s, 3H), 2.00 (s, 3H), 1.58 (s, 3H). $^{31}$P NMR (161.8 MHz, C$_6$D$_6$, ppm): δ 137.68 (s).

Example 14

C947 cis-trans Isomerization in Solution

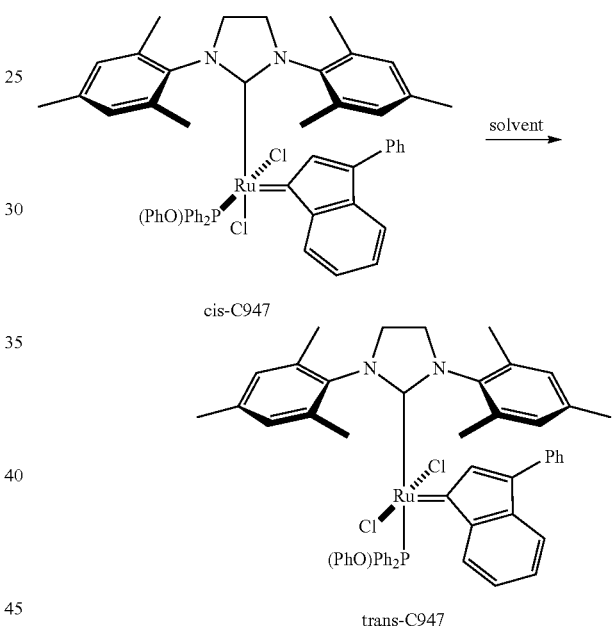

Solution Preparation.

An appropriate amount of anthracene (~5 mg) was dissolved in either 1 mL of CD$_2$Cl$_2$ or 1 mL of C$_6$D$_6$. Upon complete dissolution of the anthracene, the solution was transferred to a vial containing an appropriate amount of catalyst (~20 mg). Catalyst solubilization was aided by sonication. The catalyst/anthracene solutions were passed through a tared 0.2 µm PTFE membrane filter (PALL Acrodisc CR 25 mm). Membrane filters were retained and dried under high vacuum for determination of the mass of insolubles. Filtered solutions were placed in an NMR tube (0.9 mL for C$_6$D$_6$, 0.8 mL for CD$_2$Cl$_2$), in air, capped and allowed to sit at ambient temperature. $^1$H NMR spectra were collected from these samples.

$^1$H NMR Spectroscopy.

$^1$H NMR spectra were collected using a Varian spectrometer operating at 400 MHz. Spectra were collected at ambient temperature, and reported in δ (parts per million) referenced to residual $^1$H signals of the deuterated solvent: dichloromethane 5.32, and benzene 7.16. The $^1$H pulse was 5.95 μs, the collection time was 2.55 s, and the relaxation delay was 1.0 s. For each $^1$H spectrum, 16 transients were collected. $^1$H NMR fid data were subjected to 1 Hz exponential apodization before Fourier transformation (32K real+imaginary points). Relative amounts of ruthenium catalyst bearing cis-chlorides or trans-chlorides was determined by integration of the signal from position 2 of the 3-phenyl indenylidene. Absolute ruthenium catalyst in solution was determined by the sum of cis-chloride and trans-chloride integrations of position 2 of the 3-phenyl indenylidene compared to the integration of the signal of position 9,10 (2H) of the internal standard anthracene.

Results

Solubility.

Anthracene was completely soluble in $CD_2Cl_2$ and $C_6D_6$. trans-C947 and cis-C947 were nearly completely soluble in $CD_2Cl_2$, while cis-C947 was less soluble than trans-C947 in $C_6D_6$ (Table 1). Complete removal of residual solvent from the PTFE membrane filter was not possible, and a portion of the measured residual masses in Table 1 are a result of evaporation of this residual solvent.

TABLE 1

| Catalyst/Solvent | Catalyst mass (mg) | Anthracene mass (mg) | Measured mass on PTFE filter (mg) |
|---|---|---|---|
| trans-C947/$CD_2Cl_2$ | 20.2 | 5.3 | 1.7 |
| trans-C947/$C_6D_6$ | 20.6 | 4.6 | 3.1 |
| cis-C947/$CD_2Cl_2$ | 20.4 | 4.8 | 0.8 |
| cis-C947/$C_6D_6$ | 19.8 | 5.4 | 11.4 | trans-C947 in $C_6D_6$.

Figure 2:
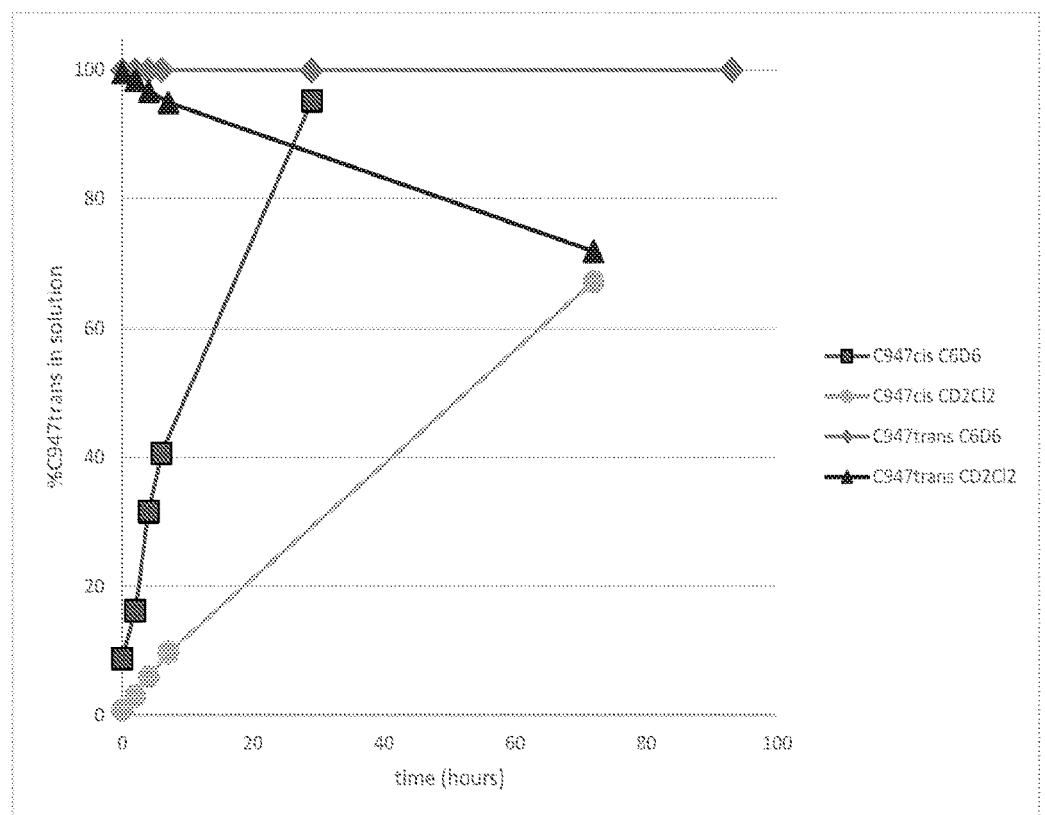
FIG. 2. Percentage of trans-C947 or cis-C947 in solution of $C_6D_6$ or $CD_2Cl_2$.

The signal from position 2 of the 3-phenyl indenylidine is a doublet at δ 8.79 (d, J=7.6 Hz, 1H). This signal was integrated and compared to the anthracene signal at δ 8.15 (s, 2H). No new doublets indicative of cis-C947 were detected over the time course of the experiment (FIG. 2).

cis-C947 in $C_6D_6$.

The signal from position 2 of the 3-phenyl indenylidine is a doublet at δ 9.94 (d, J=7.4 Hz, 1H). This signal was integrated and compared to the anthracene signal at δ 8.15 (s, 2H). A new doublet indicative of trans-C947 appeared at δ 8.79 (d, J=7.4 Hz, 1H) over the time course of the experiment (FIG. 2).

trans-C947 in $CD_2Cl_2$.

The signal from position 2 of the 3-phenyl indenylidine is a doublet at δ 8.18 (d, J=7.5 Hz, 1H). This signal was integrated and compared to the anthracene signal at δ 8.45 (s, 2H). A new doublet indicative of cis-C947 slowly appeared at δ 9.00 (d, J=7.5 Hz, 1H) over the time course of the experiment (FIG. 2).

cis-C947 in $CD_2Cl_2$.

The signal from position 2 of the 3-phenyl indenylidine is a doublet at δ 9.00 (d, J=7.5 Hz, 1H). This signal was integrated and compared to the anthracene signal at δ 8.45 (s, 2H). A new doublet indicative of trans-C947 appeared at δ 8.17 (d, J=7.5 Hz, 1H) over the time course of the experiment (FIG. 2).

Example 14

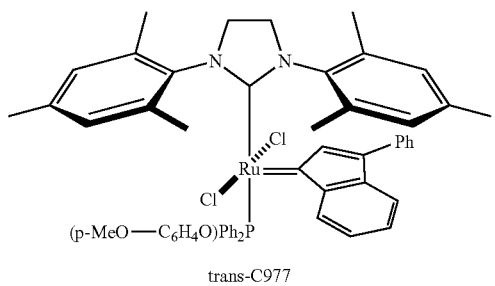

trans-C977 trans-RuCl$_2$(sIMes)(Phenylindenylidene)(Ph$_2$P(O-p-C$_6$H$_4$OMe)), trans-C977 trans-C748. 2Py (9.06 g, 10 mmol) was placed in a round-bottomed flask with a magnetic stir bar under N$_2$, to which degassed CH$_2$Cl$_2$ was added (100 mL). Phosphinite Ph$_2$P(O-p-PhOMe) (3.39 g, 11 mmol) was added via syringe. The reaction vessel was evacuated and refilled with N$_2$ (3×). The reaction was stirred under N$_2$ for 15 min at ambient temperature (20-25° C.). The solvent was removed under high vacuum. Degassed toluene (100 mL) was added and the solvent was removed under high vacuum. For a second time, degassed toluene (100 mL) was added and the solvent was removed under high vacuum. The resulting crude material was attempted to recrystallize in CH$_2$Cl$_2$ (50 mL)/heptanes (50 mL) but yielded a black oil. The supernatant was decanted and the oil was treated with EtOAc (50 mL)/heptanes (50 mL) to yield a black solid powder. The solid was collected and dissolved in CH$_2$Cl$_2$ (500 mL) and passed through a silica gel plug (2"×2", D×H). The silica gel plug was washed with CH$_2$Cl$_2$ (500 mL). The CH$_2$Cl$_2$ eluate and washes were combined and concentrated under high vacuum. The crude residue was attempted to recrystallize in CH$_2$Cl$_2$/heptanes but yielded a black oil. The supernatant was discarded and the oil was put under high vacuum to yield a black foamy solid. Yield: 5.1 g. $^1$H NMR (400 MHz, CDCl$_3$, ppm): δ 8.13 (d, J=8 Hz, 1H), 7.55 (m, 2H), 7.48 (m, 1H), 7.34 (m, 2H), 7.25-7.10 (m, 7H), 7.06-6.92 (m, 8H), 6.71 (s, 1H), 6.41 (m, 3H), 6.24 (m, 2H), 6.05 (s, 1H), 4.12-4.04 (m, 2H), 3.94-3.80 (m, 2H), 3.47 (s, 3H), 2.66 (s, 3H), 2.64 (s, 3H), 2.38 (s, 3H), 2.23 (s, 3H), 1.99 (s, 3H), 1.78 (s, 3H). $^{31}$P NMR (161.8 MHz, CDCl$_3$, ppm): δ 127.30 (s).

Example 15

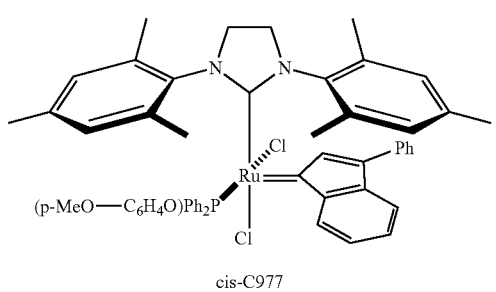

cis-C977 cis-RuCl₂(sIMes)(Phenylindenylidene)(Ph₂P(O-p-C₆H₄OMe)), cis-C977

The foamy solid (trans-C977, 5.0 g) was dissolved in DCM (500 mL) and passed through a silica gel plug (3"×2", D×H). The plug was washed with CH₂Cl₂. The first light red fraction (trans-C977) was discarded and the second dark brown fraction was saved. The eluent was switched to EtOAc and the third fraction was collected. The second and third fractions were combined and the solvent was removed under high vacuum. Methanol was added to wash the solid and the slurry was filtered. The solid was collected and further crystallization with CH₂Cl₂/methanol to yield cis-C977 as light purple solid. Yield: 2.3 g. ¹H NMR (400 MHz, CDCl₃, ppm): δ 9.10 (d, J=7 Hz, 1H), 7.57-7.53 (m, 2H), 7.49-7.45 (m, 1H), 7.37-7.32 (m, 4H), 7.30-7.27 (m, 1H), 7.23-7.19 (m, 2H), 7.11-7.04 (m, 3H), 6.89-6.87 (m, 1H), 6.82 (br s, 1H), 6.68-6.65 (m, 4H), 6.53-6.51 (m, 2H), 6.29-6.26 (m, 4H), 6.23 (s, 1H), 6.08 (s, 1H), 3.98-3.95 (m, 1H), 3.75-3.68 (m, 6H), 2.77 (s, 3H), 2.65 (s, 3H), 2.30 (s, 3H), 2.13 (s, 3H), 2.00 (s, 3H), 1.58 (s, 3H). ³¹P NMR (161.8 MHz, C₆D₆, ppm): δ 136.97 (s).

Example 16

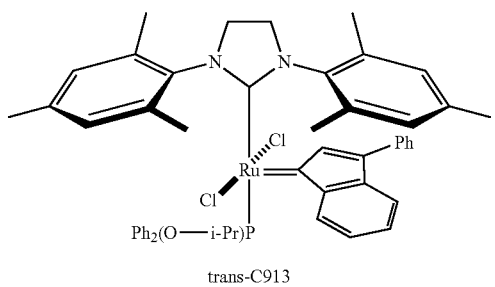

trans-C913 trans-RuCl₂(sIMes)(Phenylindenylidene)(Ph₂P(O-i-Pr)), trans-C913 trans-C748. 2Py (25 g, 27.6 mmol) was placed in a round-bottomed flask with a magnetic stir bar under N₂, to which degassed heptanes were added (400 mL). Phosphinite Ph₂P(O-i-Pr) (7.4 g, 30.4 mmol) was added via syringe. The reaction vessel was evacuated and refilled with N₂ (3×). The reaction was stirred under N₂ for 1 hour at ambient temperature (20-25° C.). More phosphinite Ph₂P(OiPr) (2.0 g, 8 mmol) was added. The reaction was stirred at ambient temperature (20-25° C.) for 16 hr. The slurry was filtered and washed with heptanes. The solid was dissolved in degassed CH₂Cl₂ (250 mL) and the solvent was reduced under high vacuum with a water bath at ambient temperature. Heptanes (100 mL) were added, followed by solvent reduction under high vacuum. A black oil formed at the bottom of the flask. The supernatant was removed and CH₂Cl₂ (100 mL) was added to the black oil and the solvent was reduced under high vacuum. Heptanes (50 mL) were added again a black oil formed at the bottom of the flask. The supernatant was removed and the black oil was dissolved in degassed CH₂Cl₂ (200 mL). The solution was filtered through a silica plug (2"×1", D×H). CH₂Cl₂ was used as an eluent and the first fraction was concentrated to dryness. The resulting solid was broken up and sieved to yield the trans isomer as dark red solid (15.7 g). ¹H NMR (400 MHz, CDCl₃, ppm): δ 7.94 (d, J=8 Hz, 1H), 7.60-7.53 (m, 2H), 7.49 (m, 1H), 7.35 (m, 2H), 7.23-6.90 (m, 15H), 6.59 (s, 1H), 6.40 (s, 1H), 6.04 (s, 1H), 4.17-4.02 (m, 3H), 3.91-3.75 (m, 2H), 2.71 (s, 6H), 2.04 (s, 3H), 2.16 (s, 3H), 2.02 (s, 3H), 1.82 (s, 3H), 0.91 (d, J=6 Hz, 3H), 0.83 (d, J=6 Hz, 3H). ³¹P NMR (161.8 MHz, C₆D₆, ppm): δ 115.28 (s).

Example 17

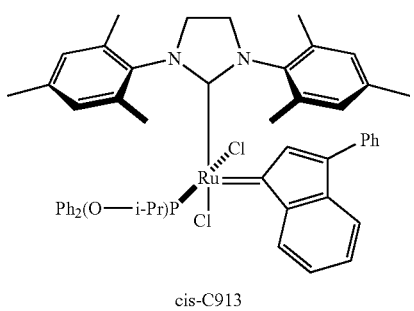

cis-C913 cis-RuCl₂(sIMes)(Phenylindenylidene)(Ph₂P(O-i-Pr)), cis-C913 trans-C913 (2.0 g) was placed in a round-bottomed flask with a magnetic stir bar under nitrogen, to which degassed methanol was added (250 mL). The reaction vessel was evacuated and refilled with N₂ (3×). The reaction was stirred under N₂ for 16 hours at ambient temperature (20-25° C.). The solvent was removed under high vacuum and the crude solid was dissolved in CH₂Cl₂ and filtered through a silica plug (4"×3", D×H). A first fraction was eluted with CH₂Cl₂ and a second fraction was eluted with EtOAc. The second fraction was concentrated to dryness yielding a solid that was washed with methanol (2×100 mL). Dark crystalline material appeared and the solid was filtered and dried to yield the cis isomer. Yield: 0.7 g. ¹H NMR (400 MHz, CDCl₃, ppm): δ 9.02 (d, J=7 Hz, 1H), 7.57-7.55 (m, 2H), 7.49 (m, 2H), 7.44-7.36 (m, 2H), 7.35-7.28 (m, 4H), 7.12-7.06 (m, 2H), 7.02-6.98 (m, 1H), 6.92-6.85 (m, 1H), 6.72-6.67 (m, 3H), 6.64-6.58 (m, 3H), 6.51 (s, 1H), 6.22 (s, 2H), 4.56-4.49 (m, 1H), 3.98-3.93 (m, 1H), 3.74-3.60 (m, 3H), 2.70 (s, 3H), 2.60 (s, 3H), 2.57 (s, 3H), 2.10 (s, 3H), 1.96 (s, 3H), 1.69 (s, 3H), 1.48 (d, J=6 Hz, 3H), 0.62 (d, J=6 Hz, 3H). ³¹P NMR (161.8 MHz, C₆D₆, ppm): δ 129.24 (s).

Example 18

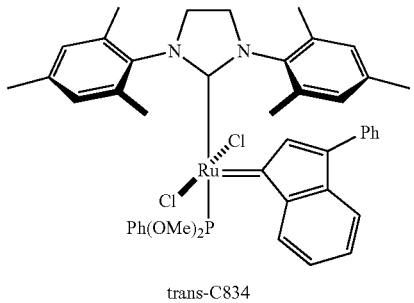

trans-C834 trans-RuCl₂(sIMes)(Phenylindenylidene)(PhP(OMe)₂), trans-C834 trans-C748. 2Py (20 g, 22 mmol) was placed in a round-bottomed flask with a magnetic stir bar under nitrogen, to which degassed heptanes were added (400 mL). Phosphonite PhP(OMe)₂ (4.1 g, 24.2 mmol) was added via syringe. The reaction vessel was evacuated and refilled with N₂ (3×). The slurry was stirred under N₂ for 1 hour at ambient temperature (20-25° C.). The slurry was filtered and the resulting solid was recrystallized from CH₂Cl₂ and heptanes to yield a purple solid (15.8 g). ¹H NMR (400 MHz, CDCl₃, ppm): δ 8.19 (d, J=8 Hz, 1H), 7.62-7.59 (m, 2H), 7.49-7.47 (m, 1H), 7.38-7.34 (m, 2H), 7.20-7.13 (m, 4H), 7.05-7.00 (m, 3H), 6.98-6.96 (m, 1H), 6.89 (s, 1H), 6.85 (s, 1H), 6.75 (s, 1H), 6.42 (s, 1H), 6.07 (s, 1H), 4.12-4.06 (m, 2H), 3.87-3.81 (m, 2H), 3.23-3.12 (m, 6H), 2.65 (s, 6H), 2.25 (s, 3H), 2.22 (s, 3H), 1.98 (s, 3H), 1.77 (s, 3H). ³¹P NMR (161.8 MHz, C₆D₆, ppm): δ 148.60 (s).

Example 19

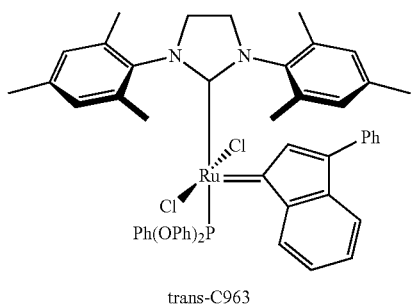

trans-C963 trans-RuCl₂(sIMes)(Phenylindenylidene)(PhP(OPh)₂), trans-C963 trans-C748. 2Py (20.0 g, 22.1 mmol) was placed in a round bottom flask with a magnetic stir bar and dissolved in N₂ sparged toluene (25 mL). Diphenyl phenylphosphonite ((OPh)₂PhP, 7.15 g, 24.3 mmol, 1.1 eq.) was added via syringe. The reaction vessel was evacuated and refilled with N₂ (3×). The reaction was stirred under N₂ for 1 hour at ambient temperature. The solvent was removed from the reaction under high vacuum. To the reaction was added 50 mL of CH₂Cl₂. The flask was stirred briefly, and the solvent removed under reduced pressure. The resulting solid was dried under high vacuum over the weekend. The solid was suspended in CH₂Cl₂ and MeOH, stirred briefly, and the solvents removed by under reduced pressure. The resulting residue was dissolved in CH₂Cl₂, and applied to a silica plug. Elution was achieved by the addition of CH₂Cl₂ until colorless. The CH₂Cl₂ solution was concentrated under reduced pressure and hexanes added. Further concentration gave a slurry, which was filtered and washed with hexanes. The dark solid was dried overnight under high vacuum to yield 15.51 g (73%). ¹H NMR (400 MHz, CDCl₃) δ 8.28 (dd, J=7.4, 1.2 Hz, 1H), 7.72-7.66 (m, 2H), 7.61-7.57 (m, 2H), 7.49 (tt, J=7.5, 1.2 Hz, 1H), 7.41-7.31 (m, 3H), 7.25-7.17 (m, 2H), 7.12 (td, J=7.4, 1.3 Hz, 1H), 7.05 (td, J=7.5, 1.2 Hz, 1H), 6.98-6.77 (m, 9H), 6.75 (s, 1H), 6.69 (s, 1H), 6.67-6.56 (m, 3H), 6.35 (s, 1H), 6.06 (s, 1H), 4.08-3.91 (m, 2H), 3.90-3.70 (m, 2H), 2.57 (s, 3H), 2.54 (s, 3H), 2.26 (s, 3H), 2.17 (s, 3H), 1.96 (s, 3H), 1.74 (s, 3H). ³¹P NMR (162 MHz, CDCl₃) δ 151.47.

Example 20

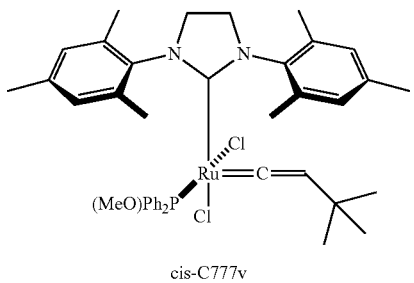

cis-C777v cis-RuCl₂(sIMes)(t-butylvinylidene)(Ph₂P(OMe)), cis-C777v trans-C719v (5.0 g, 7.0 mmol) was placed in a round-bottomed flask with a magnetic stir bar under nitrogen, to which degassed CH₂Cl₂ was added (40 mL). Phosphinite Ph₂P(OMe) (2.26 g, 10.5 mmol) was added via syringe. The reaction vessel was evacuated and refilled with N₂ (3×). The reaction was stirred under N₂ for 60 min at ambient temperature (20-25° C.) yielding a yellow crystalline solid. The crude material was filtered, washed with heptanes and dried under high vacuum to provide a crude yellow solid (3.6 g). The crude yellow solid (1.6 g) was dissolved in degassed CH₂Cl₂ (200 mL) and filtered through Celite. The filtrate was concentrated under high vacuum and the resulting solid was recrystallized in CH₂Cl₂/heptanes. The crystals were filtered and washed with heptanes and dried under high vacuum to yield a yellow solid. Yield: 1.3 g. ¹H NMR (400 MHz, CD₂Cl₂, ppm): δ 7.46-7.41 (m, 1H), 7.39-7.28 (m, 5H), 7.18-7.14 (m, 3H), 7.00 (s, 1H), 6.95 (s, 1H), 6.90-6.85 (m, 2H), 6.64 (s, 1H), 4.06-3.85 (m, 4H), 3.35 (d, J=11 Hz, 3H), 2.80 (s, 3H), 2.77 (s, 3H) 2.40 (s, 6H), 2.33 (s, 3H), 2.09 (s, 3H), 1.93 (d, J=5 Hz, 1H), 0.33 (s, 9H). ³¹P NMR (161.8 MHz, C₆D₆, ppm): δ 135.15 (s).

Example 21

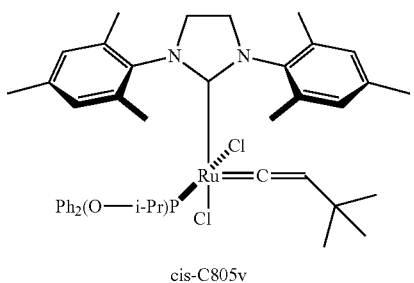

cis-C805v cis-RuCl₂(sIMes)(t-butylvinylidene)(Ph₂P(O-i-Pr)), cis-C805v trans-C719v (5.0 g, 7.0 mmol) was placed in a round-bottomed flask with a magnetic stir bar under N₂, to which degassed and dried toluene was added (30 mL). Phosphinite Ph₂P(O-i-Pr) (1.9 g, 7.7 mmol) was added via syringe. The reaction vessel was evacuated and refilled with N₂ (3×). The solid was not dissolved so degassed CH₂Cl₂ (10 mL) was added. The reaction was stirred under N₂ for 60 min at ambient temperature (20-25° C.) yielding a flocculent solid. The crude material was filtered, washed with heptanes and dried under high vacuum to provide a crude solid. The filtrate was concentrated under high vacuum to yield a solid that was washed with heptanes. The crude solids were combined and treated with degassed CH₂Cl₂ (20 mL) and the reaction vessel was vacated and backfilled with N₂ (3×). Some more PPh₂(O-i-Pr) (0.8 g) was added and the reaction was stirred under N₂ for 60 min at ambient temperature (20-25° C.). The material was concentrated under high vacuum and the resulting crude product was recrystallized with CH₂Cl₂/heptanes to yield a powder. The powder was subsequently recrystallized with CH₂Cl₂/methanol to provide a microcrystalline solid. Yield: 3.5 g. $^1$H NMR (400 MHz, CDCl₃, ppm): δ 7.58-7.53 (m, 2H), 7.34-7.26 (m, 4H), 7.12 (s, 1H), 7.08-7.06 (m, 2H), 6.95 (s, 2H), 6.92-6.79 (m, 2H), 6.65 (s, 1H), 4.26-4.22 (m, 1H), 4.12-4.06 (m, 1H), 4.01-3.93 (m, 2H), 3.81-3.76 (m, 1H), 2.85 (s, 3H), 2.81 (s, 3H), 2.39-2.34 (m, 12H), 1.95 (d, J=5 Hz, 1H), 1.27 (d, J=6 Hz, 3H), 0.52 (d, J=6 Hz, 3H), 0.39 (s, 9H). $^{31}$P NMR (161.8 MHz, C₆D₆, ppm): δ 130.17 (s).

Example 22

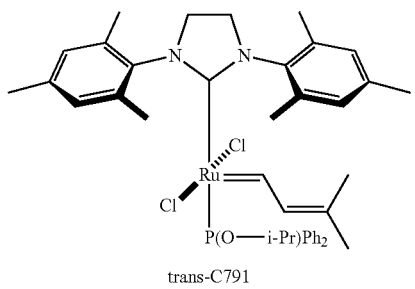

trans-C791 trans-RuCl₂(sIMes)(3-methyl-2-butenylidene)(Ph₂P(O-i-Pr)), trans-C791

In an argon filled glove box, a 40 mL scintillation vial equipped with a magnetic stirbar was charged with C705 (2.00 g, 2.84 mmol) and dichloromethane (15 ml). To the stirring solution was added Phosphinite Ph₂P(O-i-Pr) (0.693 g, 2.84 mmol) in dichloromethane (5 mL). The reaction was stirred at room temperature for one hour then devolatilized. The resulting residue was recrystallized from dichloromethane/pentane at room temperature affording trans-C791 (1.49 g, 66.1%, >95% purity). $^1$H NMR (400 MHz, CD₂Cl₂, ppm): δ18.43 (d, J=11.2 Hz, 1H), 7.30-7.08 (m, 10H), 6.90 (s, 2H), 6.84-6.79 (m, 1H), 6.77 (s, 2H), 4.04-3.85 (m, 4H), 3.83-3.71 (m, 1H), 2.56 (s, 6H), 2.35 (s, 6H), 2.32 (s, 3H), 2.23 (s, 3H), 1.12 (s, 3H), 0.98 (s, 3H), 0.95 (d, J=6.0 Hz, 6H). $^{31}$P NMR (161.8 MHz, CD₂Cl₂, ppm): δ 126.6 (s).

Example 23

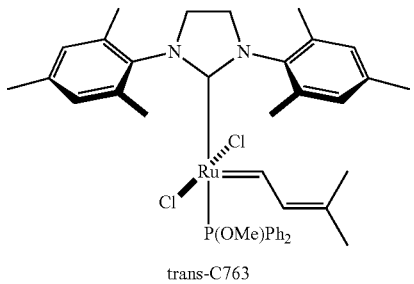

trans-C763 trans-RuCl₂(sIMes)(3-methyl-2-butenylidene)(Ph₂P(OMe)), trans-C763

In an argon filled glove box, a 40 mL scintillation vial equipped with a magnetic stir bar was charged with C705 (2.00 g, 2.84 mmol) and dichloromethane (15 ml). To the stirring solution was added Phosphinite Ph₂P(OMe) (0.556 mL, 2.84 mmol) in dichloromethane (5 mL). The reaction was stirred at room temperature for one hour then devolatilized. The resulting residue was recrystallized from dichloromethane/pentane at room temperature affording trans-C763 (1.35 g, 62.2%, >95% purity). $^1$H NMR (400 MHz, CD₂Cl₂, ppm): δ18.37 (d, J=11.2 Hz, 1H), 7.36-7.29 (m, 2H), 7.27-7.15 (m, 8H), 7.06-7.00 (m, 1H), 6.88 (s, 2H), 6.79 (s, 2H), 4.13-3.87 (m, 4H), 3.15 (d, J=12.8 Hz, 3H), 2.56 (s, 6H), 2.37 (s, 6H), 2.32 (s, 3H), 2.24 (s, 3H), 1.10 (s, 3H), 1.03 (s, 3H). $^{31}$P NMR (161.8 MHz, CD₂Cl₂, ppm): δ 134.4 (s).

Example 24

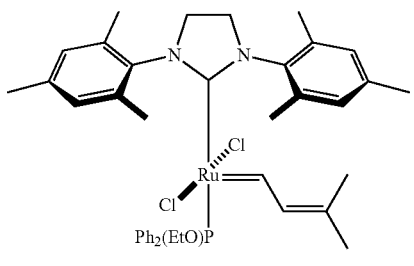

trans-C777 trans-RuCl₂(sIMes)(3-methyl-2-butenylidene)(Ph₂P(OEt)), trans-C777

In an argon filled glove box, a 40 mL scintillation vial equipped with a magnetic stir bar was charged with C705 (2.00 g, 2.84 mmol) and dichloromethane (15 ml). To the stirring solution was added Phosphinite Ph₂P(OEt) (0.607 mL, 2.84 mmol) in dichloromethane (5 mL). The reaction was stirred at room temperature for one hour then devolatilized. The resulting residue was recrystallized from toluene/pentane at −35° C. affording trans-C777 (1.48 g, 67.2%, >95% purity). $^1$H NMR (400 MHz, CD₂Cl₂, ppm): δ18.39 (d, J=11.2 Hz, 1H), 7.34-7.26 (m, 2H), 7.24-7.14 (m, 8H), 7.03-6.95 (m, 1H), 6.89 (s, 2H), 6.79 (s, 2H), 4.08-3.88 (m, 4H), 3.36 (pseudo pentet, J=6.9 Hz, 2H), 2.56 (s, 6H), 2.36 (s, 6H), 2.32 (s, 3H), 2.24 (s, 3H), 1.11 (s, 3H), 1.07 (t, J=6.9 Hz, 3H), 1.03 (s, 3H). $^{31}$P NMR (161.8 MHz, CD$_2$Cl$_2$, ppm): δ 129.8 (s).

Example 25

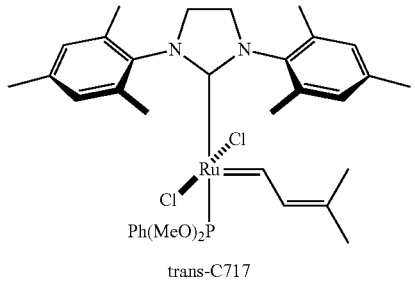

trans-C717 trans-RuCl$_2$(sIMes)(3-methyl-2-butenylidene)(PhP(OMe)$_2$), trans-C717 trans-C705 (28.7 g, 40.1 mmol) was placed in a round-bottomed flask with a magnetic stir bar under nitrogen, to which degassed CH$_2$Cl$_2$ was added (500 mL). Phosphonite PhP(OMe)$_2$ (10.3 g, 61 mmol) was added. The reaction vessel was evacuated and refilled with N$_2$ (3×). The reaction was stirred under N$_2$ for 60 min at ambient temperature (20-25° C.). The solvent was removed under high vacuum to yield a crude solid. The crude solid was dissolved in CH$_2$Cl$_2$ (50 mL) and passed through a silica gel plug (2"×1", D×H). The product fraction was eluted off with CH$_2$Cl$_2$ (200 mL). Heptanes (200 mL) was added and the solution was concentrated to provide a black oil. To the black oil EtOAc was added and a yellow solid appeared that was filtered and washed with heptanes to give a beige solid (9.19 g). The solid was recrystallized with CH$_2$Cl$_2$ (25 mL), EtOAc (50 mL), and heptanes (50 mL) to give 6.19 g of product. $^1$H NMR (400 MHz, CDCl$_3$, ppm): δ 18.19 (dd, J=12 Hz and 1 Hz, 1H), 7.30-7.17 (m, 5H), 7.02-6.99 (m, 1H), 6.80 (s, 2H), 6.70 (s, 2H), 4.06-4.00 (m, 2H), 3.87-3.93 (m, 2H), 3.19 (d, J=12 Hz, 6H), 2.56 (s, 6H), 2.32 (s, 6H), 2.21 (s, 3H), 2.18 (s, 3H), 1.02 (s, 3H), 0.97 (s, 3H). $^{31}$P NMR (161.8 MHz, C$_6$D$_6$, ppm): δ 160.00 (s).

Example 26

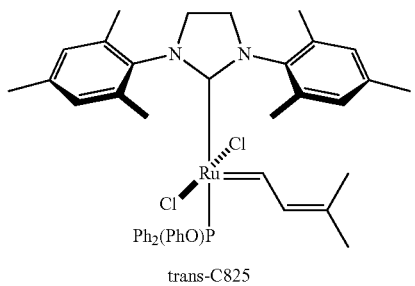

trans-C825 trans-RuCl$_2$(sIMes)(3-methyl-2-butenylidene)(Ph$_2$P(OPh)), trans-C825 trans-C705 (70.5 g, 100 mmol) was placed in a round-bottomed flask with a magnetic stir bar under N$_2$, to which degassed CH$_2$Cl$_2$ was added (500 mL). Phosphinite Ph$_2$P(OPh) (30.58 g, 110 mmol) was added. The reaction vessel was evacuated and refilled with N$_2$ (3×). The reaction was stirred under N$_2$ for 1 hr at ambient temperature (20-25° C.). The solvent was removed under high vacuum and degassed toluene was added (500 mL). The reaction vessel was evacuated and refilled with N$_2$ (3×). The reaction was stirred under N$_2$ for 1 hr at ambient temperature (20-25° C.). The solvent was removed under high vacuum and degassed toluene was added (500 mL). Solid particles in the solution were filtered away and the solvent of the filtrate was removed under high vacuum to give a solid residue. Degassed methanol (500 mL) was then added to wash the solid, after which the solid was filtered and washed with methanol. The solid was then dissolved in CH$_2$Cl$_2$ and more phosphinite was added (1.0 g, 3.6 mmol). The solution was concentrated and degassed heptanes (250 mL) were added. The solvent was then reduced and the flask was stored in a freezer for 16 h. Solid formed and was filtered and washed with heptanes. The solid was dissolved in CH$_2$Cl$_2$ (100 mL) and the solution was passed through silica gel plug (3"×2", D×H). The filtrate was dried with a rotary evaporator to dryness. The solid was dissolved in degassed CH$_2$Cl$_2$ (250 mL) and reduced to ca 100 mL. Heptanes (500 mL) was slowly dripped into the solution with an addition funnel. Solid was precipitated and filtered. The filtrate was washed with heptanes and dried under high vacuum. The crude solid was dissolved in CH$_2$Cl$_2$ (40 mL) and again submitted to the slow addition of heptanes (500 mL) by an addition funnel. Once again a solid appeared and was filtered and washed with heptanes to give the product. Yield: 6.2 g. $^1$H NMR (400 MHz, CD$_2$Cl$_2$, ppm): δ 18.29 (d, J=11.2 Hz, 1H), 7.35-7.30 (m, 5H), 7.23-7.18 (m, 4H), 7.16-7.12 (m, 1H), 6.97-6.93 (m, 2H), 6.85-6.80 (m, 3H), 6.75 (s, 2H), 6.59-6.56 (m, 2H), 4.03-3.97 (m, 2H), 3.92-3.87 (m, 2H), 2.50 (s, 6H), 2.3 (s, 6H), 2.31 (s, 3H), 2.21 (s, 3H), 1.02 (s, 3H), 1.00 (s, 3H). $^{31}$P NMR (161.8 MHz, CD$_2$Cl$_2$, ppm): δ 137.11 (s).

Catalytic Activity of Complexes

Examples 27 (a)-(x)

Catalytic activity of complexes was evaluated in ring opening metathesis polymerization (ROMP) reactions as follows. A 250 mL beaker was filled with 100 g of DCPD-HT monomer. The monomer was equilibrated to the desired temperature in an oil bath (30° C.+/−0.5° C.). A J-Type thermocouple was suspended directly into the center of the monomer. The catalyst under study was dissolved in solvent (either toluene or CH$_2$Cl$_2$) to form a catalyst solution and the catalyst solution was then added to the monomer at a molar ratio of 45,000:1 (monomer:catalyst) to form a ROMP composition. Addition of the catalyst to the monomer to form the ROMP composition denoted the start of the ROMP reaction and hence, this was time point zero. Temperature readings were recorded using the thermocouple. The exotherm time was determined by measuring the amount of time that passed (i.e., the time difference) between time point zero and the time point that a propagating interface of the ROMP composition was first visually observed as the ROMP composition transitioned from a liquid state or gel state to a cured polymer state. ROMP reactions were stopped 2 hours after addition of the catalyst solution to the monomer. Time to exotherm is expressed by: slow >120 minutes; moderate 30-120 minutes; medium 1-<30 minutes; fast<1 minute and peak exotherm temperature are shown in Table 2.

TABLE 2

| Example 27 | Catalyst | DCPD-HT Monomer Temperature (° C.) | Time to Exotherm (min.) | Peak Exotherm Temperature (° C.) |
|---|---|---|---|---|
| (a) | trans-C843 | 30 | fast | 189 |
| (b) | cis-C843 | 30 | slow | 180 |
| (c) | cis-C797 | 30 | slow | NR |
| (d) | trans-C739 | 30 | medium | 194 |
| (e) | cis-C739 | 30 | slow | NR |
| (f) | trans-C847 | 30 | fast | NR |
| (g) | trans-C885 | 30 | medium | 193 |
| (h) | cis-C885 | 30 | moderate | 191 |
| (i) | trans-C947 | 30 | fast | 194 |
| (j) | cis-C947 | 30 | medium | 196 |
| (k) | trans-C977 | 30 | medium | 195 |
| (l) | cis-C977 | 30 | medium | 192 |
| (m) | trans-C913 | 30 | fast | NR |
| (n) | cis-C913 | 30 | medium | 195.51 |
| (o) | trans-C834 | 30 | fast | NR |
| (p) | trans-C791 | 30 | fast | NR |
| (q) | trans-C763 | 30 | medium | 196 |
| (r) | trans-C777 | 30 | medium | 189 |
| (s) | trans-C717 | 30 | fast | NR |
| (t) | trans-C825 | 30 | fast | NR |
| (u) | trans-C771 | 50 | medium | 205.7 |
| (v) | trans-C835 | 50 | moderate | 204.86 |
| (w) | trans-C885 | 50 | medium | 199.22 |
| (x) | trans-C827 | 30 | medium | 196 |

NR = not reported

Surprisingly, the trans and cis catalysts of the invention show different times to exotherm during ROMP conditions. In the phenylindenylidene series the trans catalysts show faster rates than the cis catalysts, similarly, in the benzylidene series, the trans catalysts show faster rates than the cis catalysts. The same trend is observed between the trans and cis phosphinite and phosphonite catalyst series.

To successfully mold an article, it is important to be able to control the rate at which a ROMP composition polymerizes. In a typical molding scenario, following catalysis the viscosity of the ROMP composition increases, progressing from a liquid state, through a gel state, followed by an exotherm event to give the final polymer. In particular, the ROMP composition should not exotherm (i.e., cure) before the mold is filled. Time periods required to fill a mold may vary from less than a minute to several minutes to several hours. Being able to pick and choose from a wide variety of catalysts which offer different ranges of times to exotherm is an advantage for the molding techniques and for the manufacturing of articles.

What is claimed is:

1. A metal carbene olefin metathesis catalyst represented by the structure of Formula (V):

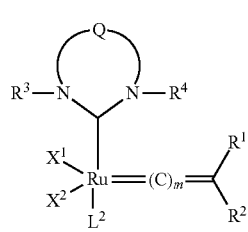

Formula (V)

wherein

Q is a two-atom linkage having the structure —$CR^{11}R^{12}$—$CR^{13}R^{14}$— or —$CR^{11}$=$CR^{13}$—, wherein $R^{11}$, $R^{12}$, $R^{13}$, and $R^{14}$ are independently hydrogen, hydrocarbyl, substituted hydrocarbyl, heteroatom-containing hydrocarbyl, substituted heteroatom-containing hydrocarbyl, or functional groups;

$R^3$ and $R^4$ is unsubstituted phenyl or phenyl substituted with one or more substituents selected from the group consisting of $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide;

$X^1$ and $X^2$ are independently halogen; and are bonded to Ru in a trans orientation;

$L^2$ is represented by Formula (1) or Formula (2):

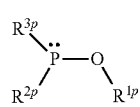

Formula (1)

wherein: $R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl,

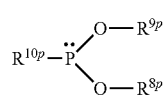

Formula (2)

wherein: $R^{8p}$, $R^{9p}$, $R^{10p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl, m is 0, 1, or 2;

$R^1$ and $R^2$ are independently hydrogen, hydrocarbyl, substituted hydrocarbyl, heteroatom-containing hydrocarbyl, substituted heteroatom-containing hydrocarbyl, or $R^1$ and $R^2$ may be linked together to form a ring that may be substituted or unsubstituted; and with the proviso that the catalyst of Formula (V) is not of structure:

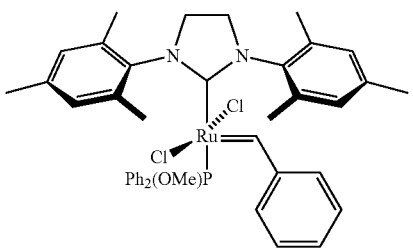

2. The metal carbene olefin metathesis catalyst according to claim 1, wherein:

m is 0;

Q is a two-atom linkage having the structure —$CR^{11}R^{12}$—$CR^{13}R^{14}$—, wherein $R^{11}$, $R^{12}$, $R^{13}$, and $R^{14}$ are each hydrogen;

R³ and R⁴ are each phenyl substituted with up to three substituents selected from methyl or isopropyl;

X¹ and X² are Cl;

R¹ is hydrogen, R² is phenyl, vinyl, optionally substituted with one or more moieties selected from $C_1$-$C_6$ alkyl, or $C_1$-$C_6$ alkoxy; or R¹ and R² may be linked together to form a phenylindenylidene.

3. The metal carbene olefin metathesis catalyst according to claim 2, wherein:

L² is represented by Formula (1):

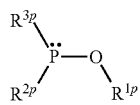

Formula (1)

wherein: $R^{1p}$, $R^{2p}$, $R^{3p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl.

4. The metal carbene olefin metathesis catalyst according to claim 3, wherein:

$R^{1p}$ is selected from the group consisting of methyl, ethyl, isopropyl, n-butyl, sec-butyl, tert-butyl, 4-methoxyphenyl, benzyl and phenyl; and $R^{2p}$ and $R^{3p}$ are each phenyl.

5. The metal carbene olefin metathesis catalyst according to claim 4, wherein the catalyst is selected from the group consisting of:

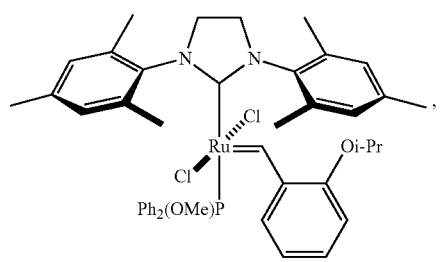

trans-C843

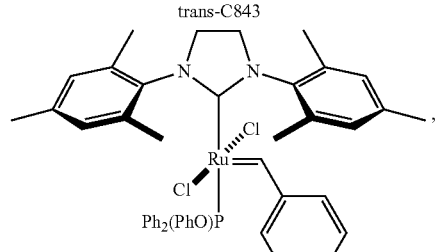

trans-C847

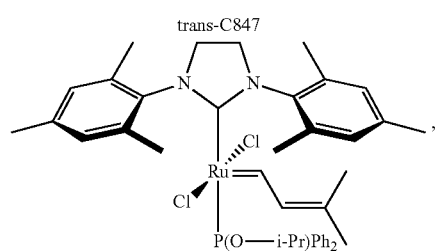

trans-C791

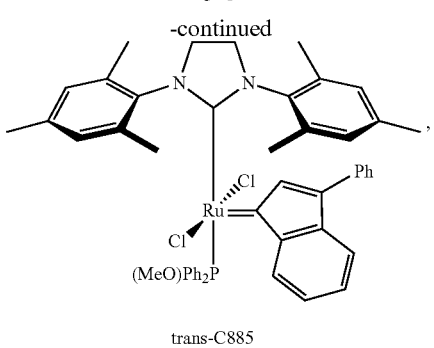

trans-C885

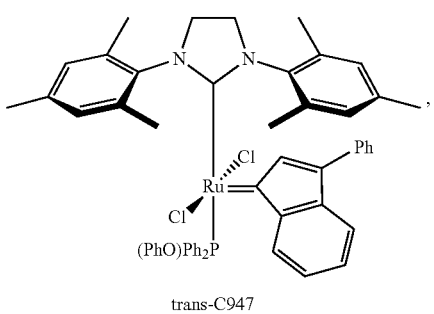

trans-C947

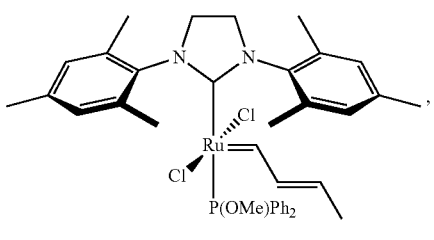

trans-C763

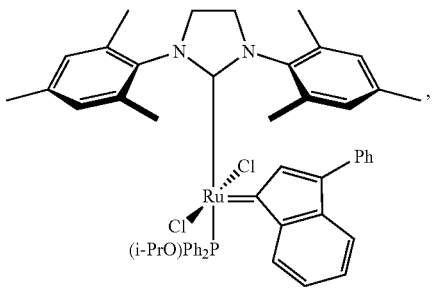

trans-C913

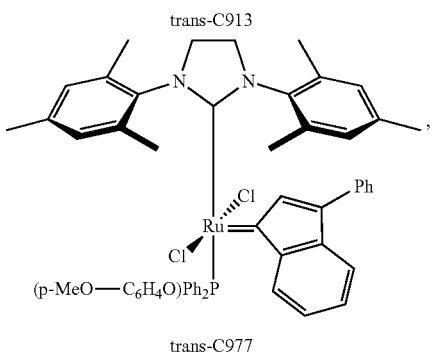

trans-C977

-continued

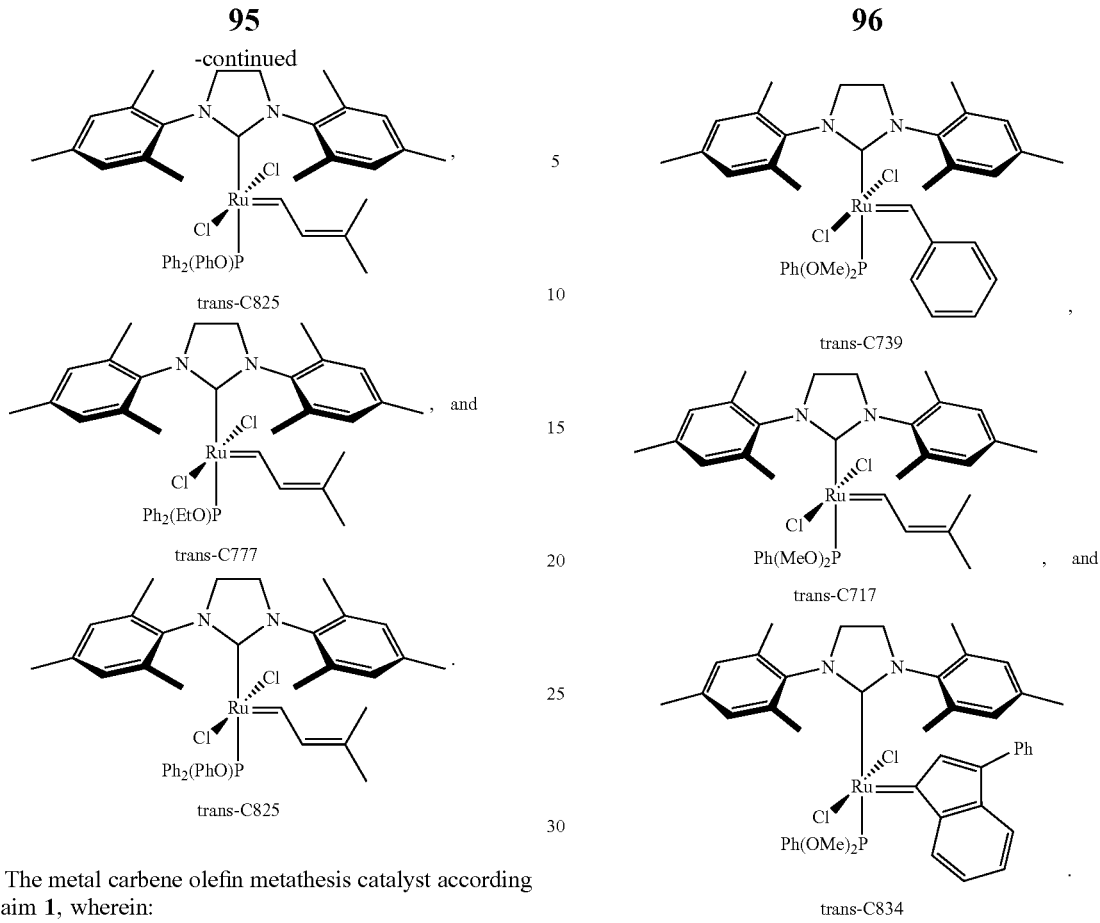

trans-C825 trans-C777 trans-C825 trans-C739 trans-C717 trans-C834

6. The metal carbene olefin metathesis catalyst according to claim 1, wherein:
m is 0;
Q is a two-atom linkage having the structure —$CR^{11}R^{12}$—$CR^{13}R^{14}$—, wherein $R^{11}$, $R^{12}$, $R^{13}$, and $R^{14}$ are independently hydrogen;
$R^3$ and $R^4$ are each phenyl substituted with up to three substituents selected from methyl or isopropyl;
$X^1$ and $X^2$ are Cl;
$R^1$ is hydrogen, $R^2$ is phenyl, vinyl, optionally substituted with one or more moieties selected from $C_1$-$C_6$ alkyl, or $C_1$-$C_6$ alkoxy; or $R^1$ and $R^2$ may be linked together to form a phenylindenylidene.

7. The metal carbene olefin metathesis catalyst according to claim 6, wherein:
$L^2$ is represented by Formula (2):

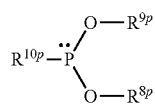

Formula (2)

wherein: $R^{8p}$, $R^{9p}$, $R^{10p}$ are each independently substituted or unsubstituted $C_6$-$C_{10}$ aryl, or substituted or unsubstituted $C_1$-$C_{10}$ alkyl, or substituted or unsubstituted $C_3$-$C_8$ cycloalkyl.

8. The metal carbene olefin metathesis catalyst according to claim 7, wherein: $R^{8p}$ and $R^{9p}$ are each independently selected from methyl, ethyl, isopropyl, n-butyl, sec-butyl, tert-butyl, 4-methoxyphenyl, benzyl, or phenyl; and $R^{10p}$ is phenyl.

9. The metal carbene olefin metathesis catalyst according to claim 8, wherein the catalyst is selected from the group consisting of:

10. A ROMP composition comprising at least one resin composition and at least one metal carbene olefin metathesis catalyst, wherein the resin composition comprises at least one cyclic olefin and wherein the at least one metal carbene olefin metathesis catalyst is selected from the group consisting of:

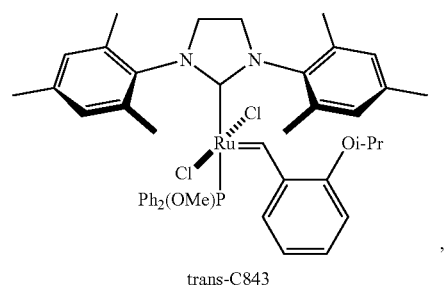

trans-C843

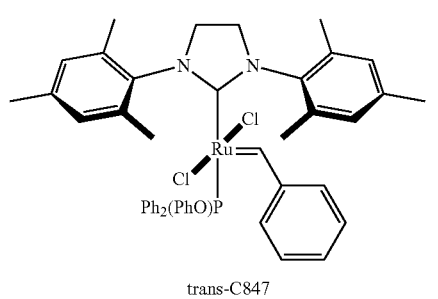

trans-C847

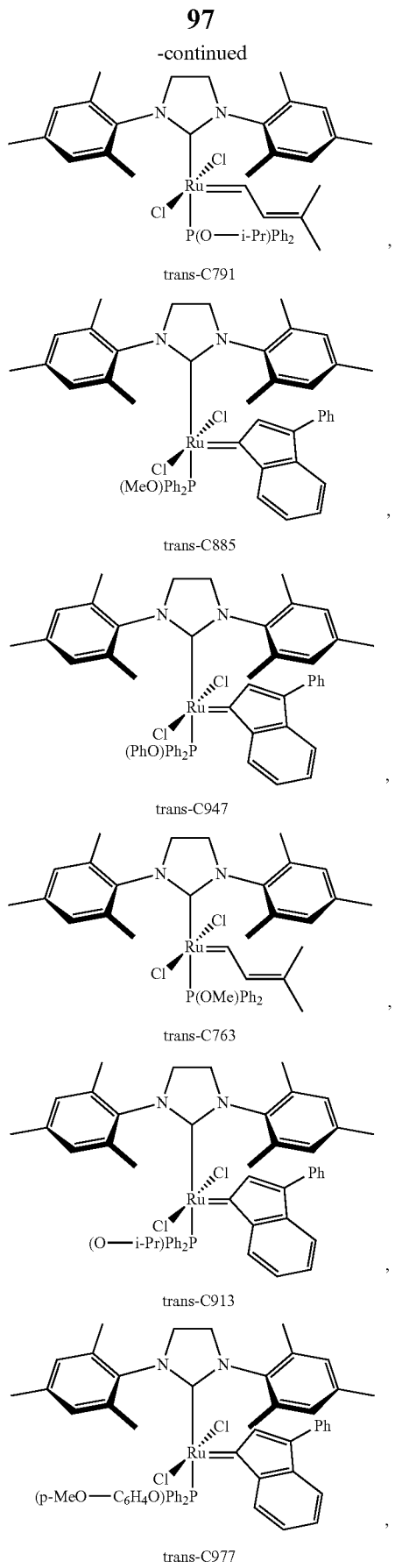
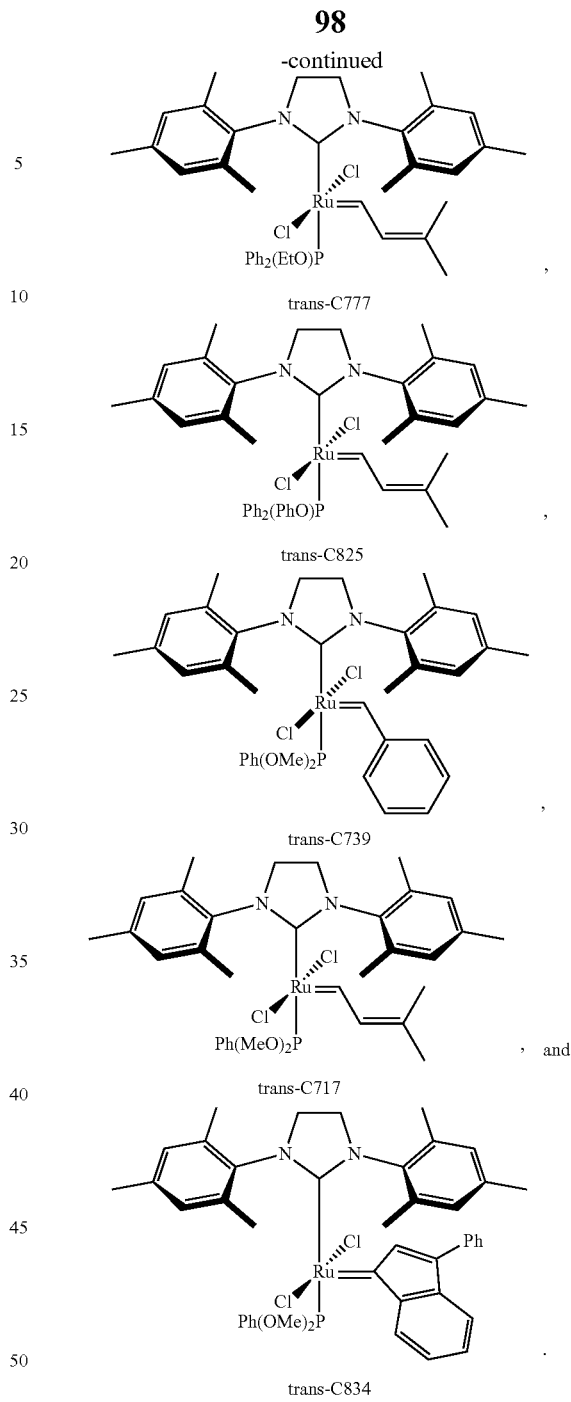

11. The ROMP composition according to claim 10, wherein the at least one cyclic olefin is a norbornene derivative.

12. A ROMP composition comprising at least one resin composition and at least one metal carbene olefin metathesis catalyst according to claim 1, wherein the resin composition comprises at least one cyclic olefin.

13. The ROMP composition according to claim 12, wherein the at least one cyclic olefin is a norbornene derivative.

14. A ROMP composition comprising at least one resin composition and at least one metal carbene olefin metathesis catalyst according to claim 4, wherein the resin composition comprises at least one cyclic olefin.

15. The ROMP composition according to claim 14, wherein the at least one cyclic olefin is a norbornene derivative.

16. A ROMP composition comprising at least one resin composition and at least one metal carbene olefin metathesis catalyst according to claim 8, wherein the resin composition comprises at least one cyclic olefin.

17. The ROMP composition according to claim 16, wherein the at least one cyclic olefin is a norbornene derivative.

* * * * *